United States Patent
Khater et al.

(10) Patent No.: US 12,111,263 B2
(45) Date of Patent: Oct. 8, 2024

(54) METHODS FOR ANALYSIS OF SINGLE MOLECULE LOCALIZATION MICROSCOPY TO DEFINE MOLECULAR ARCHITECTURE

(71) Applicants: Simon Fraser University, Burnaby (CA); University of British Columbia, Vancouver (CA)

(72) Inventors: Ismail M. Khater, Burnaby (CA); Ghassan Hamarneh, Vancouver (CA); Ivan Robert Nabi, Vancouver (CA); Fanrui Meng, Shanghai (CN)

(*) Notice: Subject to any disclaimer, the term of this patent is extended or adjusted under 35 U.S.C. 154(b) by 680 days.

(21) Appl. No.: 16/769,422

(22) PCT Filed: Dec. 5, 2018

(86) PCT No.: PCT/CA2018/051553
§ 371 (c)(1),
(2) Date: Jun. 3, 2020

(87) PCT Pub. No.: WO2019/109181
PCT Pub. Date: Jun. 13, 2019

(65) Prior Publication Data
US 2020/0300763 A1    Sep. 24, 2020

Related U.S. Application Data

(60) Provisional application No. 62/594,642, filed on Dec. 5, 2017.

(51) Int. Cl.
G02B 21/36    (2006.01)
G01N 21/64    (2006.01)
(Continued)

(52) U.S. Cl.
CPC ..... *G01N 21/6458* (2013.01); *G01N 21/6428* (2013.01); *G01N 33/5005* (2013.01);
(Continued)

(58) Field of Classification Search
None
See application file for complete search history.

(56) References Cited

U.S. PATENT DOCUMENTS 7,838,302 B2 * 11/2010 Zhuang ............. G01N 15/1429
436/171
2017/0038574 A1 * 2/2017 Zhuang ............. G01N 21/6458
2017/0251191 A1 * 8/2017 Huang ................. G02B 21/22

FOREIGN PATENT DOCUMENTS

EP             2535755 A1   12/2012
WO    WO2014046606 A1    3/2014
WO    WO-2017027818 A1 *  2/2017 ............. G01J 3/14

OTHER PUBLICATIONS

Jia et al. "Isotropic 3D Super-resolution Imaging with a Self-bending Point Spread Function", Nat Photonics, vol. 8, pp. 302-306, DOI:10.1038/nphoton.2014.13, Nov. 7, 2014, 12 pages.
(Continued)

*Primary Examiner* — Neil N Turk
(74) *Attorney, Agent, or Firm* — Quarles & Brady LLP

(57) ABSTRACT

A method of super-resolution microscopy is provided. The method includes mapping three-dimensional location of each single emission event in a plurality of single emission events from a series of optical images of a sample to create a point cloud. The point cloud is filtered or refined. Clusters within the point cloud are identified and characterized allowing for an assessment of molecular architecture.

23 Claims, 46 Drawing Sheets

(51) Int. Cl.
*G01N 33/50* (2006.01)
*G01N 33/58* (2006.01)
*G01N 33/68* (2006.01)
*G02B 21/00* (2006.01)
*G02B 27/58* (2006.01)
*G06T 3/4053* (2024.01)

(52) U.S. Cl.
CPC ....... *G01N 33/582* (2013.01); *G01N 33/6803* (2013.01); *G01N 2021/6439* (2013.01); *G01N 2201/12* (2013.01)

(56) References Cited

OTHER PUBLICATIONS

Karrenbauer et al. "Blinking Molecule Tracking", Computer Science, pp. 1-12, arXiv:1212.5877, Mar. 29, 2013, 12 pages.

Khater et al. "Super Resolution Network Analysis Defines the Molecular Architecture 1-54 Of Caveolae and Caveolin-1 Scafolds", Scientific Reports, vol. 8, Article No. 9009, pp. 1-15, DOI:10.1038/s41598-018-27216-4, Jun. 13, 2018, 15 pages.

Rollins et al. "Stochastic approach to the molecular counting problem in superresolution 1-54 microscopy", PNAS 112 (2), E110-E118, doi.org/10.1073/pnas.1408071112, Published online Dec. 22, 2014, 9 pages.

Shashkov A et al. "Single-molecule fluorescence microscopy review: shedding new 1-54 light on old problems", Bioscience Reports, 37, pp. 1-19, DOI: 10.1042/BSR20170031, Jul. 21, 2017, 19 pages.

Georgieva et al. "Superresolution microscopy for bioimaging at the nanoscale: from 1-54 concepts to applications in the nucleus", Research and Reports in Biology, vol. 6, pp. 157-169, Sep. 28, 2015, 13 pages.

International Search Report and Written Opinion, International Application No. PCT/CA2018/051553, mailed Feb. 21, 2019, 9 pages.

\* cited by examiner

FIG. 6B
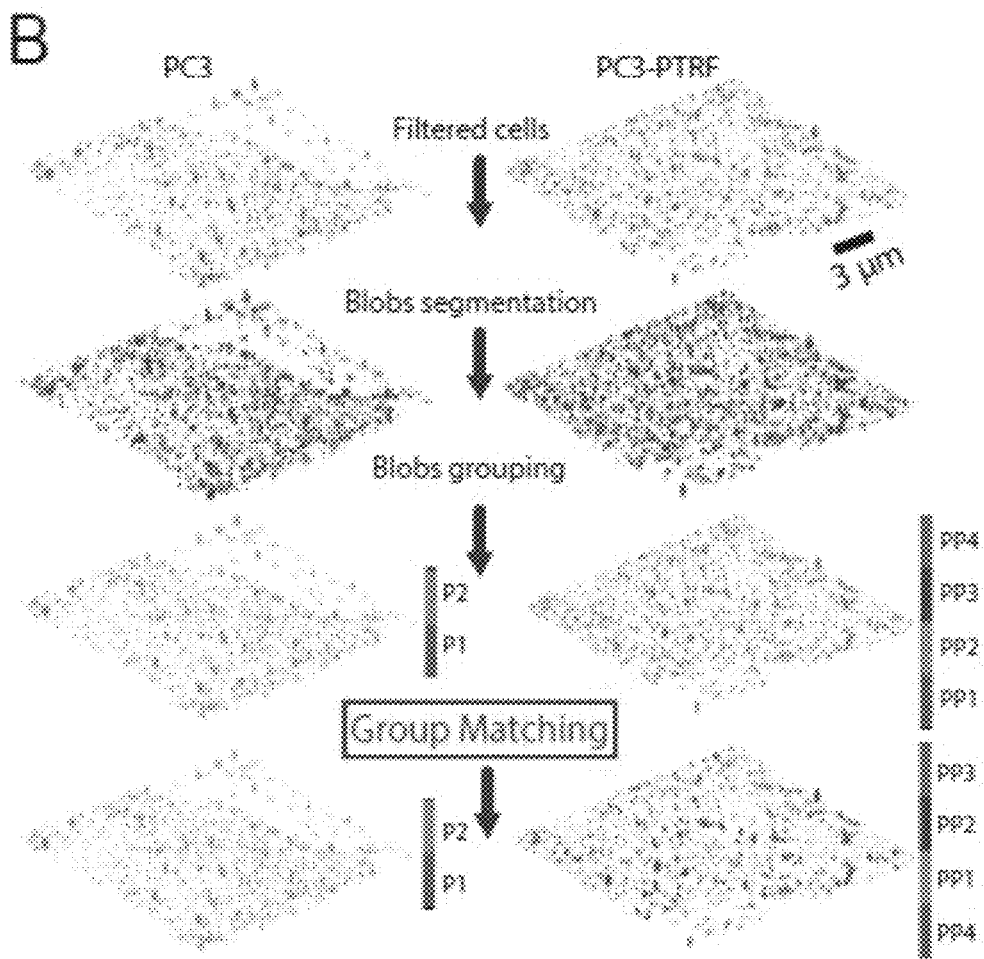
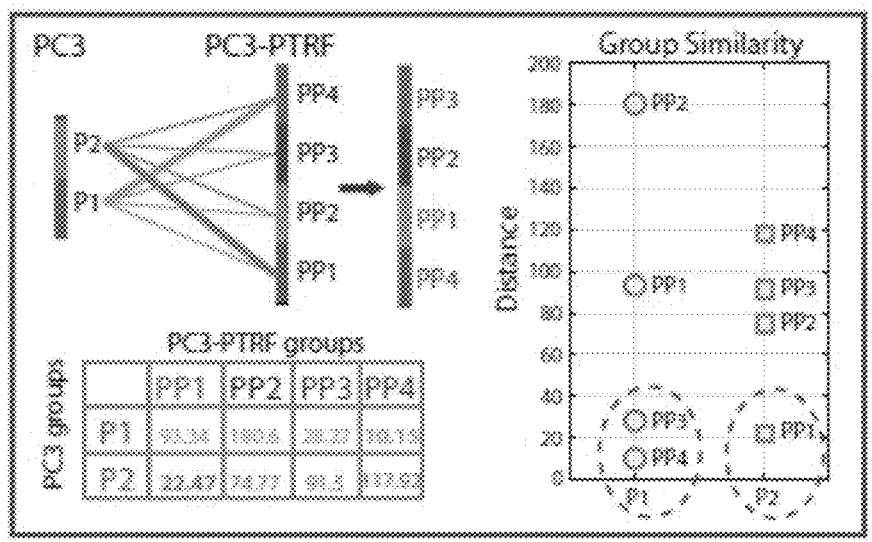

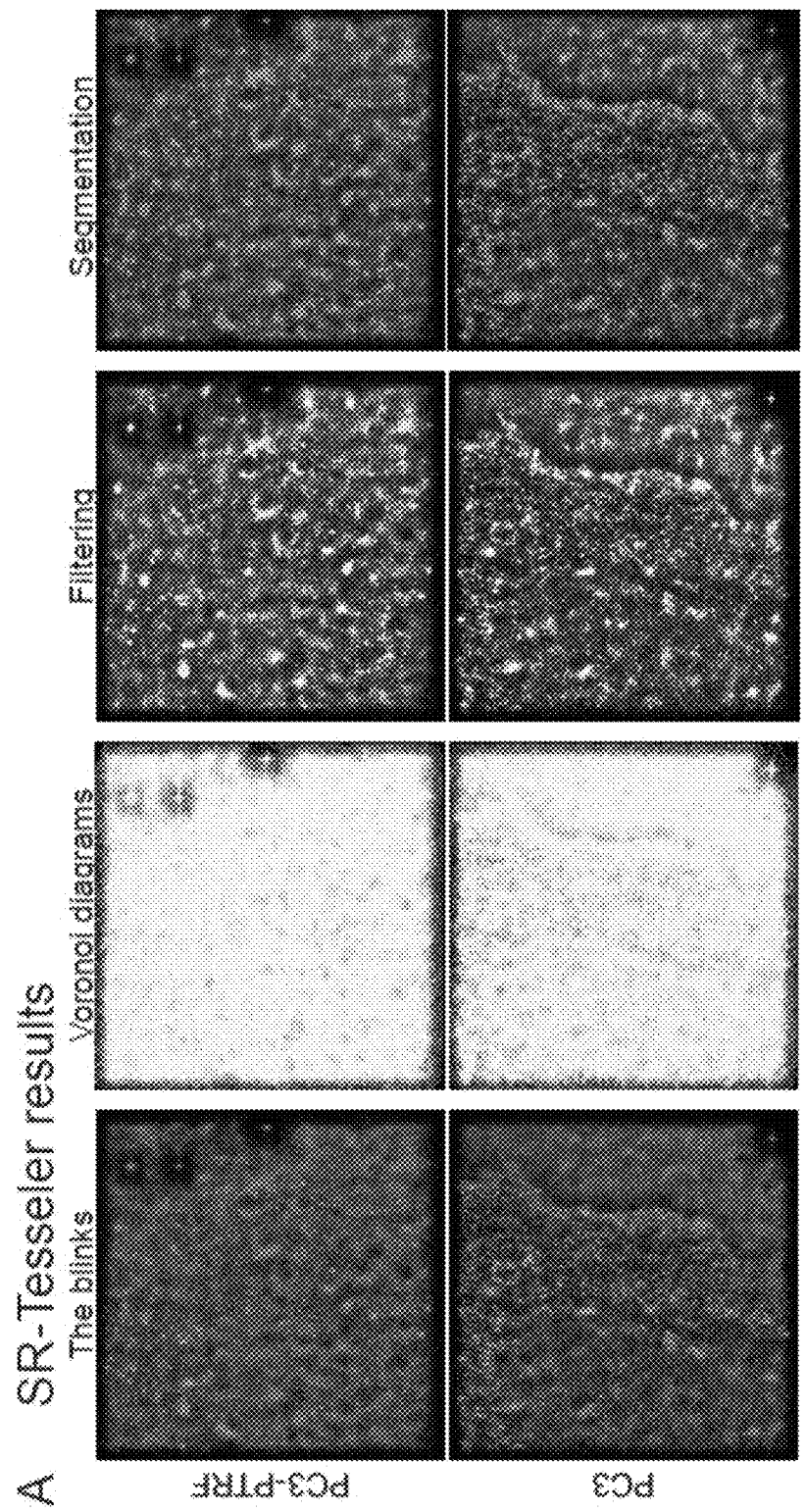

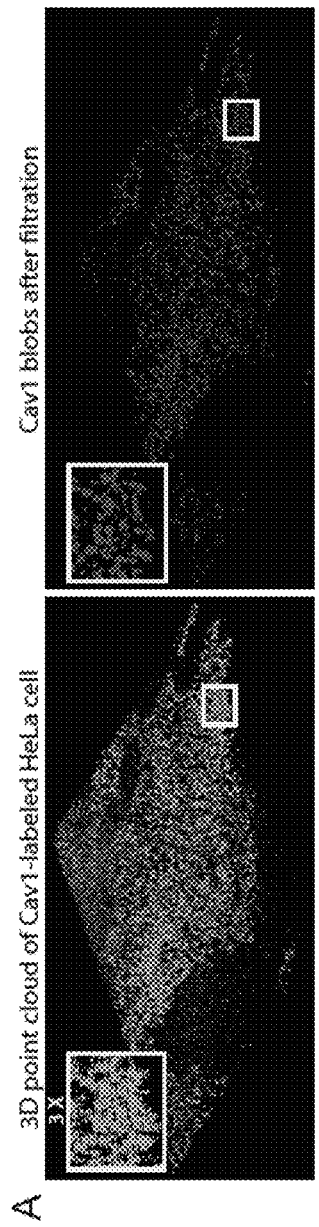
Fig. 12A
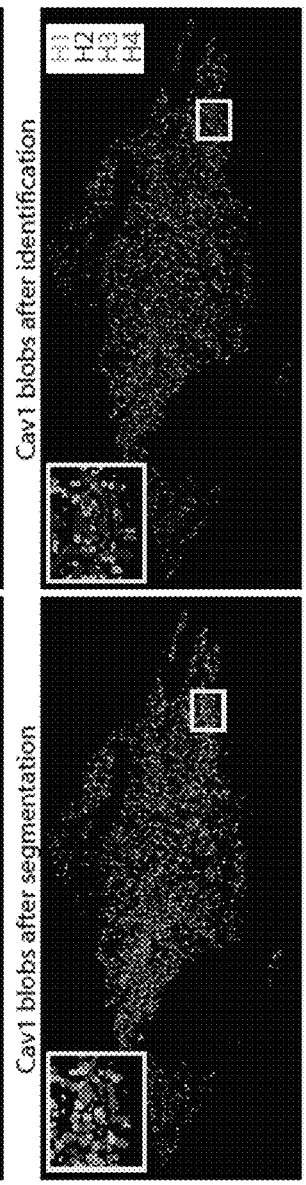
Fig. 12B
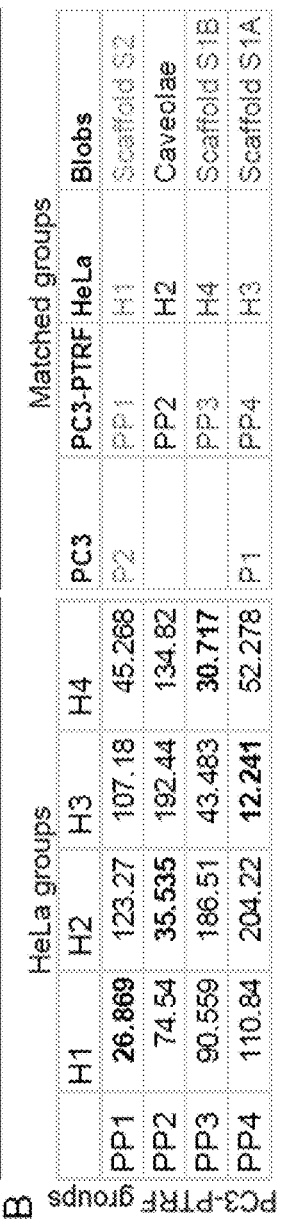
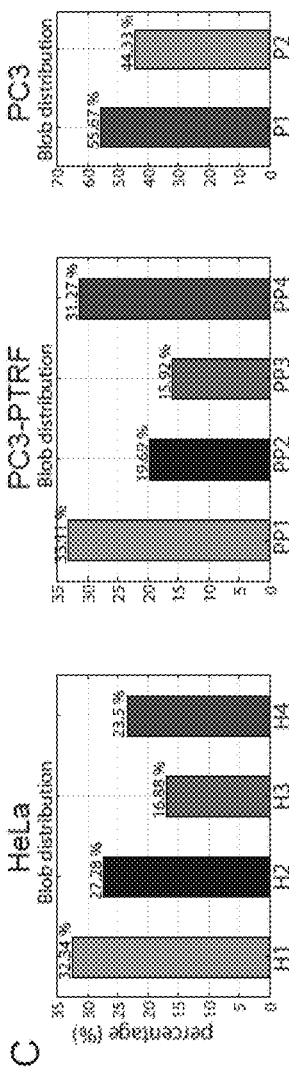
Fig. 12C

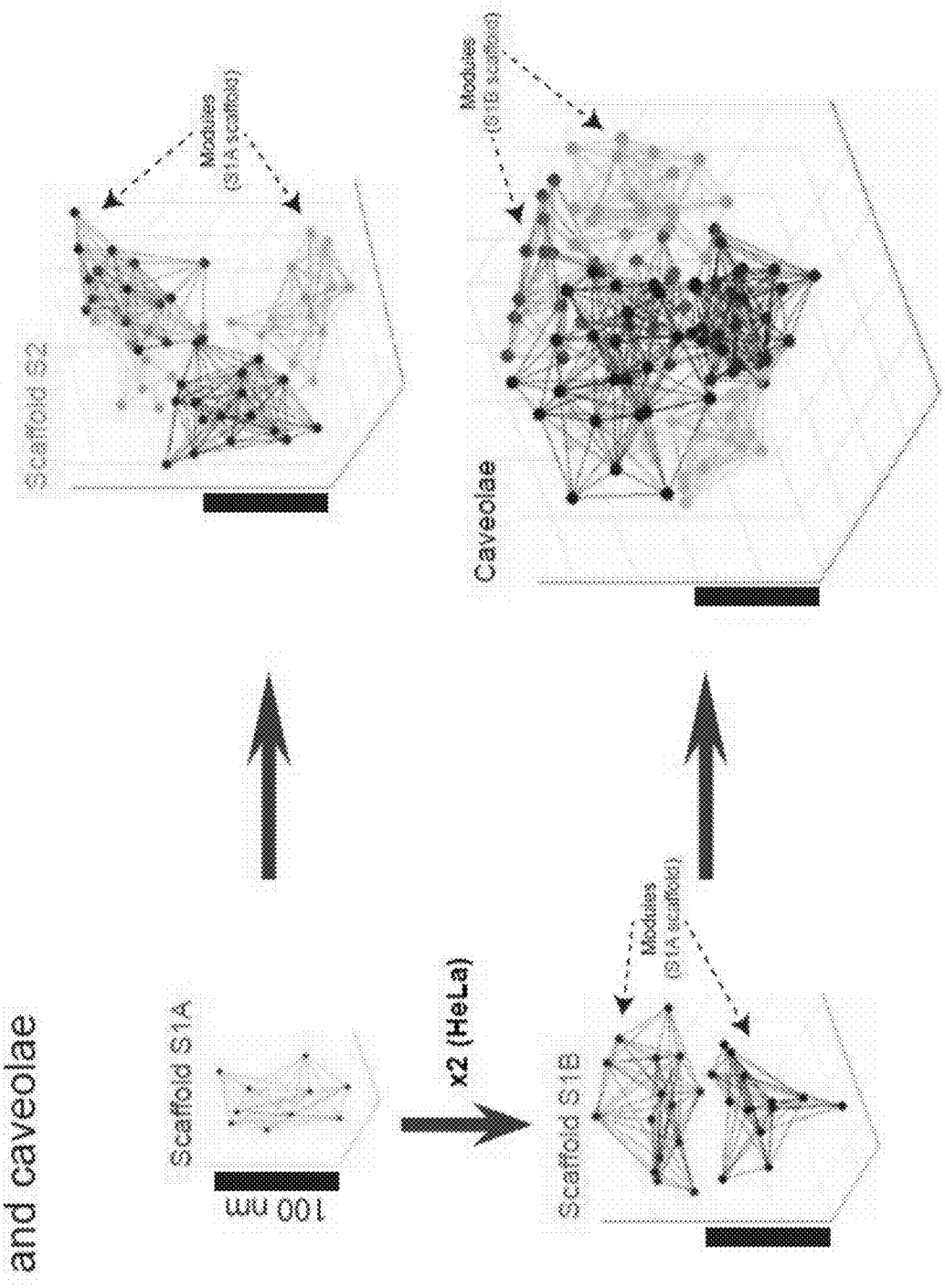

C

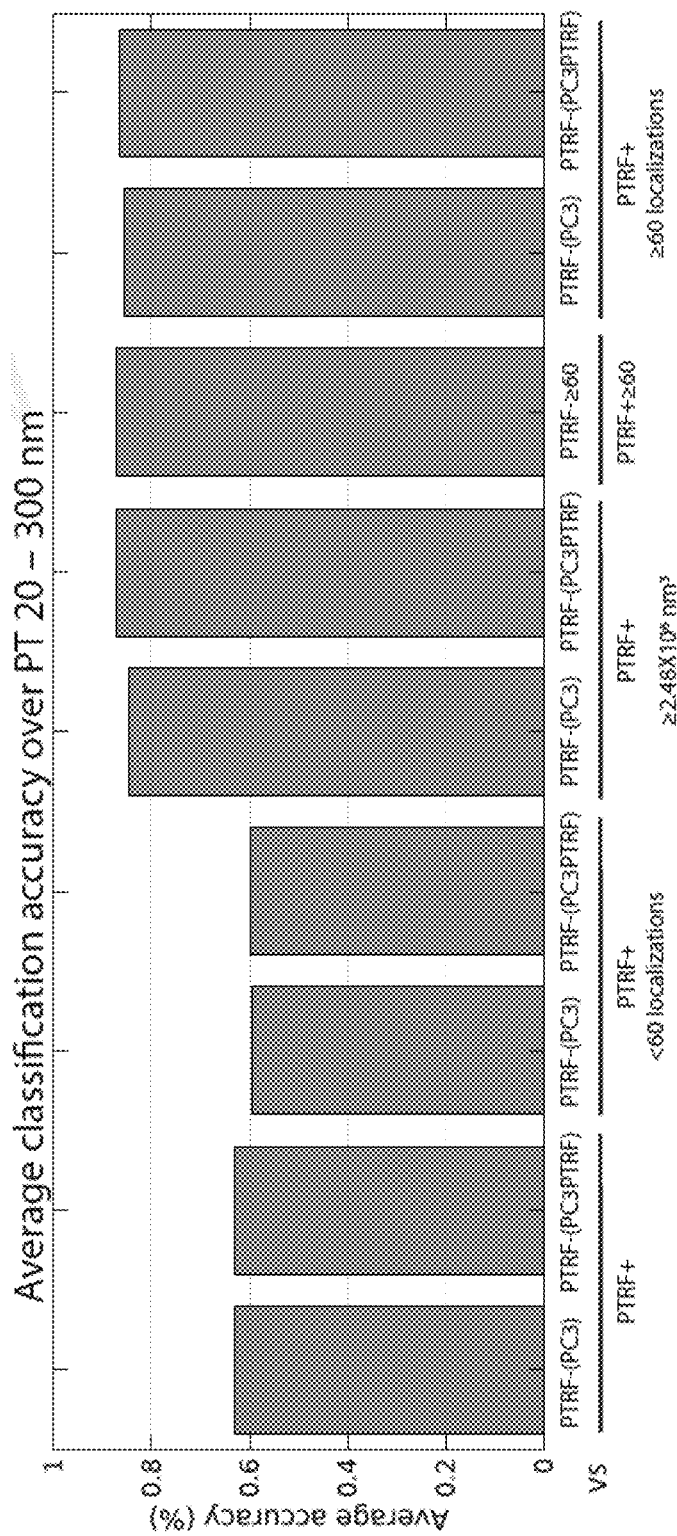

METHODS FOR ANALYSIS OF SINGLE MOLECULE LOCALIZATION MICROSCOPY TO DEFINE MOLECULAR ARCHITECTURE

FIELD OF THE INVENTION

This invention pertains to the field of super-resolution microscopy and in particular, to methods for analysis of single molecule localization microscopy to define molecular architecture.

BACKGROUND OF THE INVENTION

Understanding the structure of macromolecular complexes is critical to understanding the function of subcellular structures and organelles. Mutations in protein folding and trafficking resulting in defective macromolecular complexes and/or macromolecule location within subcellular structures and organelles have been observed in diseases including cystic fibrosis and inherited kidney diseases. Pharmacological chaperones are a promising therapeutic strategy for the treatment of a number of diseases including cystic fibrosis, Alzheimer's disease, inherited glaucoma amongst others.

X ray crystallography and nuclear magnetic resonance spectroscopy report on protein structure at the atomic level; recent technical advances in cryoelectron microscopy have enabled structural visualization of macromolecular biological complexes at near atomic resolution (Fernandez-Leiro and Scheres, 2016). While fluorescence microscopy has been extensively used to study subcellular structures and organelles, its application to structural analysis of macromolecular complexes has been restricted by the diffraction limit of visible light (~200-250 nm). Super-resolution microscopy has broken the diffraction barrier and, of the various super-resolution approaches, the best resolution is obtained using single molecule localization microscopy (SMLM). Based on the repeated activation (blinking) of small numbers of discrete fluorophores (using, for instance, PALM, dSTORM or GSDIM), the precise localization of the fluorophore is determined using a Gaussian fit of the point spread function (PSF), SMLM provides ~20 nm X-Y (lateral) resolution and, with the addition of an astigmatic cylindrical lens into the light path, ~40-50 nm Z (axial) resolution (Foiling et al., 2008; Huang et al., 2008).

Development of analytical tools to interpret the point distributions generated by SMLM is in its infancy. Surface reconstruction and density plots of 3D super-resolution data assume idealistic, noise-free setting and lack quantification (El Beheiry and Dahan, 2013). Ripley's K, L, and H-functions and univariate/bivariate Getis and Franklin local point pattern analysis have been used to analyze super-resolution data for different applications (Lillemeier et al., 2010; Owen et al., 2010; Pereira et al., 2012; Pageon et al., 2013; Rossy et al., 2013; Rossy et al., 2014; Lagache et al., 2015). While useful for global cluster analysis, these second-order statistics have limited ability to deal with localized shape and size properties of homogenous clusters. Moreover, calculating the Ripley's function is computationally intensive making it impractical for handling millions of points (Levet et al., 2015). It is also known that Ripley's function underestimates the number of neighbors for points near the boundary of the 2D or 3D study area (known as the edge effect) (Goreaud and Pélissier, 1999). Several correction methods were proposed to solve the edge effect problem but at the expense of even further increase in computational complexity making it unfeasible to scale to SMLM big-data. Density based methods (e.g. DBSCAN, OPTICS) and Bayesian approach combined with Ripley's functions (Caetano et al., 2015; Rubin-Delanchy et al., 2015) retain the inability to deal with varying cluster densities and sensitivity to prior settings and noisy events. DBSCAN has several parameters that must be carefully set and its runtime scales quadratically with the number of points (e.g. for SMLM data, DBSCAN can take several hours to run) (Mazouchi and Milstein, 2016). Voronoi tessellation depends on Voronoi cell areas to segment clusters and has limited multiscale capability (Levet et al., 2015; Andronov et al., 2016).

Accordingly, there is a need for additional analytical tools to facilitate the study of underlying molecular architecture of diffraction limited cellular structure using SMLM.

There is a further need for additional analytical tools for drug discovery and precision medicine including tools to assess changes in molecular architecture in response to treatment of cells with candidate molecules and tools to assess drug distribution in nanostructured carriers including lipid carriers.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods for analysis of single molecule localization microscopy to define molecular architecture.

In accordance with an aspect of the present invention, there is provided a method of super-resolution microscopy, the method comprising mapping three-dimensional location of each single emission event ("blink") in a plurality of single emission events ("blinks") from a series of optical images of a sample to create a point cloud; and refining the point cloud.

In accordance with an aspect of the present invention, there is provided a computer implemented method of analysis of super-resolution microscopy, the method comprising mapping three-dimensional location of each single emission event ("blink") in a plurality of single emission events ("blinks") from a series of optical images of a sample to create a point cloud; and refining the point cloud.

In some embodiments, refining or filtering of the point cloud comprises iterative steps. Refining or filtering of the point cloud can comprise one or more of a) merging two or more single emission events (blinks); b) removing one or more single emission events (blinks), and c) adding one or more single emission events. Optionally, filtering is globally or regionally applied.

In some embodiments, the filtering step comprises removing non-biological networks from the point cloud, wherein optionally non-biological networks are distinguished from biological networks in a point cloud by performing a multi-scale (varying proximity thresholds) network analysis of the point cloud and determining the network degree distribution for each proximity threshold.

In accordance with another aspect of the invention, there is provided a method of super-resolution microscopy, the method comprising mapping the three-dimensional location of each single emission event in a plurality of single emission events (blinks) from a series of optical images of a sample to create a point cloud; refining the point cloud; identifying clusters within the point cloud and characterizing the individual clusters.

In some embodiments, cluster characterization comprises determining geometrical, topological, and/or physical properties, such as the shape, size, distribution of the single emission events (blinks), and/or hollowness of the individual cluster.

In accordance with another aspect of the invention, there is provided a method of super-resolution microscopy, the method comprising mapping three-dimensional location of each single emission event (blink) in a plurality of single emission events (blinks) from a series of optical images of a sample to create a point cloud; and refining the point cloud by merging two or more single emission events (blinks) into a node based on a merge criteria to create a merged point cloud, optionally the merge criteria is distance between points such that points within a specified distance are merged.

In accordance with another aspect of the invention, there is provided a non-transitory computer readable medium containing program instructions executable by a processor, the computer readable medium comprising program instructions to implement a method of the invention.

In accordance with some embodiments, the methods comprise machine learning.

In accordance with another aspect of the invention, there is provided a method of identifying assessing a candidate drug, the method comprising comparing molecular architecture of a control sample and a sample treated with a candidate drug using the method of super-resolution microscopy.

BRIEF DESCRIPTION OF THE DRAWINGS

These and other features of the invention will become more apparent in the following detailed description in which reference is made to the appended drawings.

The sixth column shows the histograms of the network measure of the cells compared with the network measures of the random graphs.

Figures 10B, 10C:
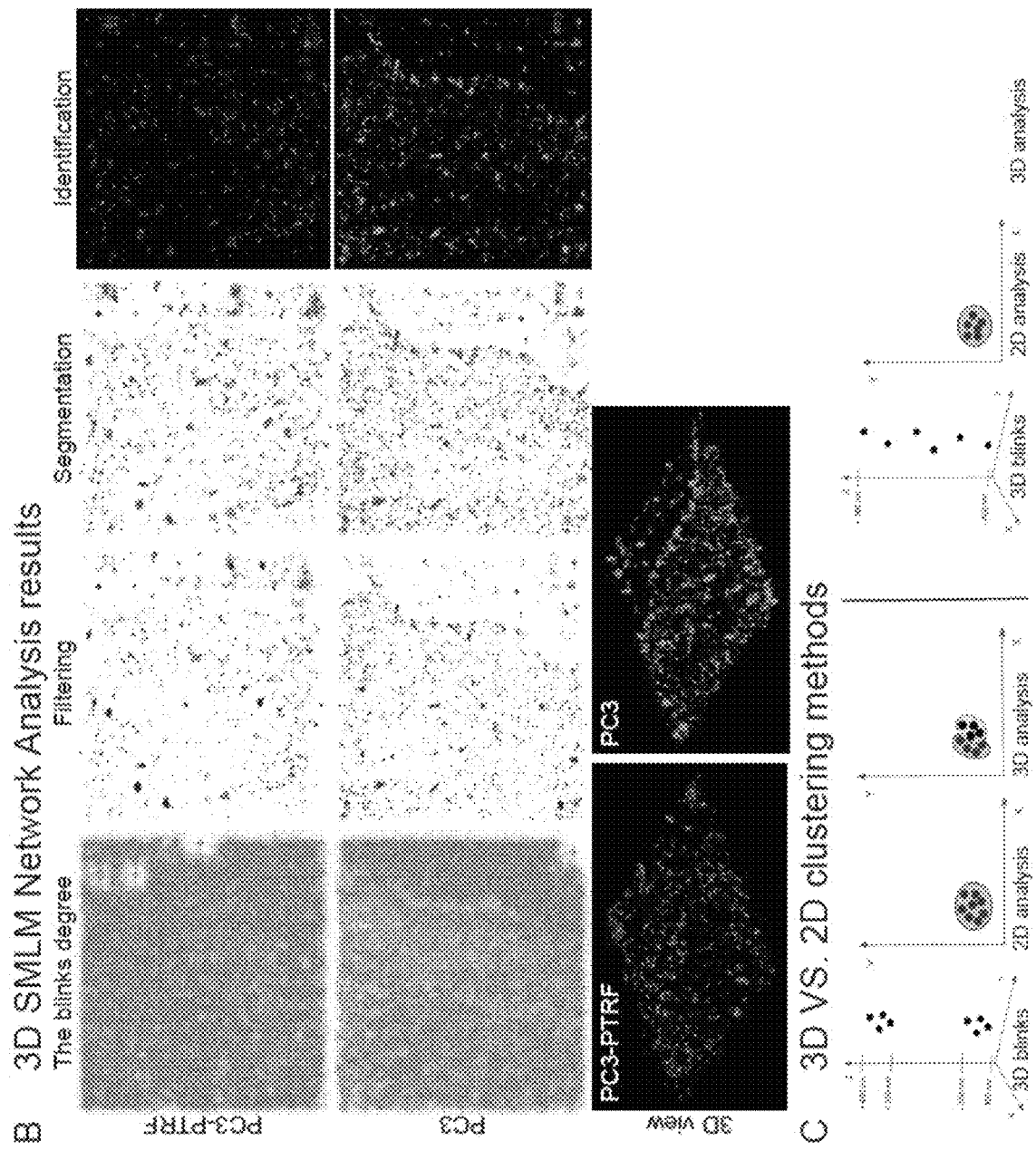

FIG. 10. Comparison between 3D SMLM Network Analysis and 2D SR-Tesseler using the same SMLM dataset after applying iterative blink merging. A. Applying SR-Tesseler to PC3 and PC3-PTRF cell SMLM data sets to retrieve clusters. SR-Tesseler is only applicable for 2D data and extracts 4025 clusters from PC3-PTRF and 4299 from PC3 cells (Table S3). B. Application of the 3D SMLM Network Analysis to the same cells extracts 1106 clusters from PC3-PTRF and 1782 clusters from PC3 cells. C. A schematic depicts how 3D clustering methods is capable of extracting clusters at different Z dimensions while the 2D methods retrieve fake clusters. Moreover, 2D methods may retrieve non-clustered blinks along the Z dimension as clusters while 3D SMLM Network Analysis considers these as noisy blinks and filters them out. This may explain why SR-Tesseler retrieved larger number of clusters. Table S3 shows a comparison between both methods when applied to the same cells.

Figure 11A:
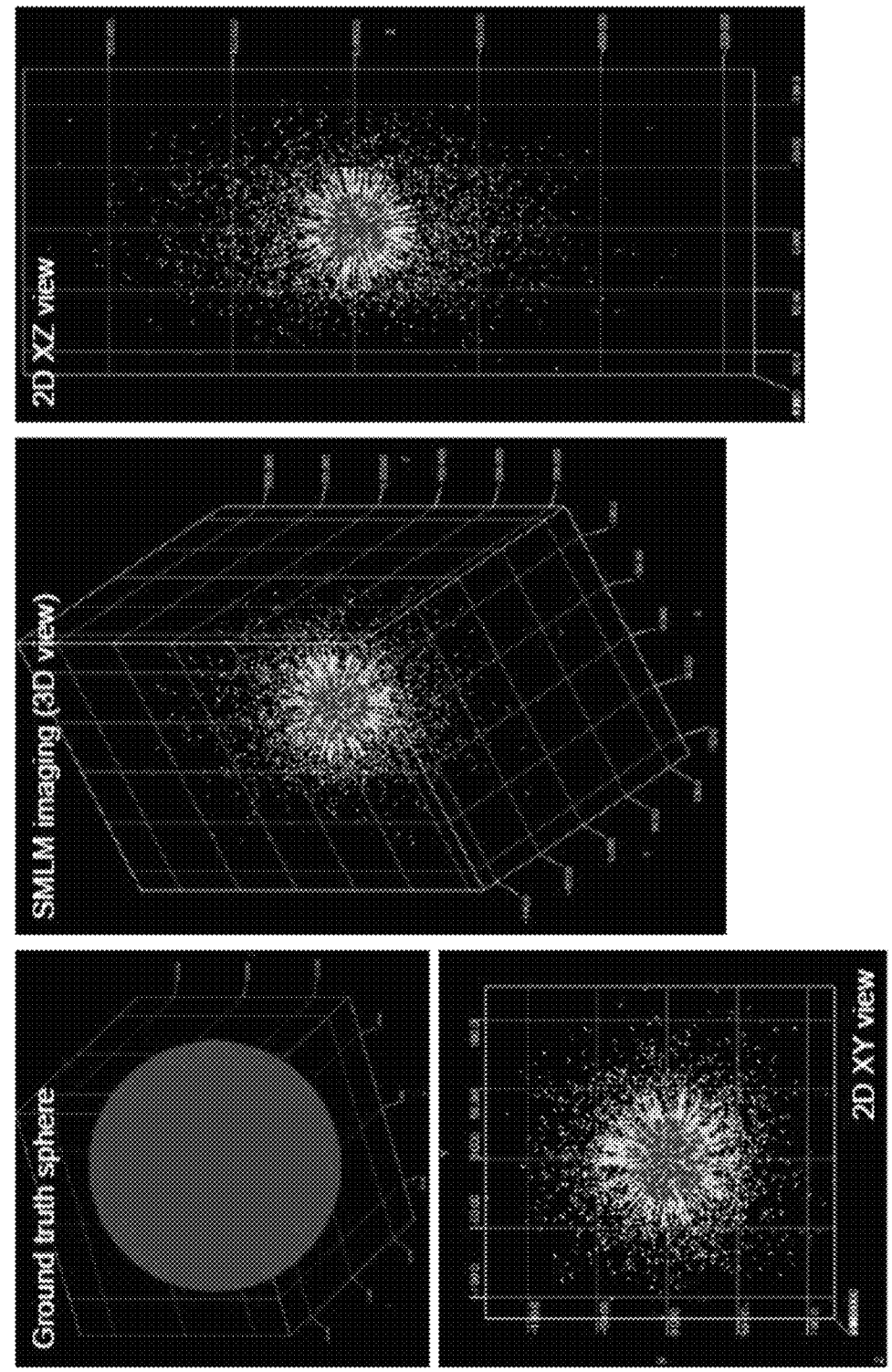

FIG. 11. Network analysis of a simulated 60 nm sphere using SuReSim software. A. A ground truth sphere that mimics caveolae-like structures with 60 nm diameter appears in red was used to obtain an SMLM event list using SuReSim software (Venkataramani et al., 2016). Similar structural, labeling, and acquisition parameters to those used to image Cav1-labeled PC3 and PC3-PTRF cells was used. The yellow bars represent the epitopes and the white points the acquired blinks. In the SuReSim software simulation, the lateral precision (XY) was set to be 20 nm and the axial precision (Z) was set to be 50 nm and the epitope density was set to be 0.1318 $nm^{-2}$ to match the reported 145 Cav1 molecules per caveolae (Pelkmans and Zerial, 2005). 3D and 2D views of the imaged point clouds show increased Z spread, reflecting the poorer Z resolution relative to XY resolution. B. Analysis of biological signatures of the simulated SMLM data of a 60 nm sphere relative to the real SMLM-imaged caveolae. The simulated data was analyzed using the same pipeline (FIG. 2C) used to analyze the real data. The network degree for the blinks was calculated before merging then preprocessed the data by merging the blinks at 20 nm and, then, filtered out the noisy blinks. The resultant point clouds are shown in 3D and 2D views. The dimensions of the point clouds are similar to the bio-signatures of the caveolae blobs that we obtained for real data (FIG. 8C and FIG. 7A-D).

FIG. 12. 3D SMLM Network Analysis of the HeLa cell dataset. A. 3D point clouds of Cav1 of a representative HeLa cell imaged with drift-corrected dSTORM (Tafteh et al., 2016a; Tafteh et al., 2016b) before (green) and after (red) iterative blink merging and filtering out noisy localizations. Color-coded representations of blobs after segmentation and after identification by machine learning using 3*D SMLM Network Analysis* (Khater et al., 2018) pipeline are shown. We identified four groups of blobs representing different Cav1 domains in HeLa cells. B. Matching HeLa Cav1 groups with the previously identified Cav1 domains in PC3 and PC3-PTRF (Khater et al., 2018). The numbers are the Euclidean distances between the groups that capture the dissimilarity. We matched learned groups from PC3-PTRF and HeLa cells and show distances among the feature vector of group centers and present color matching of HeLa groups with previously identified P1 and P2 Cav1 domains in PC3 cells and PP1, PP2, PP3, and PP4 Cav1 domains in PC3-PTRF cells (Khater et al., 2018). C. Distribution of the matched groups from HeLa, PC3-PTRF and PC3 datasets are presented for comparison.

FIG. 13. MPT tuning does not impact blob identification. A. Biological signatures of HeLa Cav1 blobs at different MPTs (10-20 nm) were obtained by 3D SMLM Network Analysis (Khater et al., 2018). We learn 4 groups and show that the only feature affected by MPT tuning is number of localizations. Error bars represent the standard deviation. B. Signatures of matched groups from HeLa, PC3 and PC3-PTRF cells show a high degree of correspondence of the individual group features.

FIG. 14. Modularity analysis of Cav1 blobs. A. Multi-threshold modularity analysis shows the number of connected components, number of modules and localizations per module (at 19 nm MPT) for HeLa blobs at different proximity thresholds. B. Representative blobs from the different HeLa Cav1 domains are shown. Visualization shows the blob's localizations, the localizations' connections, and the blob's modules.

FIG. 15. Module-blob matching between Cav1 domains. A. Signatures of Cav1 blobs and blob modules shows that some module features are similar to blob features. For example, the right bars that represent the caveolae modules (blue) are very similar to the left bars that represent the S1B blobs (magenta). B. We extracted 28 features (e.g. shape, topology, hollowness, network . . . ) for every blob and module. The table encodes the module-blob similarity between the different Cav1 domains (blobs) and the modules of each type as Euclidean distances between every pair of group centres.

FIG. 16. Modular interaction of Cav1 S1A scaffolds forms larger scaffolds and caveolae. Based on the module-blob matching results (FIG. 4B), S1A blobs are stable primitive structures (simplex) that are used to build up more complex S1B and S2 scaffolds. S1B scaffolds are used to build the caveolae coat complex (see Video S1). The figure also shows the hemispherical shape of S2 blobs and the hollow caveolae blobs.

FIG. 17. SMLM Cav1 blob identification via graphlet analysis. A. The proposed analysis framework. Caveolin-1 (Cav1) protein is labeled in PC3 and PC3-PTRF prostate cancer cells. The SMLM events are then represented as a 3D point cloud of Cav1 blinks and 3D SMLM Network Analysis (Example 1) used for cluster analysis of the labeled Cav1 proteins, including modules to correct for multiple blinking of single fluorophores, filtering, segmenting, and identifying the blobs using unsupervised learning (Example 1). The wide-field PTRF mask was also used to classify the Cav1 blobs for the supervised learning task. Graphlet features were extracted for every blob network at various proximity thresholds (PTs). Parallel graphlet decomposition library (Ahmed et al., 2015) was used to extract the feature vector for every network. The feature vectors from all the blobs were used for machine learning classification and identifying biosignatures for the different Cav1 structures. B. The process of getting the graphlet features for a single blob. A network is constructed for the 3D point cloud of a single blob. The graphlets are then counted in every network. The graphlet frequency distribution GFD features are then derived from the connected and disconnected patterns for k=4 nodes. There are connected graphlets (g41, g42, g43, g44, g45, g46) and disconnected graphlets (g47, g48, g49, g410, g411). The GFD features can be extracted for the connected graphlets alone, the disconnected graphlets alone, and for both the connected and disconnected graphlets. C. 3D views of a PC3-PTRF cell showing all the Cav1 blobs, showing PTRF+ Cav1 blobs touching the PTRF mask (blue) with the rest of the blobs labeled as PTRF− (green), showing blobs based on unsupervised learning to assign groups as PP1, PP2, PP3 and PP4 blobs (Example 1). D. Percentages of blobs for each group inside and outside the PTRF mask and distribution of blobs within and without the PTRF mask are shown.

FIG. 18. Graphlet biosignatures for the Cav1 domains via machine learning. A. GFD features of PP1, PP2, PP3 and PP4 blobs extracted using the 3D SMLM Network Analysis pipeline. Histograms of the connected and disconnected GFD features extracted from the networks at a proximity threshold of 80 nm are shown. t-SNE visualization of the GFD features shows a 2D view of the projected features that depicts how the blobs from different classes are distributed. B. Machine learning classification of the four groups using the GFD features extracted at various proximity thresholds (PTs). In the classification task, the one-versus-one (o-v-o) strategy was used for the four groups multi-labeled data to classify the blobs with four classes. In total, there are six classifiers that show all the pairs of groups of classification results. The binary classification shows the performance of classifying every group against the other groups at various PTs. The classification results are shown for the binary classification task byreporting the accuracy (Acc), sensitivity (Sen), specificity (Spe), and area under ROC curve (AUC).

Figure 19A:
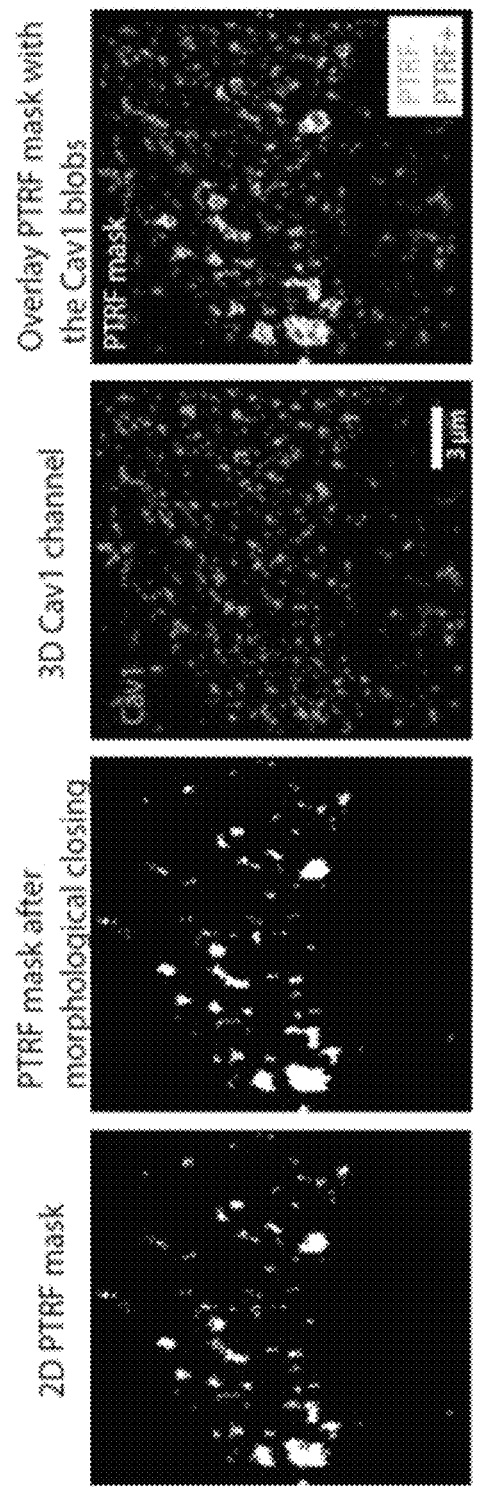
Figure 19B:
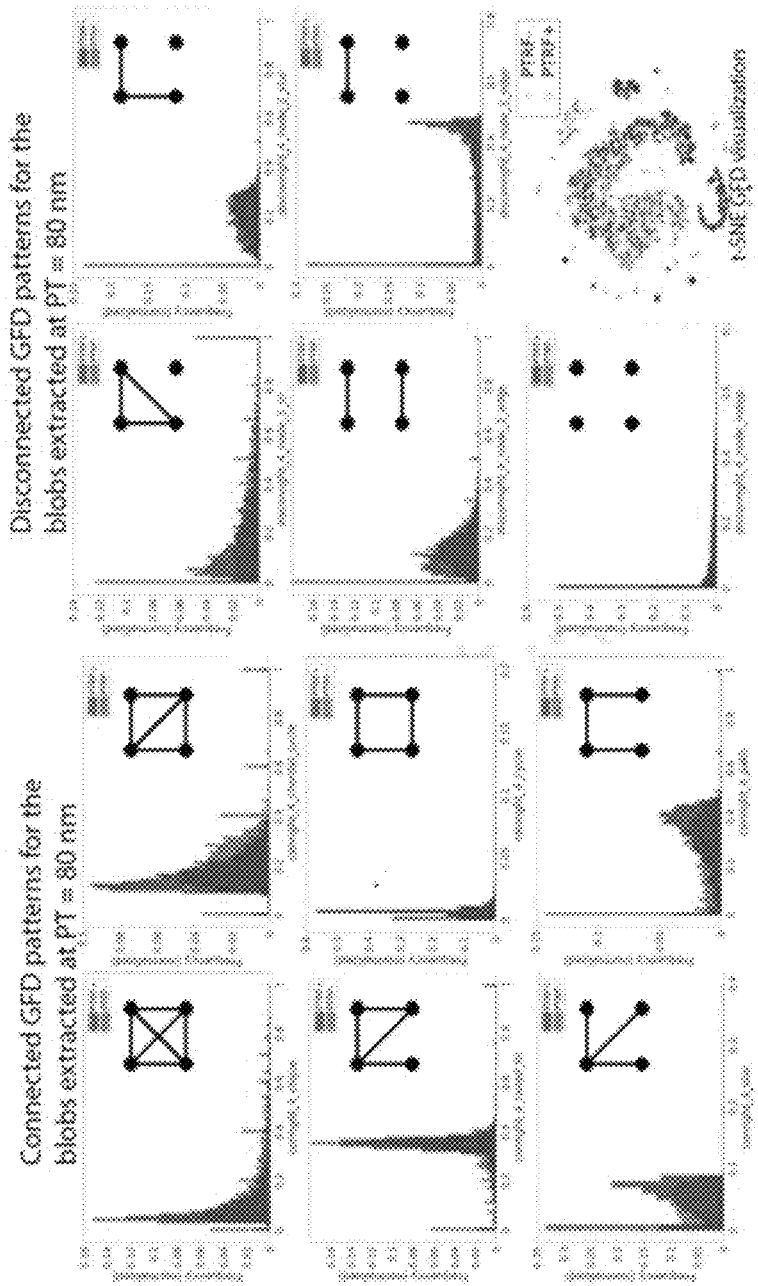
Figure 19C:
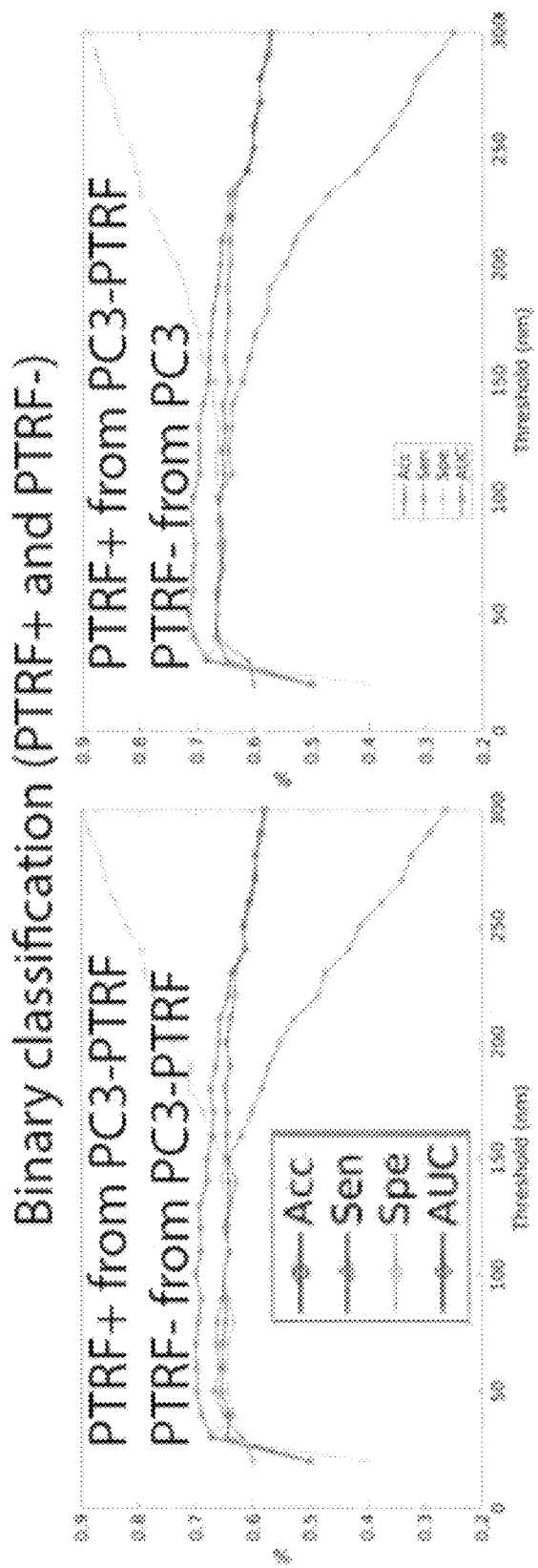

FIG. 19. Classification results using GFD features at various proximity thresholds for PTRF+ and PTRF− blobs. A. A wide-field PTRF/CAVIN1 mask (white) is used to label blobs as CAVIN1-positive (PTRF+) or CAVIN1-negative (PTRF−) (supervised labeling) or to assign the learned and matched groups as PP1, PP2, PP3 and PP4 blobs (unsupervised labeling) as in FIG. 17C. B. GFD features for the blobs when using the PTRF mask to label the blobs into PTRF+ and PTRF−. We showed the histograms of the connected and disconnected GFD features extracted from the networks at a proximity threshold of 80 nm. t-SNE visualization of the GFD features shows that the blobs are not well separated when using the PTRF mask to label the blobs. C. We used the PTRF mask to label the blobs as PTRF+ and PTRF− then after extracting the GFD features applied the machine learning classification. We show the classification results for the binary classification task by reporting the accuracy (Acc), sensitivity (Sen), specificity (Spe), and area under ROC curve (AUC).

FIG. 20. Application of other learned features (# localizations, volume) to improve blob identification using the PTRF mask. A. The volume and number of localizations for the blobs labeled using the unsupervised labeling method. The linear relationship (with 94% correlation) between the volume and # localizations features shows that either can be used along with PTRF mask to identify PTRF+ blobs. B. Using the PTRF mask to farther label the PTRF+ blobs, based on either # localizations (PTRF+≥60 and PTRF+<60) or volume (PTRF+≥2.48×10$^6$ nm$^3$ and PTRF+<2.48×106 nm3) and then, extracting GFD features for machine learning classification to automatically classify the blobs at various PTs. C. The bar plot shows the average classification accuracy of the blobs over the used PTs for the binary classifiers in (B) above. The # localizations and volume cut-offs improves blob identification.

Figure 21A:
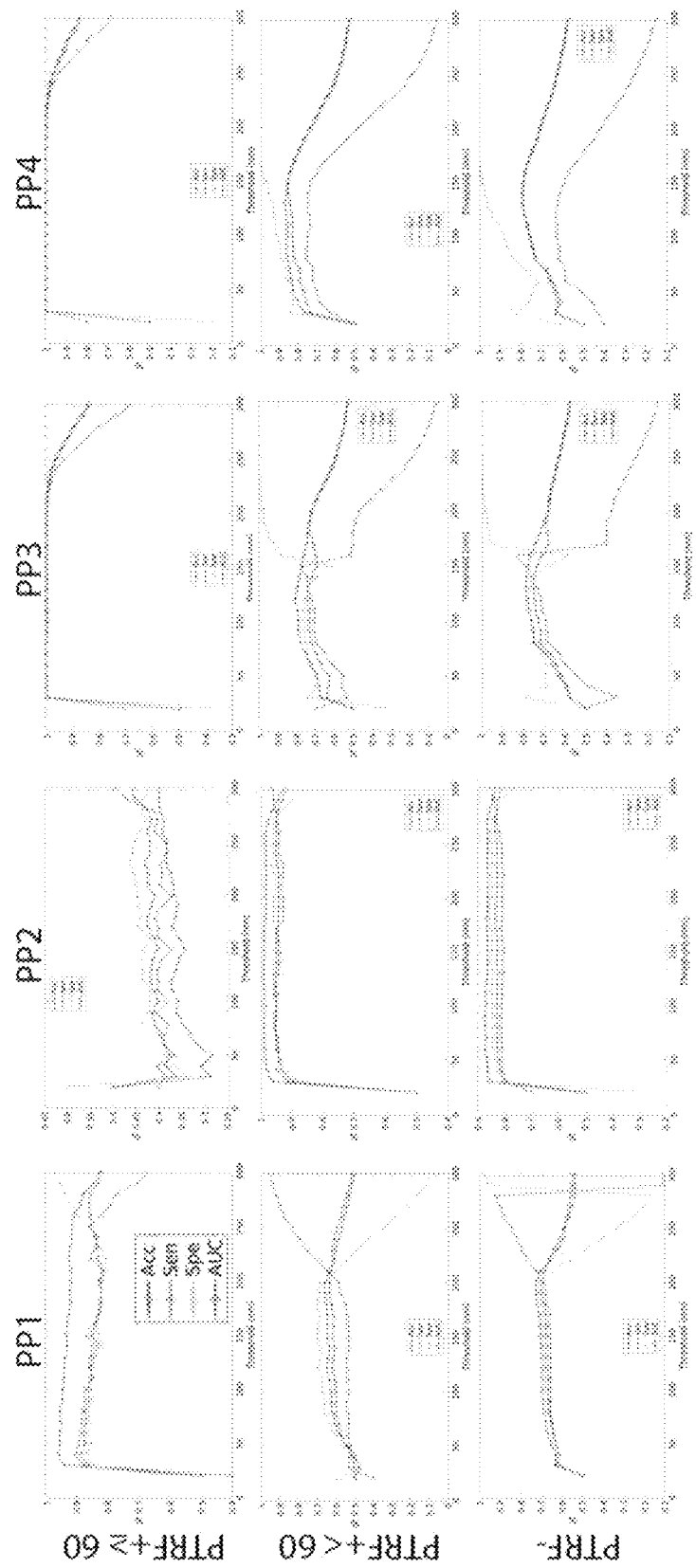
Figure 21B:
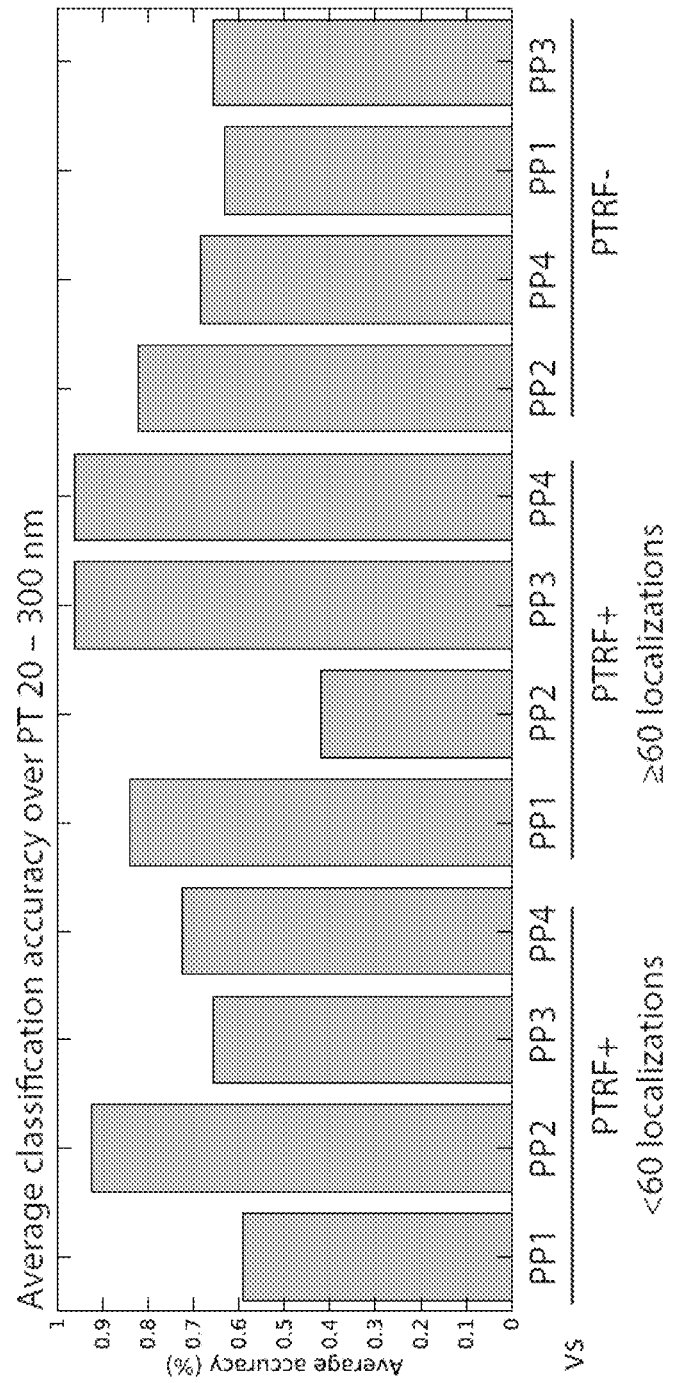
Figures 21C, 21D:
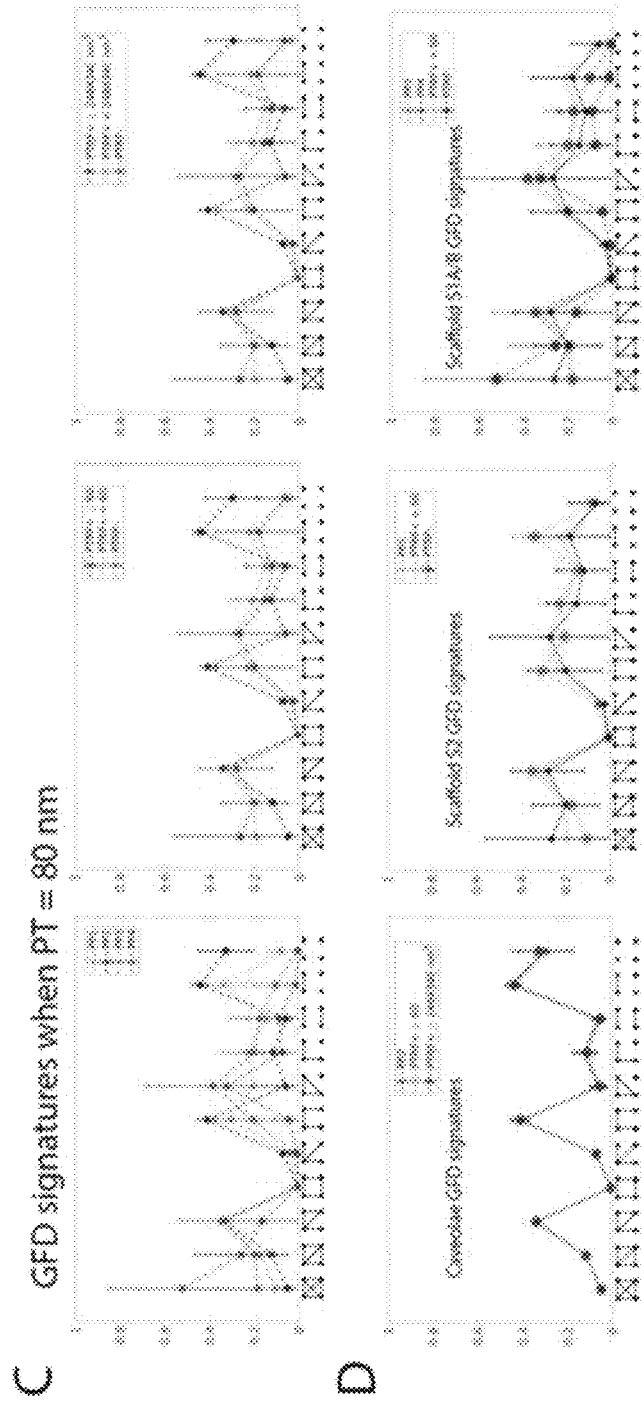

FIG. 21. Using GFD biosignatures for machine learning classification of the Cav1 blobs. A. Identifying the Cav1 domains via classification of all combinations of blob groups using unsupervised learning based blob labels {PP1, PP2, PP3, PP4} or PTRF mask based supervised learning {PTRF+≥60, PTRF+<60, PTRF−}. The classification results show the similar and dissimilar groups based on the extracted GFD features at various PTs. For example, PP2 and PTRF+≥60 are very similar and they represent the same group of Cav1 domains (i.e. caveolae). The low classification accuracy suggests that the GFD features of these two groups are very similar. B. The bar plot shows the average classification accuracy of the blobs over the used PTs for the binary classifiers in (A) above. C. GFD signatures for the blobs at PT 80 nm using the different labeling methods. It shows that using either # localizations or volume cut-offs to label the PTRF+ blobs will lead to almost the same GFD biosignatures. D. Depicting the GFD biosignatures for the blobs from the various groups shows that the similar Cav1 domains have similar feature trends. For example, PP2 blobs almost have identical features to the PTRF+≥60 and PTRF+ ≥2.48×106 nm3 and correspond to caveolae. The trend of GFD features represents a biosignature for each Cav1 domain.

FIG. 22. GFD discriminatory features for the different Cav1 blobs over various proximity thresholds. The change in GFD features over the various proximity thresholds using two different labeling strategies for the Cav1 blobs. The mean and standard deviation of the (A) connected and (B) disconnected features have different values based on the used PT. Some of the GFD features are not informative at all and stay unchanged along with the different values of the PTs (e.g. g44). Some of the features show that the similar groups have the same trends over the different PTs (e.g. PTRF− and PTRF+<60).

DETAILED DESCRIPTION OF THE INVENTION

Definitions

Unless defined otherwise, all technical and scientific terms used herein have the same meaning as commonly understood by one of ordinary skill in the art to which this invention belongs.

As used herein interchangeably, the terms "single emission event" and "blink", refer to the light energy emitted by a single fluorophore as defined by single molecule fluorescence microscope.

As used herein interchangeably, the terms "cluster" and "blob", refer to a group of single emission events or blinks or to a group of molecular localizations following merging of emission events.

As used herein, the term merge includes combining n single emission events into less than n single emission events and can include replacing n single emission events with less than n single emission events.

Overview

This invention provides methods, and systems for super-resolution microscopy. The invention also provides computer-implemented methods of analyzing super-resolution microscopy and/or super-resolution data. Using the invention, the molecular architecture of sub-diffraction limited cellular structures can be assessed in their native environment. In some embodiments, the invention facilitates the comparison of test and control samples and allows for the identifications of changes in cellular structure between different samples. Accordingly, such embodiments may be useful in assessing cellular structure modifications due to genetic changes and/or disease progression. The methods and systems of the invention can also be used to assess sub-diffraction limited structure of non-cellular systems and/or isolated cellular components and/or modules and/or subdomains including, for example chloroplast and mitochondria, ribosome, chromatin, chromosomes, cilia, microtubules, nuclear localization of transcription factors, and flagella and/or viral particles as well as the structure of macromolecular complexes including, but not limited to, membrane receptors, signaling complexes, RNA bodies, DNA, lipid domains, protein-protein interactions and the interaction of proteins with other molecules including receptor-ligand interactions.

Figure 1:
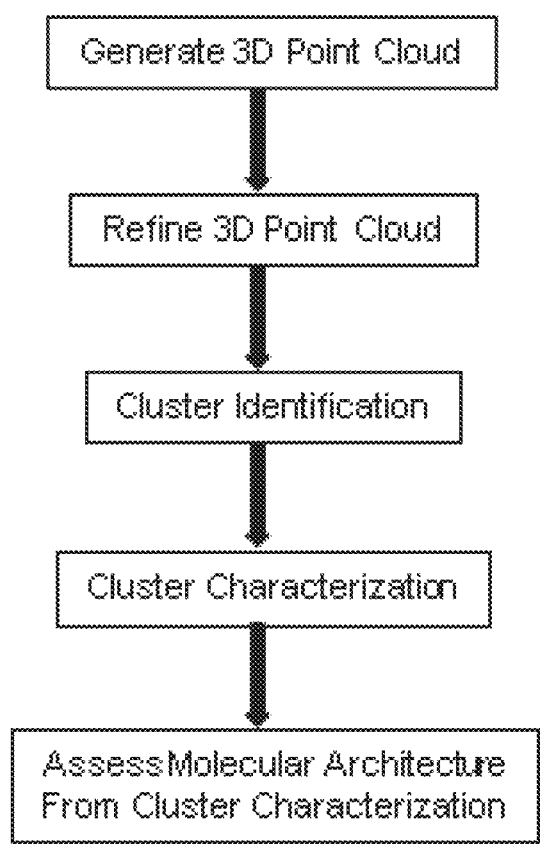
FIG. 1 is a flow chart illustrating the steps of computational network analysis for SMLM in one embodiment where the single emission event list (also called blinks) is converted to a three-dimensional (3D) point cloud. The 3D point cloud is filtered or refined. Clusters are identified and characterized from the filtered 3D point cloud. The underlying molecular architecture is assessed based on the characterization of the identified clusters.

Referring to FIG. 1, the methods and systems for super-resolution microscopy map single emission events (blinks) from fluorophores in three-dimensions to create a point cloud. The resulting point cloud is then refined or filtered. Clusters are identified in the refined or filtered point cloud and optionally characterized. In some embodiments, characterization of the clusters includes machine-learning based classification of clusters. The methods of the invention can be modified to allow prior knowledge of the molecular architecture to inform the refinement or filtering of the point cloud and/or cluster characterization including machine-learning based classification. In some embodiments, the methods of the invention are modified to allow cluster characterization based on the comparison between samples containing a specific structure and samples lacking the structure. Optionally, comparison between samples containing the structure and samples lacking the structure is used to validate the machine-learning based classification of clusters.

From cluster characterization the molecular architecture or structure is assessed optionally in view of pre-existing knowledge of the biology.

Appropriate fluorophores for use with the invention are known in the art and include fluorescent proteins or peptides or fusions thereof, for example GFP, YFP and RFP or photoactivatable tandem dimer Eos or monomeric Eos2; organic fluorophores that may be used to tag or label antibodies, aptamers or other binding molecules. In some embodiments, fluorescent dyes that interact directly with the target molecule may be used and include, for example, DNA dyes such as Vybrant® DyeCycle. The approach can be applied to any fluorophore used for any method of single molecule localization microscopy, including but not limited to N-STORM, dSTORM, PALM, iPALM. In some embodiments, the methods are modified to be used with more than one fluorophores where different fluorophores are used to tag different molecules either directly or via binding molecule.

SMLM imaging may be conducted as is known in the art. Optionally, each image may be subdivided into smaller regions of interest (ROIs) to facilitate processing.

Refining/Filtering the Point Cloud:

Refining/filtering of the point cloud includes assessing single emission events (blinks) within the point cloud to determine if they originate from the same labelled molecule and removing duplicates. In some embodiments, refining or filtering of the point cloud comprises removing one or more single emission events (blinks) from the point cloud, merging N single emission events (blinks) or replacing N single emission events (blinks) with M single emission event (blinks) where M is less than N, for example two single emission events (blinks) can be merged into one single emission events (blinks) or three or more single emission events (blinks) can be merged into two or into one.

Merging of two or more single emission events (blinks) is optionally based on proximity with crisp or fuzzy proximity threshold. In embodiments where merging is not based on a crisp threshold, the filter may be configured such that merge likelihood is higher as the distance between single emission events (blinks) is smaller. Optionally proximity threshold can be assessed in two or three dimensions. In some embodiments, the proximity of single emissions (blinks) to merge is a distance less than a threshold distance.

In some embodiments, the threshold changes across different regions and/or across different datasets.

In some embodiments, the threshold changes across different dimensions (i.e. X, Y versus Z).

Refinement or filtering of the point cloud can be completed on globally, regionally or on an event basis or combination thereof. Individual refinement or filtering steps can be completed on a global or regional basis, for example the filtering step is the same everywhere or is different in different regions. In some embodiments, some filtering steps may be global filtering steps while other filtering steps are regional. Alternatively, all filtering steps are either global or regional.

Filtering or refinement steps can be iterative or completed in a single step. For example, in iterative filtering, multiple rounds of merging are applied where all points are assessed against merging criteria and if criteria is satisfied the point (or points) is (are) merged with another point (or points). These steps are optionally repeated until no points meet the merge criteria. Merge criteria can be based on data-driven cues and/or prior knowledge. Merge criteria can be based on similarity between blinks. Similarity can represent similarity of blinks' spatial location; in this case, merge criteria would be based on proximity in two dimensions or three dimensions between blinks. Merge may be based on information derived from the knowledge about the labelling, antibody properties, photo-kinetics, imaging details, amongst other.

In some embodiments, a first or preliminary filtering step criteria includes a merge threshold based on the resolution limit of the GSD microscopy. In some embodiments, the resolution limit is based on localization precision of the single molecule localization microscope.

In some embodiments, the merge threshold considers differential lateral (XY) vs axial (Z) resolution of single molecule localization microscopes.

In other embodiments, merge threshold is determined based on an analysis of non-biological networks in the point cloud for example, multiple blinks from a single fluorophore may result in a non-biological network nano-cluster. The filtering step removes these non-biological network nano-clusters.

Optionally, non-biological networks are distinguished from biological networks in a point cloud by performing a multi-scale (varying proximity thresholds) network analysis of the point cloud and determining the network degree distribution for each proximity threshold (presented by $T_P$. For each proximity threshold, the number or percentage (represented by N) of nodes in the network with a degree greater than the average network degree is determined. N is then plotted versus $T_P$ to obtain the curve $N(T_P)$. The curve $N(T_P)$ represents the change of blinks' density as the network evolves with increasing scale. As $T_p$ increases beyond the size of the non-biological networks, the nodes with degree greater than the average network degree stabilizes and the curve $N(T_P)$ plateaus. From the curve $N(T_P)$ the threshold which marks the beginning of the plateau is approximated. The plateau represents a saturation phenomenon where the blinks of every molecule get clustered forming a non-biological network nano-cluster and have approximately the same degree. The merge threshold is the threshold that marks the beginning of the plateau is determined using the derivative $dN/T_P$.

In some embodiments, the merge threshold is determined from analysis of multiple individual cells.

In some embodiments, the merge threshold is used to assess non-biological networks from different single molecule localization microscopes.

In some embodiments, the merge threshold is determined for cells labeled with different combinations of primary and secondary antibodies, Fab or Fab2 primary or secondary antibodies, or directly conjugated primary antibodies or Fab or Fab2 or using fluorescent proteins.

Filtering or refinement steps may be additive or progressive wherein a first refinement or filtering step is completed before the next step is completed. Alternatively, filtering or refinement steps can be completed in any order. Filtering may be performed sequentially or in parallel.

For example, in one embodiment single molecule localization microscopy event list data is analyzed and events with a photon content or blink intensity below or above a specified level is filtered out in an initial step. In such an embodiment, a second step the refinement or filtering step could be to replace or merge single emission events within a specified proximity or area (or distance) with a single emission event. In some embodiments, the first filtering step is a merge filtering step. Optionally, the new single emission event is placed at the average or median position of all combined emission events. In some embodiments, the average is a "weighted average", by giving some blinks higher weights than others.

Figure 5:
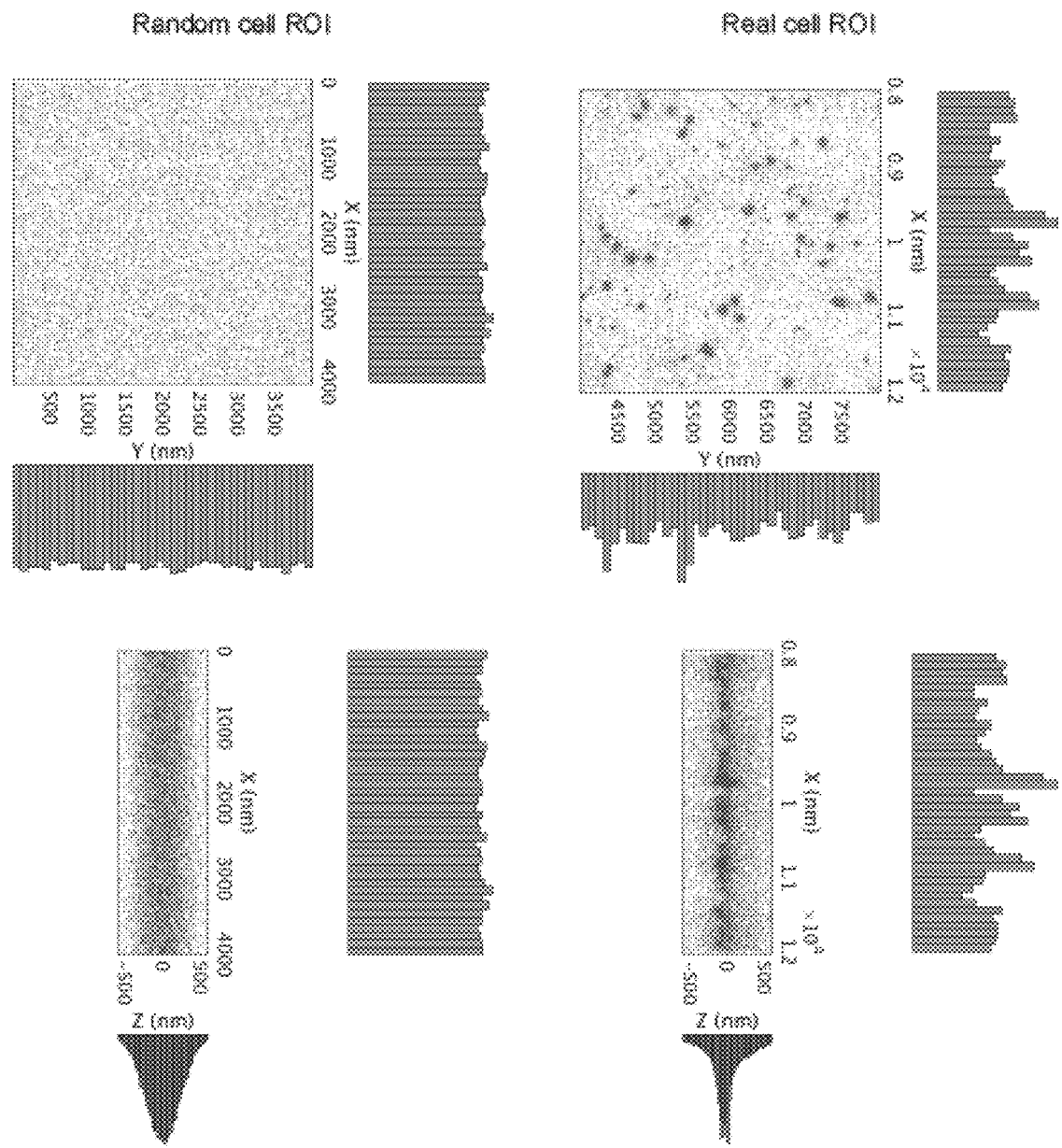
FIG. 5 illustrates the process of generating random blinks for a 3D ROI. Random graphs were effectively used to filter out noisy blinks of the ROIs extracted from the real cells of the datasets. The random blinks were generated with the same distribution of the blinks in the real ROI. The distribution of the blinks was uniformly distributed in X and Y dimensions and normally distributed in the Z dimension.

In some embodiments, the single emission events in the point cloud are assessed for noise-like properties. Noise-like properties may be determined by comparing the single emission events or the point clouds with points obtained from a noisy process or randomly generated points. Referring to FIG. 5, the random points may be generated with the same distribution of the single emission events in the actual dataset. In the illustrated embodiment, the distribution of random points is uniform is in X and Y dimensions and normal in the Z dimension. The distribution of random may be different in other data sets or application and is selected to reflect the distribution of points in the real dataset.

In some embodiments, network analysis comparing the 3D point cloud with those of a random network is used to identify and then, optionally, filter out noisy blinks. Network measures, for example see Table 1, are optionally determined at multiple distance thresholds and compared to network measures from a random network to identify noisy blinks.

TABLE 1

| Network Measure | Description |
| --- | --- |
| Node level measures | |
| wAvgDeg | Average weighted degree measure (node strength) |
| wSTDeg | Standard deviation of the weighted degree |
| wMedDeg | Median weighted degree |
| uwAvgDeg | Average unweighted degree measure |
| uwSTDeg | Standard deviation of the unweighted degree |
| uwMedDeg | Median unweighted degree |
| wAvgCC | Average weighted clustering coefficient |
| wSTCC | Standard deviation of the weighted clustering coefficient |
| wMedCC | Median weighted clustering coefficient |
| wAvgNdeg | Average weighted neighbouring degrees |
| wSTNdeg | Standard deviation of the weighted neighbouring degrees |
| wMedNdeg | Median weighted neighbouring degrees |
| uwAvgNdeg | Average unweighted neighbouring degrees |
| uwSTNdeg | Standard deviation of the unweighted neighbouring degrees |
| uwMedNdeg | Median unweighted neighbouring degrees |
| wAvgEcc | Average weighted eccentricity |
| wSTEcc | Standard deviation of the weighted eccentricity |
| wMedEcc | Median weighted eccentricity |
| uwAvgEcc | Average unweighted eccentricity |
| uwSTEcc | Standard deviation of the unweighted eccentricity |
| uwMedEcc | Median unweighted eccentricity |
| Network level measures | |
| wDen | Weighted network density |
| wDia | Weighted network diameter |
| uwDia | Unweighted network diameter |
| wRad | Weighted network radius |
| uwRad | Unweighted network radius |
| wLambda | The average shortest path length (characteristic path) in the weighted network |
| uwLambda | The average shortest path length (characteristic path) in the unweighted network |
| numConComp | Number of connected components of the undirected network |
| largestConComp | Largest connected components in the undirected network |
| wSmetric | Sum of products of the weighted degrees across all edges |
| uwSmetric | Sum of products of the unweighted degrees across all edges |

In some embodiments, the filtering or refinement step comprises removing non-biological networks from the point cloud. The removal of the non-biological network may be implemented via collapsing the non-biological network into one node or a number of nodes smaller than those in the non-biological network.

In some embodiments, prior knowledge of the labelled target molecule or antibody size or antibody geometry is used to facilitate noise reduction and/or filtering, for example, if it is known in the art that target molecule is localized to a specific cellular structure and/or generally is clustered, filtering may be used to remove single emission events distal from the specific cellular structure and/or non-clustered events. In some embodiments, co-localization of interacting molecules and/or negative controls can be used to filter.

In some embodiments, alternative filtering or refining strategies are compared and the results of the different strategies are evaluated based on some performance measure. In some embodiments, the performance measure is based on prior knowledge of the structure or biology being analyzed.

Clustering:

Clustering of single emission events in the filtered 3D point cloud may be performed by a variety of techniques known in the art, where the selection of the appropriate clustering techniques is dependent on sample being analyzed and the individual data set. Appropriate clustering methods are known in the art and include connectivity-based clustering, centroid-based clustering, distribution-based clustering or density-based clustering.

In some embodiments, clustering includes network analysis of the 3D point cloud and comparison of the network with random networks and/or a control 3D point cloud at one or more distance thresholds. Optionally, multi-threshold analysis comparing the test 3D point cloud network to a randomly generated 3D point cloud network is used to identify a distance threshold that can distinguish between the two networks.

Where available, a comparison between a 3D point cloud network for a sample containing a specific structure and a 3D point cloud network for a sample lacking the structure at multiple distance thresholds is used to determine a threshold that distinguishes the samples.

Prior knowledge of the target molecule or structure of interest may be used to facilitate selection of clustering algorithm and/or parameters and/or validate the results of the clustering. If available, reference data sets or control data sets can be used to facilitate clustering algorithm and/or parameter settings and/or validate clustering results. For example, comparison of cells with and without a specific structure, information with respect to expected number of clusters and/or cluster types may be available. In some embodiments, clusters are validated to confirm that the clusters identified are biologically relevant.

Optionally, identification of clusters or blobs uses a mean shift algorithm. In some embodiments network/graph partitioning algorithms are used to identify clusters.

Cluster Analysis:

Once clusters have been defined, individual clusters may be characterized and/or sorted based on one or more of the assessed characteristics. Clusters may be assessed for geometrical properties (such as size, shape including planar, spherical or linear), topological properties (including hollowness); point distribution measures (e.g. moments); network measures of blobs (e.g. modularity or small-worldness), blobs' locations and relative locations within the sample.

The cluster shape features that may be assessed include fractional anisotropy, linear anisotropy, planar anisotropy, spherical anisotropy, distribution of the point cloud along the X-dimension, distribution of the point cloud along the Y-dimension, distribution of the point cloud along the Z-dimension and ellipsoid volume of the 3D point cloud of the blob.

The cluster hollowness features may be assessed based on the distribution of distances of the nodes to the cluster centroid or to the cluster medial axis or skeleton. Properties of the distribution of distances (including average distances of the nodes to their centroid, maximum distance of the nodes from their centroid, minimum distance of the nodes from their centroid, median distance of the nodes to their centroid and standard deviation of the nodes distances to their centroid) may be used to define hollowness.

The cluster network features that may be assessed include average node degree within the blob, maximum node degree within the blob, minimum node degree within the blob, average clustering coefficient value of the nodes, maximum clustering coefficient value of the nodes, minimum clustering coefficient value of the nodes, transitivity measure of the nodes, characteristic path of the nodes, average eccentricity measure, blob's network/graph radius, blob's network/graph diameter, blob's network/graph density, blob's network/graph modularity measure, average optimized modularity for the blob's network and number of nodes Optionally, clusters are grouped based on one or more characteristics. In some embodiments, similarity analysis is used to classify clusters into the groups.

In some embodiments, machine learning algorithms are used identify cluster groups. Optionally, the methods use an unsupervised learning framework to build the cluster identification model. Optionally, supervised machine learning, which is trained on clusters labelled with known groups, is used to identify groups of clusters in new unlabelled data. Optionally, the machine learning is informed by prior understanding of the biology.

To gain a better understanding of the invention described herein, the following examples are set forth. It will be understood that these examples are intended to describe illustrative embodiments of the invention and are not intended to limit the scope of the invention in any way.

EXAMPLES

Example 1

Introduction

In this example, a 3D point cloud (Botsch et al., 2010; Aldoma et al., 2012; Berger et al., 2014) was used to model SMLM data. Virtual connections between points transform the point cloud into a network modeled computationally as a graph with nodes (or vertices); edges are connections between nodes (points) that weight the distance between nodes. Such network representations have been widely and successfully adopted for analysis of brain, social and computer networks (Barabasi and Oltvai, 2004; Newman, 2010; Baronchelli et al., 2013; Sporns, 2013; Brown et al., 2014). Using machine learning approaches, features that distinguish networks were identified and used to understand the underlying organization or architecture of the network. Here point cloud network analysis was applied to SMLM data sets to define the molecular architecture of plasma membrane associated caveolae and caveolin-1 (Cav1) scaffolds.

Formation of caveolae, 50-100 nm plasma membrane invaginations, requires both the coat protein Cav1 and the adaptor protein polymerase I and transcript release factor (PTRF or CAVIN1) (Hill et al., 2008). Cav1 is also expressed in functional non-caveolar domains, or Cav1 scaffolds, that cannot be distinguished from caveolae by fluorescence microscopy, as both are smaller than the diffraction limit (Lajoie et al., 2009). Metastatic PC3 prostate cancer cells express Cav1 but no CAVIN1 and have no caveolae; stable transfection of CAVIN1 (generating PC3-PTRF cells) induces caveolae (Hill et al., 2008). Application of machine learning to point cloud SMLM network analysis of Cav1 distribution in PC3 and PC3-PTRF prostate cancer cells has now defined Cav1 localization signatures for scaffolds and caveolae.

Materials and Methods

GSD SMLM Imaging

PC3 and PC3-PTRF cells were cultured in RPMI-1640 medium (Thermo-Fisher Scientific Inc.) complemented with 10% fetal bovine serum (FBS, Thermo-Fisher Scientific Inc.) and 2 mM L-Glutamine (Thermo-Fisher Scientific Inc.). All cells were tested for *mycoplasma* using PCR kit (Catalogue # G238; Applied Biomaterial, Vancouver, BC, Canada). Cells were plated on coverslips (NO. 1.5H; coated with fibronectin) for 24 h before fixation. Cells were fixed with 3% paraformaldehyde (PFA) for 15 min at room temperature, rinsed with PBS/CM (phosphate buffered saline complemented with 1 mM $MgCl_2$ and 0.1 mM $CaCl_2$)), permeabilized with 0.2% Triton X-100 in PBS/CM, and blocked with PBS/CM containing 10% goat serum (Sigma-Aldrich Inc.) 1% bovine serum albumin (BSA; Sigma-Aldrich Inc.). Then the cells were incubated with the primary antibody (rabbit anti-caveolin-1; BD Transduction Labs Inc.) for 12 h at 4° C. and with the secondary antibody (Alexa Fluor 647-conjugated goat anti-rabbit; Thermo-Fisher Scientific Inc.) for 1 h at room temperature. The primary and secondary antibodies were diluted in SSC (saline sodium citrate) buffer containing 1% BSA, 2% goat serum and 0.05% Triton X-100. Cells were washed extensively after each antibody incubation with SSC buffer containing 0.05% Triton X-100. Post-fixation was applied using 3% PFA for 15 min followed by extensive washing with PBS/CM.

Before imaging, the imaging buffer was freshly prepared with 10% glucose (Sigma-Aldrich Inc.), 0.5 mg/ml glucose oxidase (Sigma-Aldrich Inc.), 40 µg/mL catalase (Sigma-Aldrich Inc.), 50 mM Tris, 10 mM NaCl and 50 mM β-mercaptoethylamine (MEA; Sigma-Aldrich Inc.) in double distilled water (Huang et al., 2008; Dempsey et al., 2012). The cells were immersed in the imaging buffer and sealed on a glass depression slide.

GSD super-resolution imaging was performed on a Leica SR GSD 3D system using a 160× objective lens (HC PL APO 160×/1.43, oil immersion), a 642 nm laser line and a EMCCD camera (iXon Ultra, Andor). Full laser power was applied to pump the fluorophores to the dark state, and at frame correlation value 25% the imaging program auto-switched to acquisition with 50% laser power. Epi-illumination was applied for the pumping process while a TIRF illumination with 100-nm penetration depth was applied for the acquisition step. The acquisition was done for 5 min with the camera exposure time at 6.43 ms/frame. The event lists were generated using the Leica SR GSD 3D operation software with a detection threshold of 1 photon/pixel, XY pixel size 20 nm, Z pixel size 25 nm and Z acquisition range+/−400 nm.

Computational Methods

Graph Construction

Each image has dimensions of 18×18×1 µm³. For analysis, each image is divided (tiled) into 36 ROIs of 3×3×1 µm³. Each ROI was much greater than subcellular structures. Tiling the cell into ROIs sped up processing time for the whole cell via HPC cluster computer. Locations (X,Y, and Z) of Cav1 event lists generated by Leica GSD analysis software were represented as a point cloud (a set of points in 3D space), a well-established representation used in 3D visual computing (Botsch et al., 2010; Aldoma et al., 2012; Berger et al., 2014). An iterative blink merging algorithm merged blinks within 20 nm of each other, the resolution limit of the GSD approach, removing high degree (high interacting) points (i.e. from the same fluorophore or clusters of fluorophores). Virtual connections constructed between the resulting 3D points transform the Cav1 point cloud into a network modeled computationally as a graph with: nodes (representing a single Cav1 protein); edges (capturing the interaction between pairs of proteins); and weights (encoding the distances between nodes, up to an upper threshold limit). Network measures were calculated at multiple distance thresholds to identify measures that discriminate between caveolae-containing PC3-PTRF and PC3 cells lacking caveolae. With hundreds of thousands to millions of Cav1 localizations (i.e. network nodes), the imaged 3D space was partitioned using equal-sized 3D tiles and distributed parallel computations across many nodes of our HPC clusters. A filtering step retained only the sub-networks of nodes or blobs whose properties are different from those of randomly generated networks (FIG. 5).

Well-established, quantifiable measures can then be extracted from these networks (Clustering Coefficient; Node Density; Connected Components; Degree; Closeness and Betweenness; Small Worldness; etc.) and divided into different classes: (spatially) global vs. local; microscopic (node-level) vs. macroscopic (graph-level) vs. mesoscopic (community-level); network integration vs. segregation; geometrical vs. topological, etc. (Newman, 2010). Using machine learning approaches, features distinguishing networks can be identified and used to understand the underlying organization or architecture of the network.

The nodes (i.e. predicted Cav1 molecular localizations) were represented as graphs (networks), where a graph G=(V, E) is a pair of set of vertices or (nodes) V and set of edges E, where |V|=n, |E|=m, n is the number of nodes, and in is the number of edges. An edge is connected between a pair of nodes (i, j)∈V if the Euclidean distance between the nodes $d_{ij} \leq T$, where T is the proximity threshold. The Euclidean distance $d_{ij}=d_{ji}=\|i-j\|_2$ (the interaction between node i and node j is symmetric), and hence the graph is undirected. Two types of undirected graphs were constructed, weighted and unweighted. In the weighted undirected graph, the edge weight is set as $w_{ij}=1_{d_{ji}}$, i.e. stronger edges (higher weights) connect more proximate nodes.

Group Matching

To match groups of blobs (i.e. hypothesized as being of the same type) from the population of PC3 cells to similar groups in PC3-PTRF cell population, we first form an N×M similarity (or affinity) matrix Y, in which high similarity between the groups is encoded with small distances. N is the number of groups in the first population (PC3) and M is the number of groups in the second population (PC3-PTRF). The entry in the i-th row and j-th column of Y is set to $Y_{ij}=e_{-\|y_i-y_j\|_2}$, where $y_i$ and $y_j$ are the feature vectors (Table S2) describing the centroids of $group_i$ in $population_1$ and $group_j$ in $population_2$, respectively, and $\|y_i-y_j\|_2$ is the Euclidean distance. Then, $group_i$ in $population_1$ was match with the $j_*$-th group in $population_2$, where $j_*=argmin_j Y_{ij}$. A matching threshold β was applied to set the minimum value of similarity between the matched groups: If $min_j Y_{ij} > \beta$ for all j groups, then the $group_i$ is not matched to any of the j-th groups in $population_2$. Note that more than one similar group could be returned.

Blink Filtering by Leveraging Random Graphs

To decide whether or not a blink, in an ROI of a real cell, is regarded as noisy and hence must be filtered out, the network properties of that node representing the blink with the corresponding properties of nodes of a purely random graph were compared. Those nodes with properties similar to those of the purely random graph are regarded as random noise (and filtered out) and the remaining nodes are retained. The random graph is constructed with the same number of nodes as in the real cell ROI, and each spatial coordinate of the location of its nodes is generated with same distribution of the cell ROI blinks. For example, the locations of the blinks in both the X and Y dimensions followed a uniform distribution, while the distribution of the blinks in the Z dimension followed a normal (Gaussian) distribution. An example of generated random blinks that correspond to a real ROI taken from one of the PC3-PTRF cells in our data set (FIG. 5).

SMLM Simulation Using SuReSim Software

The recently published SuReSim software (Venkataramani et al., 2016) was used to simulate SMLM imaging for caveolae-like structures. A sphere with diameter of 60 nm to resemble a caveolae. The lateral precision (XY) was set to be 20 nm and the axial precision (Z) to be 50 nm. 40,000 frames were recorded and the label epitope distance was set to be 20 nm and the epitope density was set to be 0.1318 nm-2 to match the reported 145 Cav1 molecules per caveolae (Pelkmans and Zerial, 2005b). The SuReSim simulated data event list was processed using 3D SMLM Network Analysis and the obtained bio-signatures were compared with real data obtained for caveolae in PC3-PTRF cells.

Results

Network Analysis of 3D Cav1 Point Clouds

Figure 2A:
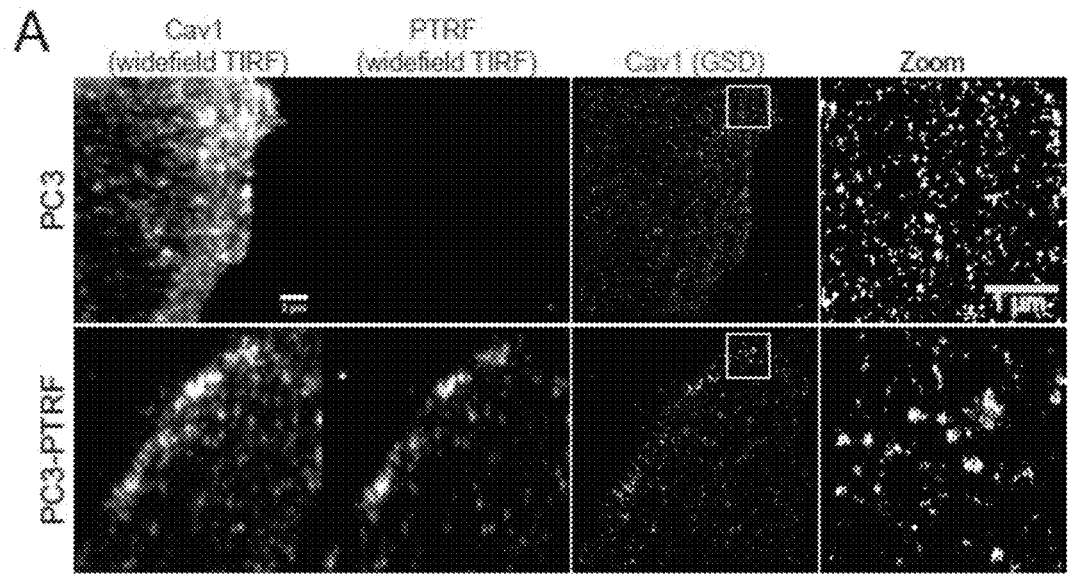
FIG. 2 illustrates computational network analysis for SMLM. A. Total Internal Reflection Fluorescence (TIRF) wide-field imaging of Cav1 and CAVIN1 (also called PTRF) and SMLM Ground state depletion (GSD) imaging of Cav1 in PC3 and PC3-PTRF cells. CAVIN1 (PTRF) was not detected in PC3 cells. Spot diameters from the two cell types (Experiment 1, see B) were binned (Bar: SEM; ***$p<0.001$). B. Details of four SMLM experiments imaged using Leica GSD microscope. C. Methodological pipeline to discover signatures of different Cav1 domains: 3D SMLM Network Analysis. A GSD image event list was converted to a 3D point cloud. Blinks within 20 nm were merged and the 3D point cloud divided into regions of interest (ROIs) for multi-threshold network analysis. Network measures filter the 3D point cloud to obtain clusters (blobs). Features were extracted for each blob and blob identification achieved via unsupervised learning methods.
Figure 2B:
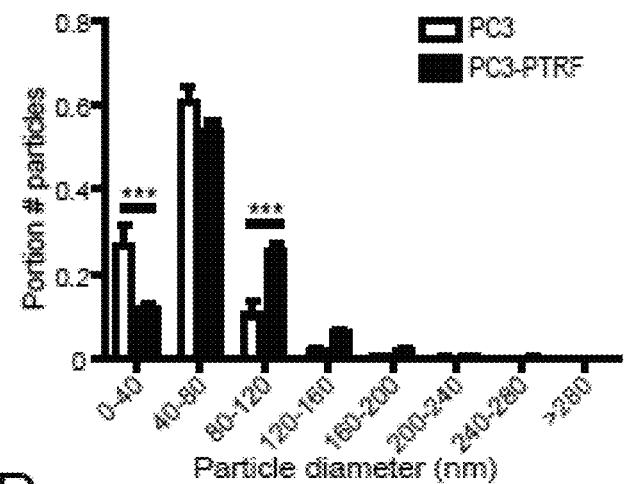

Indirect immunofluorescence labeling of PC3 and PC3-PTRF cells with anti-Cav1 primary and Alexa647 conjugated secondary antibodies is shown by TIRF and GSD-TIRF SMLM (FIG. 2A). Quantification of SMLM images identifies larger spots in caveolae-containing PC3-PTRF cells (FIG. 2A). The 3D locations (event list) of individual Cav1 blinks was obtained from three training experiments (FIG. 2B) based on Gaussian analysis of the PSF using Leica GSD software. No intensity thresholds were applied in order to ensure that all acquired blinks were returned. To study clusters or networks of representative Cav1 localizations, and not blinks, Cav1 localizations was assigned from the acquired blinks. Complex network analysis was applied to assign edges between predicted Cav1 localizations (nodes) and generate measures that define relationships between nodes. For instance, "degree" is a measure of the number of edges incident (connected) to a given nodes within a certain distance threshold.

The analysis pipeline (FIG. 2C), referred to as 3D SMLM Network Analysis, consists of six computational modules: 1) Merging algorithm: Iterative merging of all blinks within the 20 nm resolution limit of SMLM to generate nodes corresponding to predicted Cav1 localizations; 2) Space partitioning: Dividing the cell into regions of interests (ROIs) to facilitate whole network measure analysis via parallel high performance computing (HPC); 3) Multi-threshold network analysis: Constructing weighted and unweighted networks at various proximity thresholds to identify features and thresholds that differentiate PC3 and PC3-PTRF ROIs; 4) Background elimination: Using discriminative network measures to filter out noisy blinks relative to a random point distribution; 5) Cluster segmentation: Using the mean shift algorithm (Fukunaga and Hostetler, 1975; Comaniciu and Meer, 2002) to identify distinct clusters (or blobs) and extracting features for each cluster; and 6) Cluster characterization: Defining distinct clusters via unsupervised learning methods in PC3 and PC3-PTRF cells.

Figure 3A:
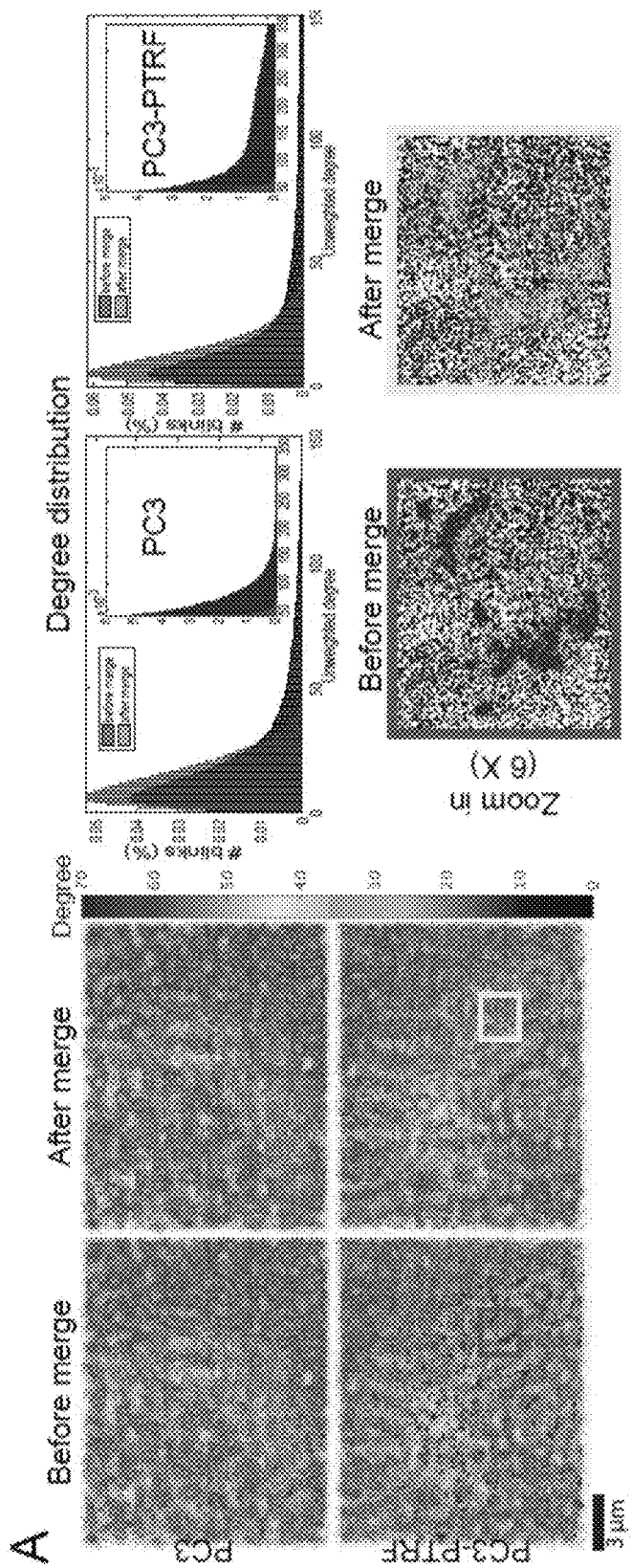
FIG. 3 illustrates iterative blink merging to correct multiple blinking of single fluorophores. A. An iterative merging approach of blinks within T=20 nm was used as a preprocessing step to correct for multiple blinking of a single fluorophore, blinking from multiple fluorophores on the same antibody, and multiple secondary antibody labeling of the same Cav1 molecule and associated drift. Network degree measure images and histograms of PC3 and PC3-PTRF cells before and after applying the merge module at 20 nm. B. The number of blinks and the percent reduction of total blinks for each experiment following iterative merging at 20 nm. The error bars represent the standard deviation.
Figure 3B:
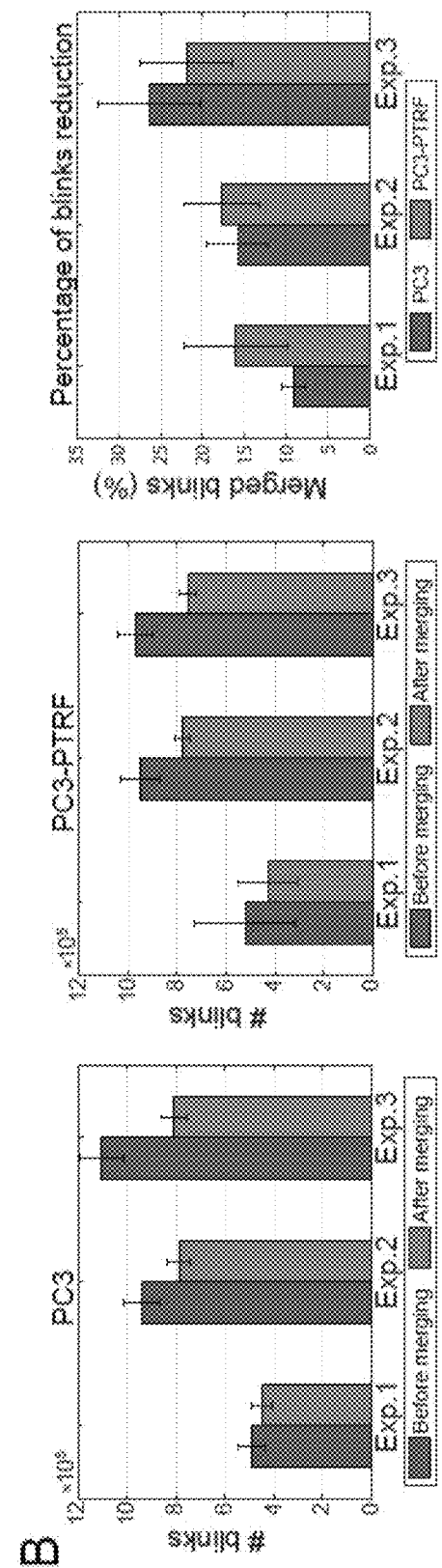

Erroneous positioning of acquired blinks in SMLM can be associated with the imaging process (dark time, imaging time, photoblinking and photoactivation) and localization errors (PSF fitting and overlapping, antibody labeling, microscope drift) (Quan et al., 2010; Annibale et al., 2011a, b; Rubin-Delanchy et al., 2015). As a result, multiple, temporally distinct blinks from the same fluorophore or same antibody-labeled Cav1 molecule can give rise to blinks with distinct localizations, thereby skewing the data and subsequent network analysis. To generate a robust method to remove high degree blinks and reconstruct a network of representative Cav1 localizations, an algorithm that performs iterative merging of blinks within 20 nm was applied, the reported resolution limit of the Leica GSD microscope. In short, for every blink, neighboring blinks within a 20 nm sphere centered around that blink were identified. Starting with the blink with the largest number of neighbors, that blink and all its neighbors were replaced by a new blink positioned at their average location. Then the blink with the second largest number of neighbors was processed and so on. The procedure until no pair of blinks are within 20 nm from each other. Note that blinks that start as being more distant than 20 nm may still be merged during this iterative process. Also note that k-d-tree search algorithm was used to speed up the process of finding the nearest neighbors. Running our algorithm takes<1 min to process an input point cloud of more than 1.5 million blinks. Application of the merging algorithm to PC3 and PC3-PTRF cells selectively reduces high degree (>50) nodes (FIG. 3A). Reduction in the total number of blinks by the merge algorithm varied from 9 to 26% (FIG. 3B).

Statistical Analysis of Features at the ROI Level

To identify the proximity threshold of nodes in 3D space that best discriminated between PC3 and PC3-PTRF cells, weighted and unweighted undirected networks at thresholds from 20 nm to 250 nm were constructed. To enable high speed processing of the large data sets, up to 1 million blinks per image (FIG. 3B), each image was divided into 36 ROIs ($3\times3\times1$ $\mu m^3$) and extracted 32 weighted and unweighted features at 24 thresholds (i.e. 768 features/ROI).

Figures 4A, 4B:
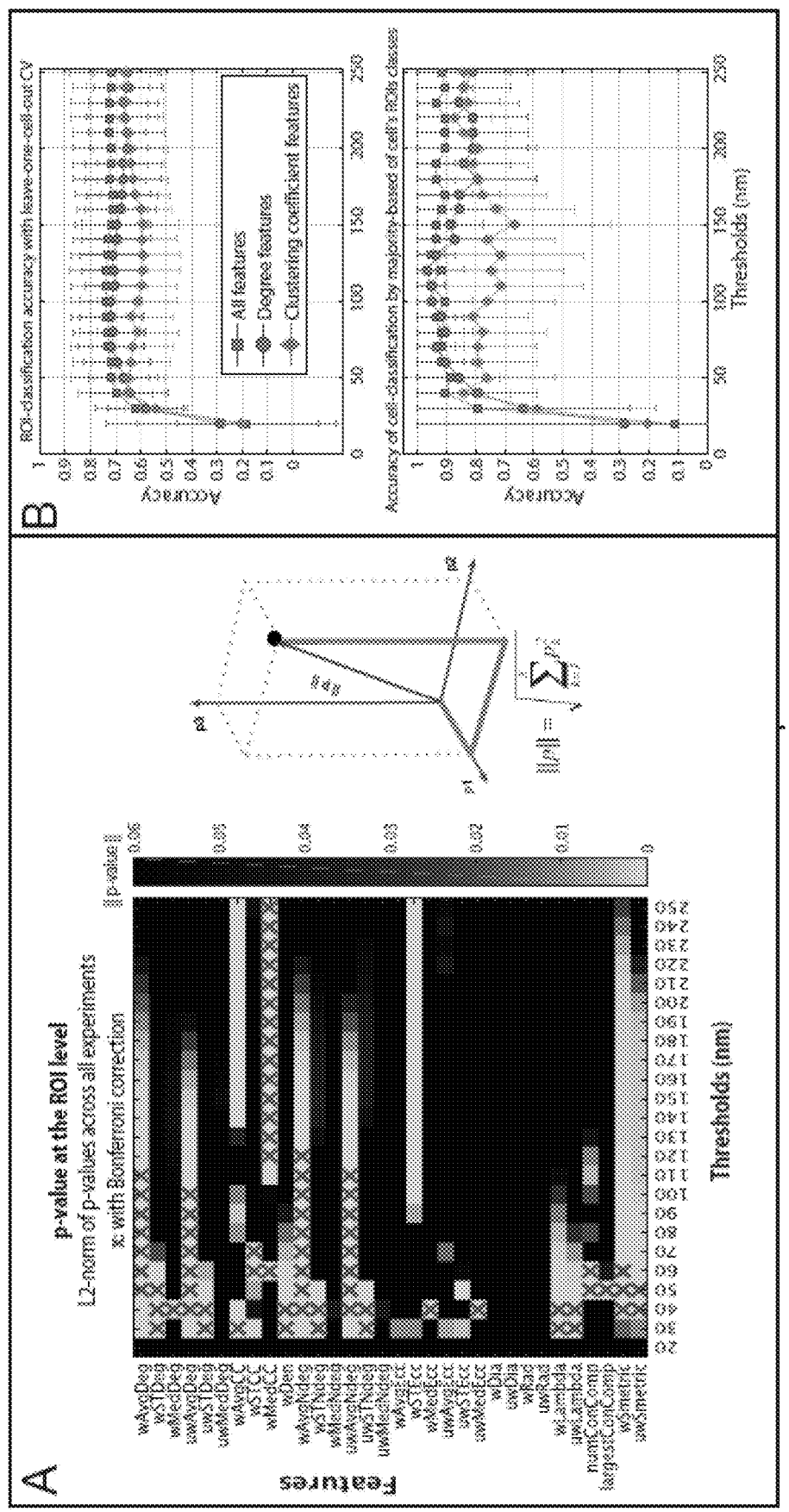
FIG. 4 illustrates multi-threshold analysis of PC3 and PC3-PTRF data at the region of interest (ROI) level. A. Multi-threshold statistical analysis showed network measures and thresholds that discriminate PC3 and PC3-PTRF 3D point clouds. For each experiment, the p-values were calculated by the two-sided non-parametric Mann-Whitney statistical test to evaluate the null hypothesis that the network measures of the two populations (PC3 and PC3-PTRF) followed the same distribution. p-values ($p_1$, $p_2$, and $p_3$) from Experiments 1-3 (see FIG. 1B) were aggregated via the L2-norm. The results with and without Bonferroni multiple comparisons correction are shown. B. Random decision forest accuracy of classifying the two populations at ROI (top) and cell level (bottom) using the whole feature set (red), degree features only (blue), and clustering coefficient features only (green). The error bars represent the standard deviation. C. Filtering-out noisy blinks using unweighted degree at 80 nm via comparison with random graphs. D. Filtering-out noisy blinks at 80 nm for unweighted degree, weighted neighboring degree (significant) and weighted clustering coefficient (non-significant). Vertical dashed red lines indicate level of noise removal.

The nonparametric Mann-Whitney statistical test was applied to find the features and corresponding thresholds at which they discriminate with statistical significance between PC3 and PC3-PTRF cells. P value matrices (32 features×24 thresholds) were combined by finding the L2-norm of $p_1$, $p_2$, and $p_3$; feature-threshold pairs that survived the Bonferroni multiple comparison correction are marked with red X's (FIG. 4A). Significant features grouped into two categories: degree features (wAvgNDeg, uwAvgNDeg, uwAvgDeg, wAvgDeg) and clustering coefficient features (wAvgCC and wMedCC). Degree features are more significant from 40-120 nm (average 80 nm) and clustering coefficient features from 120-250 nm (average 180 nm). Random decision forest (Breiman, 2001) machine learning classification, using a leave-one-cellout cross-validation (ROIs from each cell are excluded from training and used only in testing) strategy, tested the feature and threshold ranking. We report the classification accuracy of the detected class of (i) each test ROI and (ii) the cell, chosen to be the detected class of the majority of the ROIs (FIG. 4B). For both cases, classification accuracy is best for thresholds above 50 nm and increases for degree features between 70 and 130 nm (blue curve) and for clustering coefficient features between 170 and 250 nm (green curve) (FIG. 4B). Two peaks in the degree features histogram suggest the presence of low degree or noisy blinks and high degree or clustered nodes.

Figure 4D:
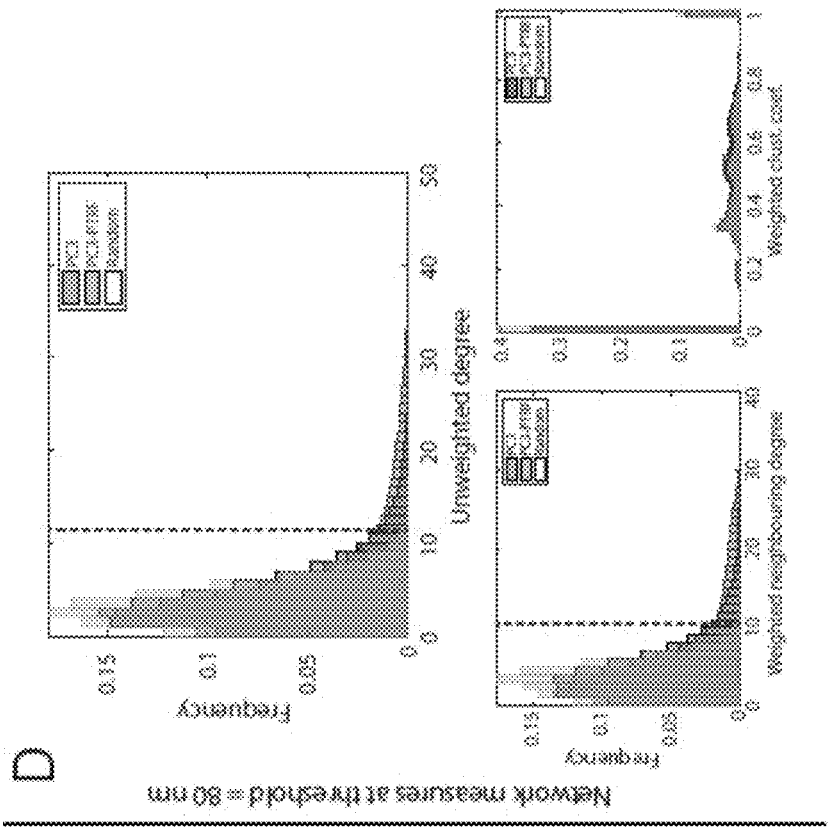
Figure 4C:
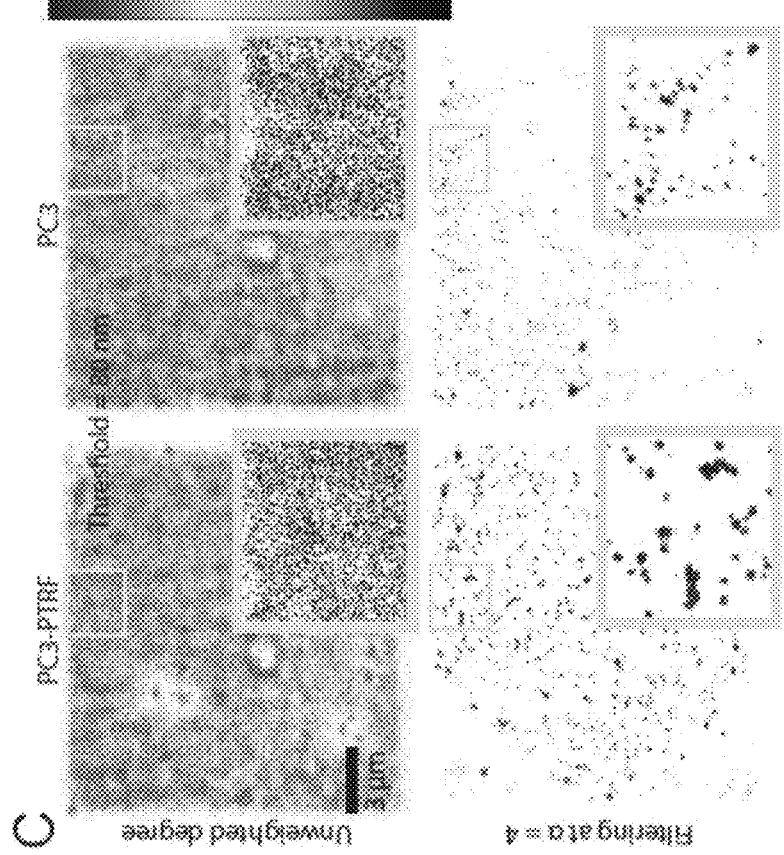
Figure 9A:
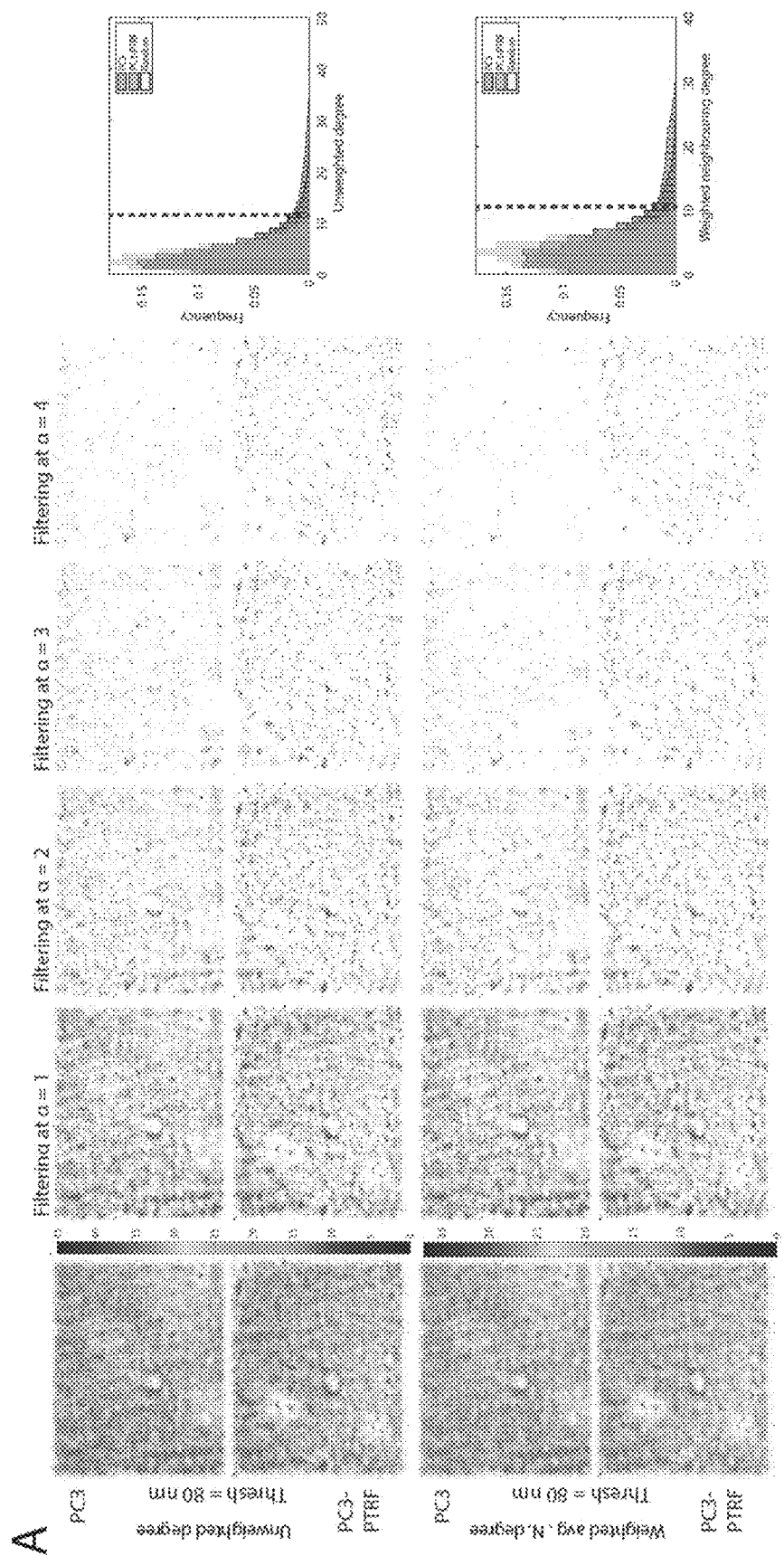
FIG. 9. Noisy blinks filtering using significant features at significant thresholds: The effect of changing α to filter out the noisy blinks. No intensity thresholds were applied to the GSD images. The first column shows all the blinks of two cells from PC3 and PC3-PTRF populations. The nodes are color-coded by the values of the different network measures at two different thresholds. The degree features are significant at 80 nm while the clustering coefficient feature is significant at 180 nm. The second, third, fourth, and the fifth columns shows the results of filtering the noisy blinks at different values of $\alpha=1, 2, 3, 4$ respectively.
Figure 9B:
Figure 9C:
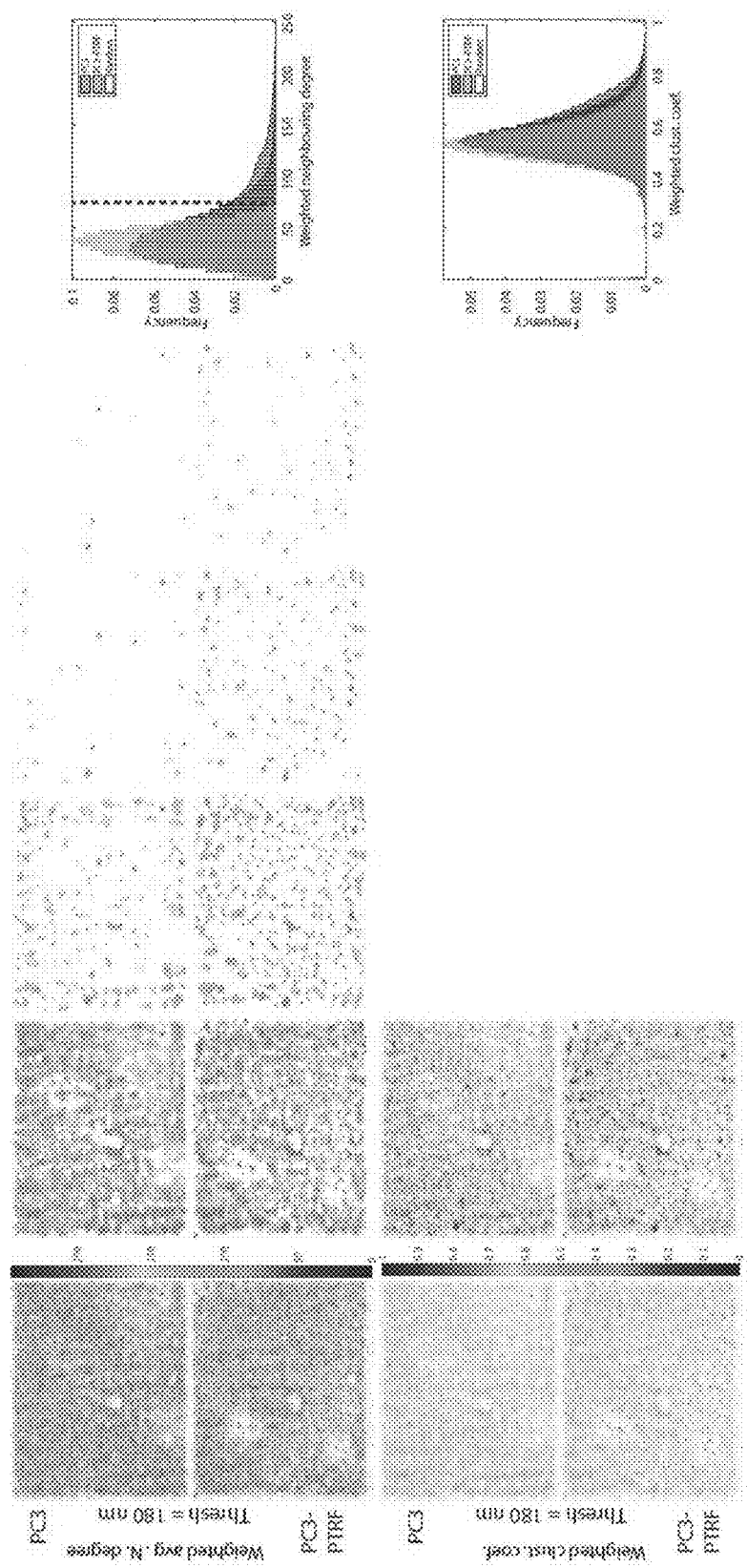

Significant differences between PC3 cells, lacking caveolae, and PC3-PTRF cells, that have caveolae, were detected for degree features between 40-120 nm (average 80 nm) and for clustering coefficient features between 120-250 nm (average 180 nm). 80 and 180 nm thresholds were chosen for further analysis. To filter out noisy blinks and return clusters in the PC3 and PC3-PTRF data, degree features at threshold 80 nm (the mean of the significant thresholds) were used and compared network measures with those of a random graph (FIG. 5). The $node_i$ is retained (i.e. not filtered out) if its degree value ($\delta_i$) is greater than the average degree value of a random graph ($\delta_{rand}$) multiplied by a scalar a, i.e. if $\delta i > \alpha \times mean (\delta r)$. The parameter a is user-controlled to determine the extent of removal of noisy blinks (FIG. 3C, D). We compared two-degree (uwAvgDeg; wAvgNDeg) and one clustering coefficient (wAvgCC) measures at thresholds 80 and 180 nm (FIG. 4D,9) with network measures of a random graph. We tuned $\alpha$ so that $\delta_i$ does not exceed the histogram tail of the random graph degree features (dashed red line) and obtained the best filtration with $\alpha$=4 (FIG. 9). Degree feature filtering worked better at threshold 80 nm, with wAvgNDeg providing stricter filtering that removes tiny clusters. Filtering eliminates background labeling but also monomeric Cav1 nodes, such that our analysis selectively includes Cav1 clusters or blobs.

Blob Segmentation, Grouping and Matching

Figure 6A:
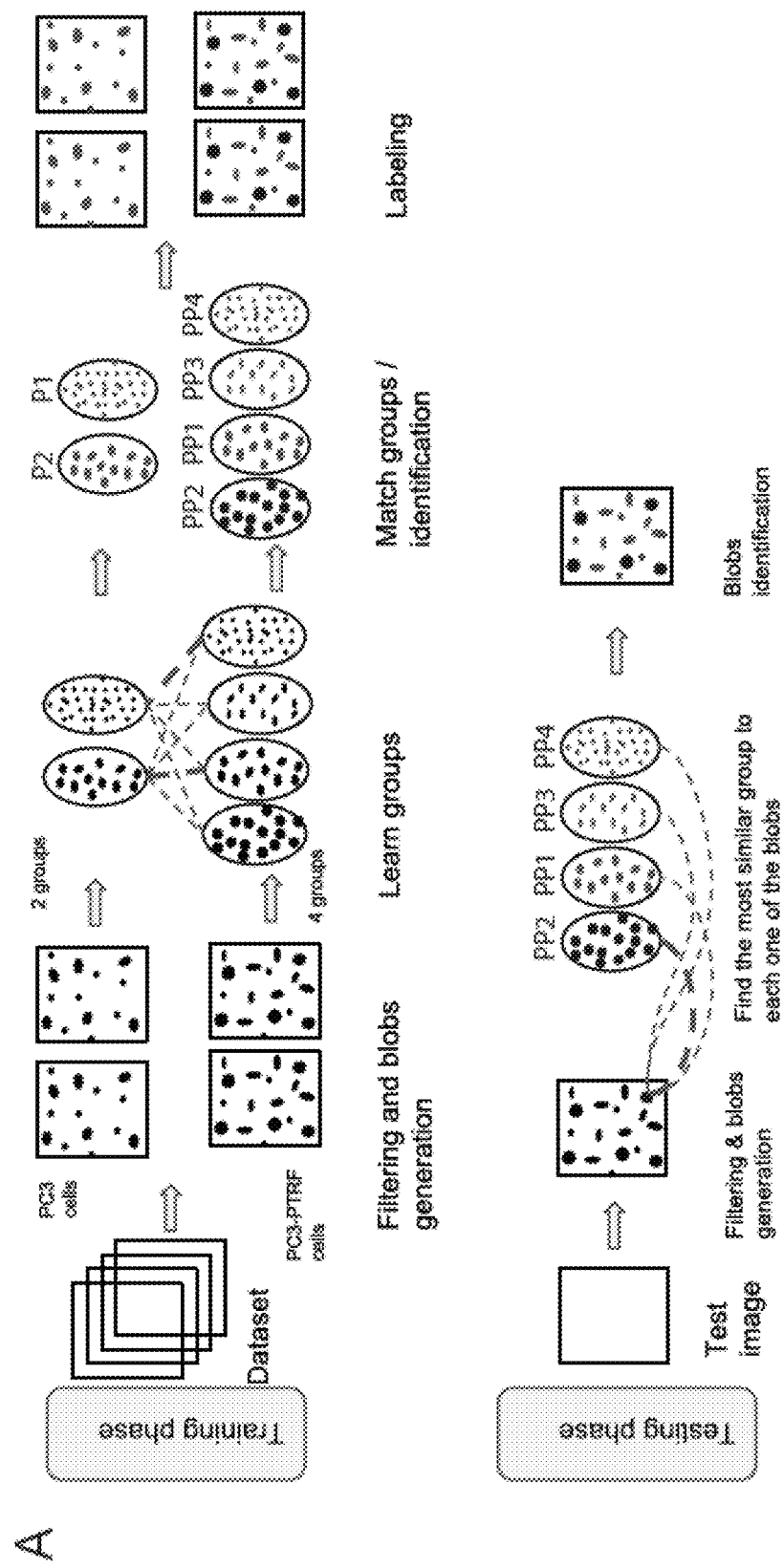
FIG. 6 Unsupervised learning identified different clusters (blobs). A. The unsupervised learning framework to build the cluster (blob) identification model based on datasets. Training phase; the cells from both populations of the first three experiments (FIG. 2B) were used to build the learning model using the unsupervised clustering. The cells were divided into ROIs. A multi-threshold network analysis for each ROI was employed to filter-out the noisy blinks and find the clustered nodes. The blobs were generated from the clustered nodes using the mean shift algorithm. A new set of features were extracted from each blob and fed into the unsupervised clustering (X-means) to learn the different groups. The groups from PC3 and PC3-PTRF populations were matched using the similarity analysis to identify the groups' types. The matched groups were used to label the blobs on the cells. Testing phase; the built model was used to identify the blobs of the cells from experiment 4. The cell was passed via the space division to get the ROIs. The multi-threshold analysis was applied to filter-out the noisy blinks and return the clustered nodes. The blobs were generated using the mean shift algorithm. The same set of features was extracted for each blob. Each blob feature vector was tested against the centroid feature vector of the learned groups. The closest distance is the most similar group to this blob. The blobs were labeled based on the similarity of their feature vector with groups' centroids. B. After filtering, blob-level feature analysis and segmentation identified 2 groups (P1, P2) in PC3 and 4 groups (PP1, PP2, PP3, PP4) in PC3-PTRF by unsupervised learning. One-to-one group matching (box) with distances among feature vector of groups centers used as the similarity measure (closer groups are more similar). C. Each group of blobs (S1 or S2 scaffolds or caveolae) was extracted and shown as different channels. Graph shows percent distribution of blobs in PC3-PTRF and PC3 cells.
Figure 6C:
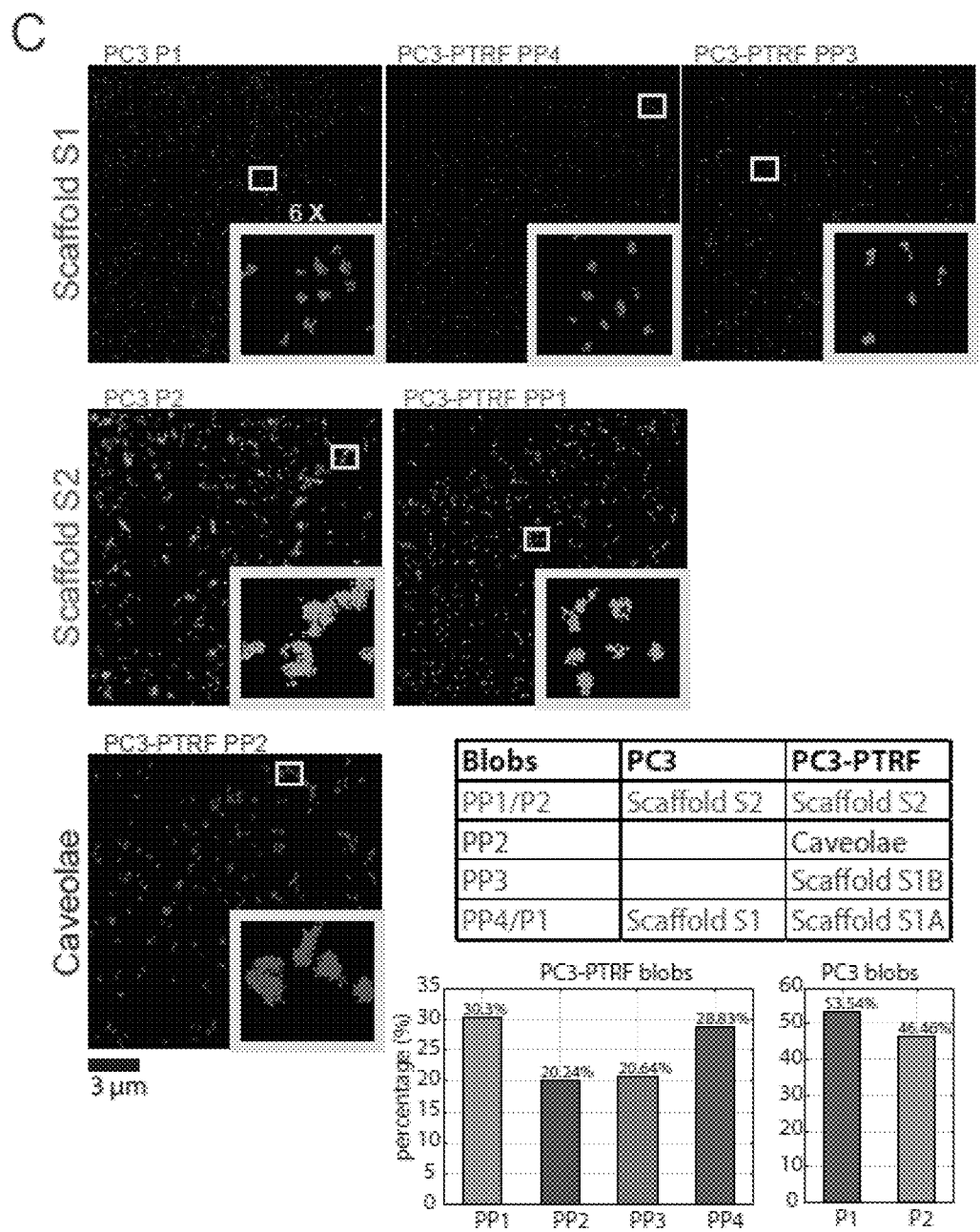

Having removed high degree blinks and filtered-out noisy blinks, we then employed the meanshift algorithm (Fukunaga and Hostetler, 1975; Comaniciu and Meer, 2002) to segment and separate each blob. Twenty-eight measures at 80 nm threshold describing size, shape (spherical, planar, linear) and topology (hollowness, modularity) were extracted for each individual blob. The X-means (Pelleg and Moore, 2000) (unsupervised clustering algorithm) returned the optimal number of groups in each population (FIG. 6C): 2 groups (P1, P2) for PC3 and 4 groups (PP1, PP2, PP3, and PP4) for PC3-PTRF (FIG. 6A-C). Unsupervised clustering methods gathered similar blobs in the same group and dissimilar blobs in different groups. To match the groups, we calculated the Euclidean distances between every pair of group centers, a vector of 28 features, in a distance matrix (FIG. 6B, box). By setting the similarity threshold $\beta$ to 30, we found the most similar groups across the two populations. The PC3 P1 group is most similar to PC3-PTRF PP3/PP4 (S1 scaffolds) and P2 most similar to PP1 (S2 scaffolds) (FIG. 6B, box). The PC3-PTRF group most dissimilar to PC3 P1 and P2 groups is PP2, suggesting that it corresponds to caveolae. Representative images of the blob groups are shown in FIG. 6B.

Blobs Signature

Figures 7A, 7B, 7C, 7D:
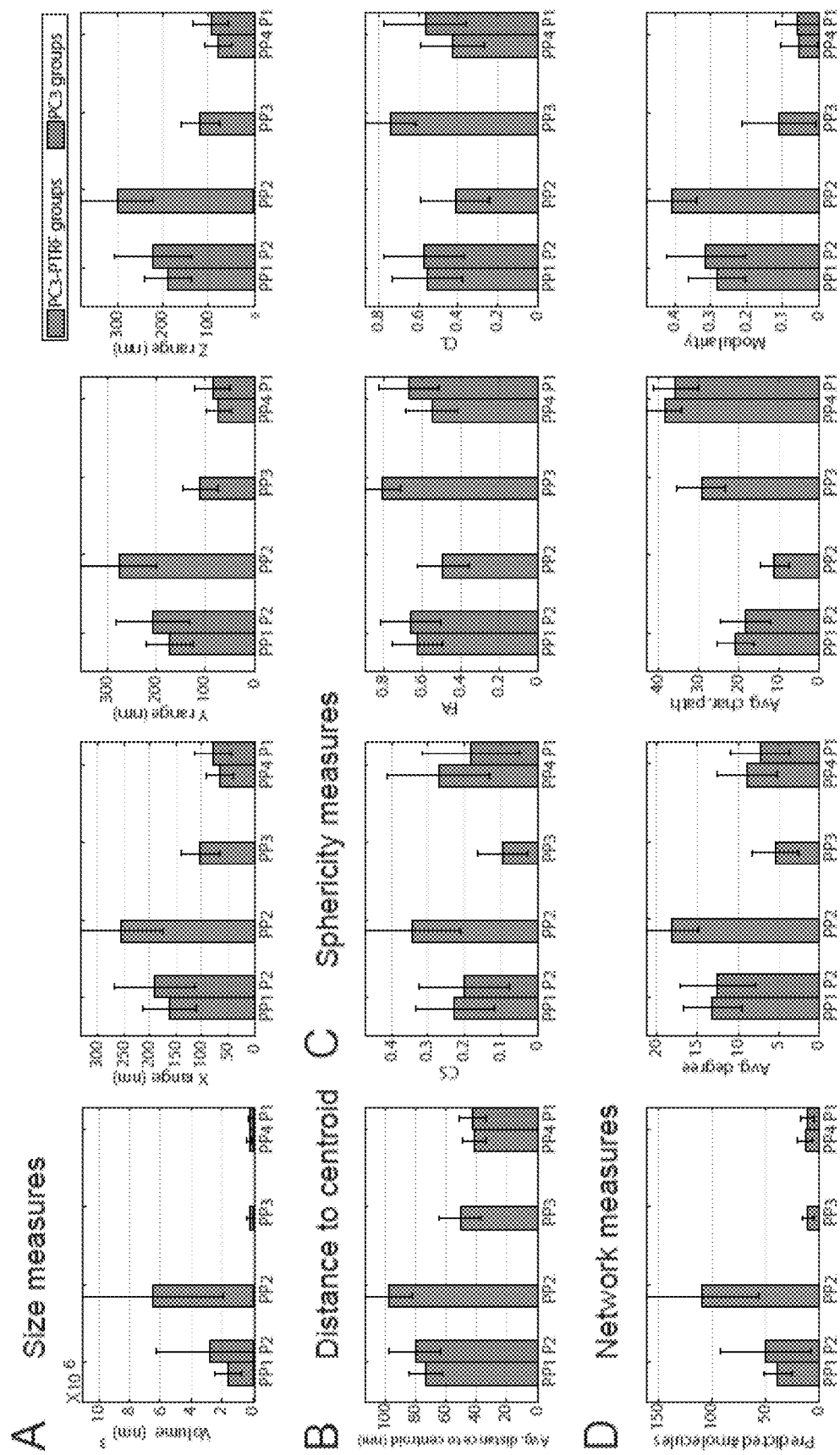
FIG. 7. Digital bio-signatures of caveolae and scaffolds. Of 28 signatures, measures for each class of blob was presented: A. Size measures (volume, X-, Y-, Z-range); B. Hollowness measure: (distance to centroid); C. Shape measures (sphericity, fractional anisotropy, linearity); D. Network measures (# predicted molecules, degree, character path, modularity). E. Multi-threshold modularity analysis shows the number and average size of connected components and modules for PC3-PTRF blobs at different thresholds. F. 2D relationship between features for different PC3-PTRF blobs are shown. The error bars represent the standard deviation. For A-D, the differences for every pair of the groups are statistically significant ($p<0.0001$).

PP2 blobs or caveolae are larger (~250-300 nm) than S1 (P1/PP3/PP4) and S2 (PP1/P2) scaffolds (FIG. 7A). S2 scaffolds are larger than S1 scaffolds and their increased height suggests that S2 scaffolds present a non-planar morphology (FIG. 7A). PP2 caveolae are the hollowest structures with an average distance to centroid of ~95 nm and no nodes<60 nm from centroid (FIG. 7B, F). For S1 scaffolds, the minimum distance to centroid was 20 nm, indicating that these structures are filled in. S2 scaffolds were also hollow, showing an average distance to centroid of 70 nm and no nodes<50 nm from centroid (FIG. 7B, F). PP2 caveolae contain 109±52, S1B (PP3) scaffolds 10±6, S1A (PP4) scaffolds 13±7 and S2 (PP1) scaffolds 38±14 nodes, corresponding to predicted number of Cav1 molecules (FIG. 7D). S1 scaffolds therefore correspond to SDS-resistant oligomerized Cav1 units of 15 Cav1 molecules (Monier et al., 1995) and PP2 blobs approach the predicted 144±39 Cav1's per caveolae (Pelkmans and Zerial, 2005a). S2 scaffolds are an as yet unidentified non-planar Cav1 scaffold.

Figure 7E:
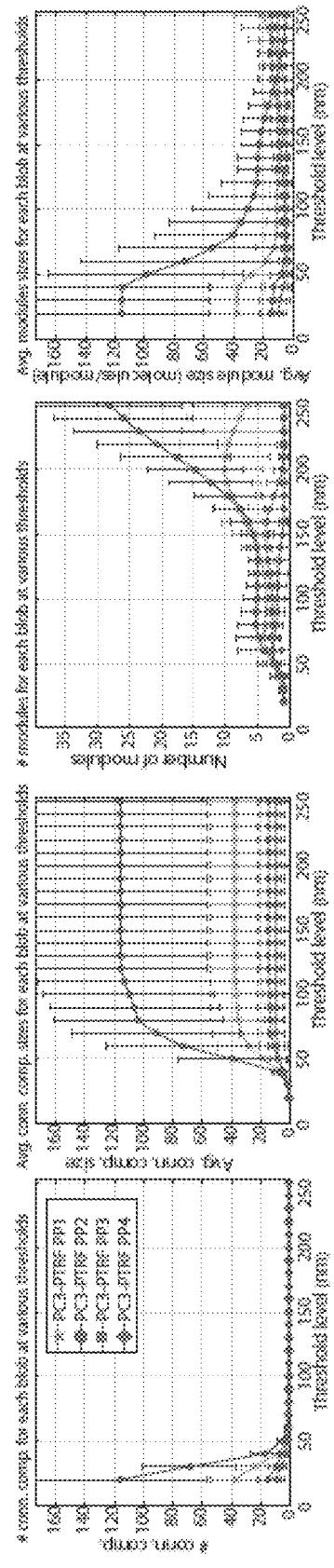
Figure 7F:
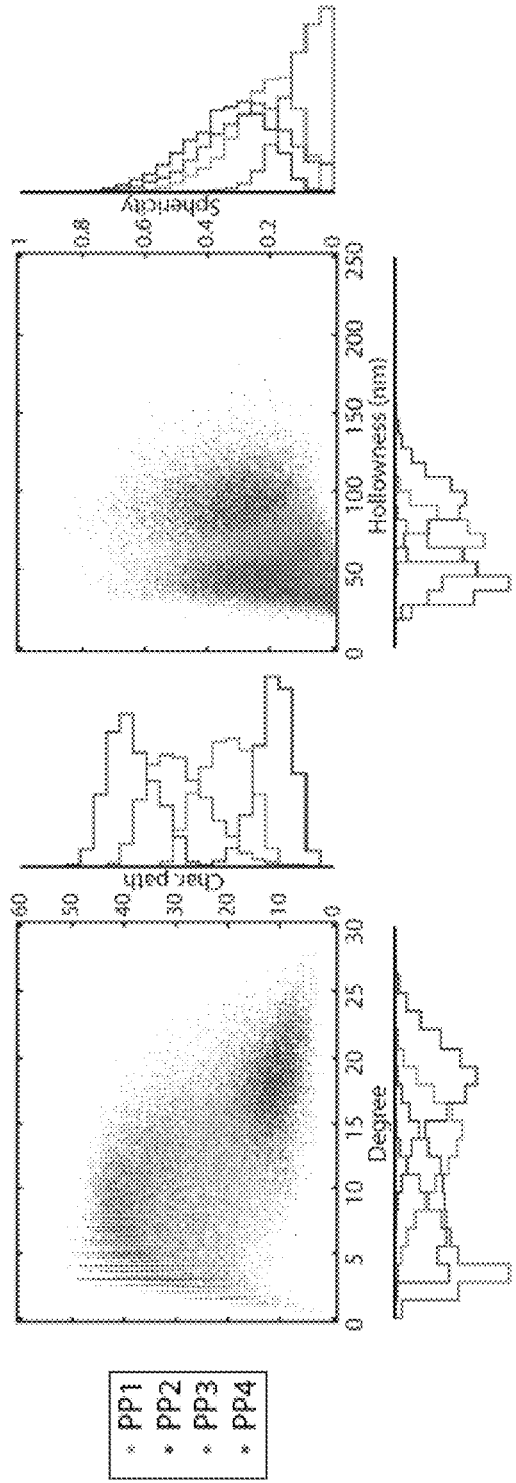

PP2 caveolae show the highest degree, lowest clustering coefficient and shortest characteristic path length and have higher modularity (FIG. 7D). We employed the Newman method (Newman, 2006b) to find the optimal number of modules and extract modularity features for each blob at thresholds from 20 to 250 nm. Most of the blobs become one connected component (i.e. all the nodes are connected) at thresholds>50 nm (FIG. 7E) and show a stable modular structure between thresholds of 60-140 nm, with PP2 caveolae presenting 5-6 modules per blob (FIG. 7E).

Figures 8A, 8B:
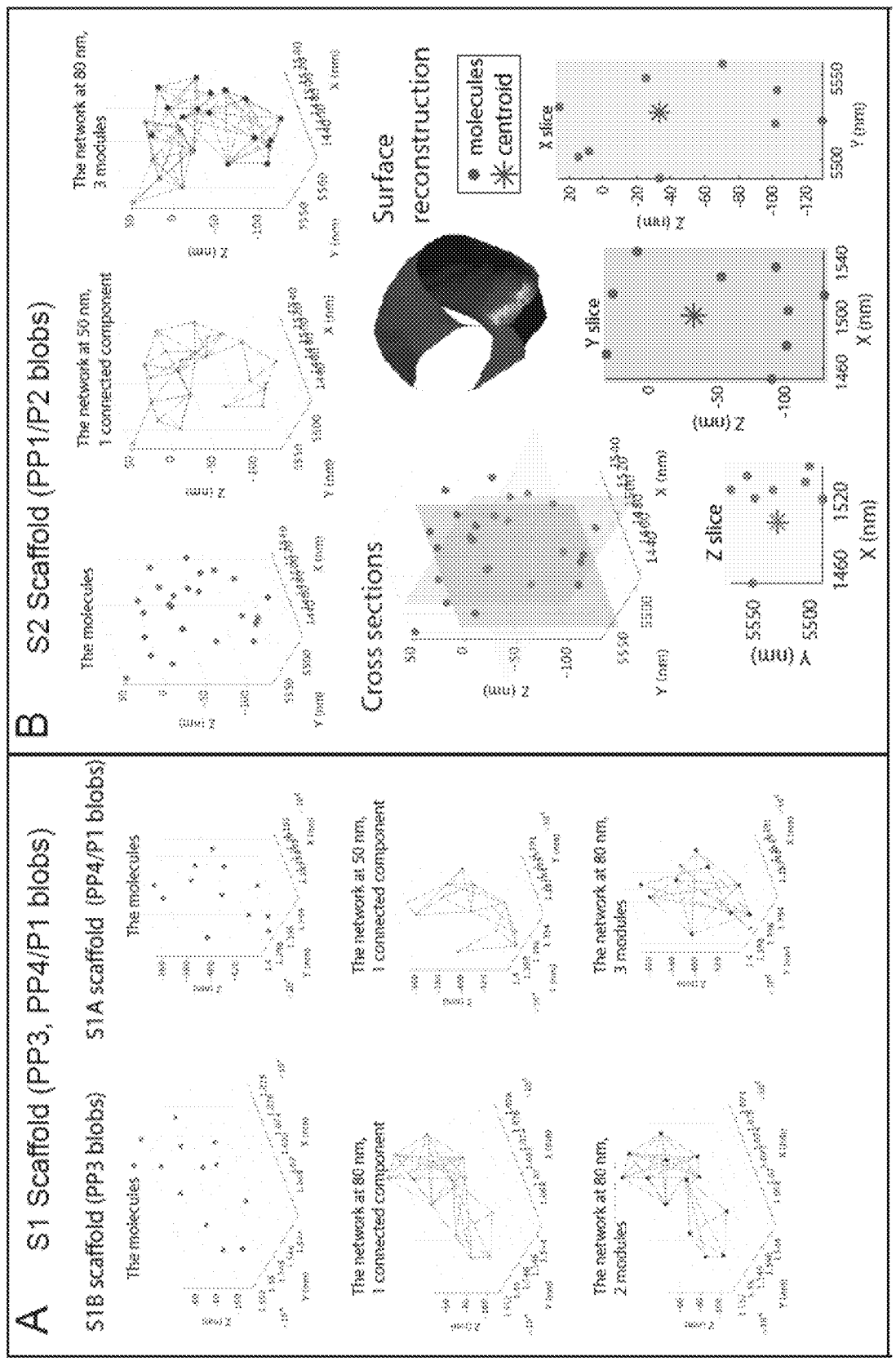
FIG. 8. Visualization of representative blobs from PC3/PC3-PTRF cells (Leica GSD microscope). Blob's molecules and networks (including number of connected components and modules) at various thresholds are shown for: A. S1 scaffolds (PP3/PP4 blobs); B. S2 Scaffolds (PP1 blob); and C. Caveolae (PP2 blob). Cross-sections, XYZ slices and surface reconstructions are shown for S2 scaffolds and caveolae. Slice thickness for S2 scaffolds is 20% of the whole range of the blob size in each dimension and for caveolae 10%. S2 scaffolds are hemi-spherical and consist of 3-4 modules. Caveolae are spherical and hollow and consist of 5-6 modules.
Figure 8C:
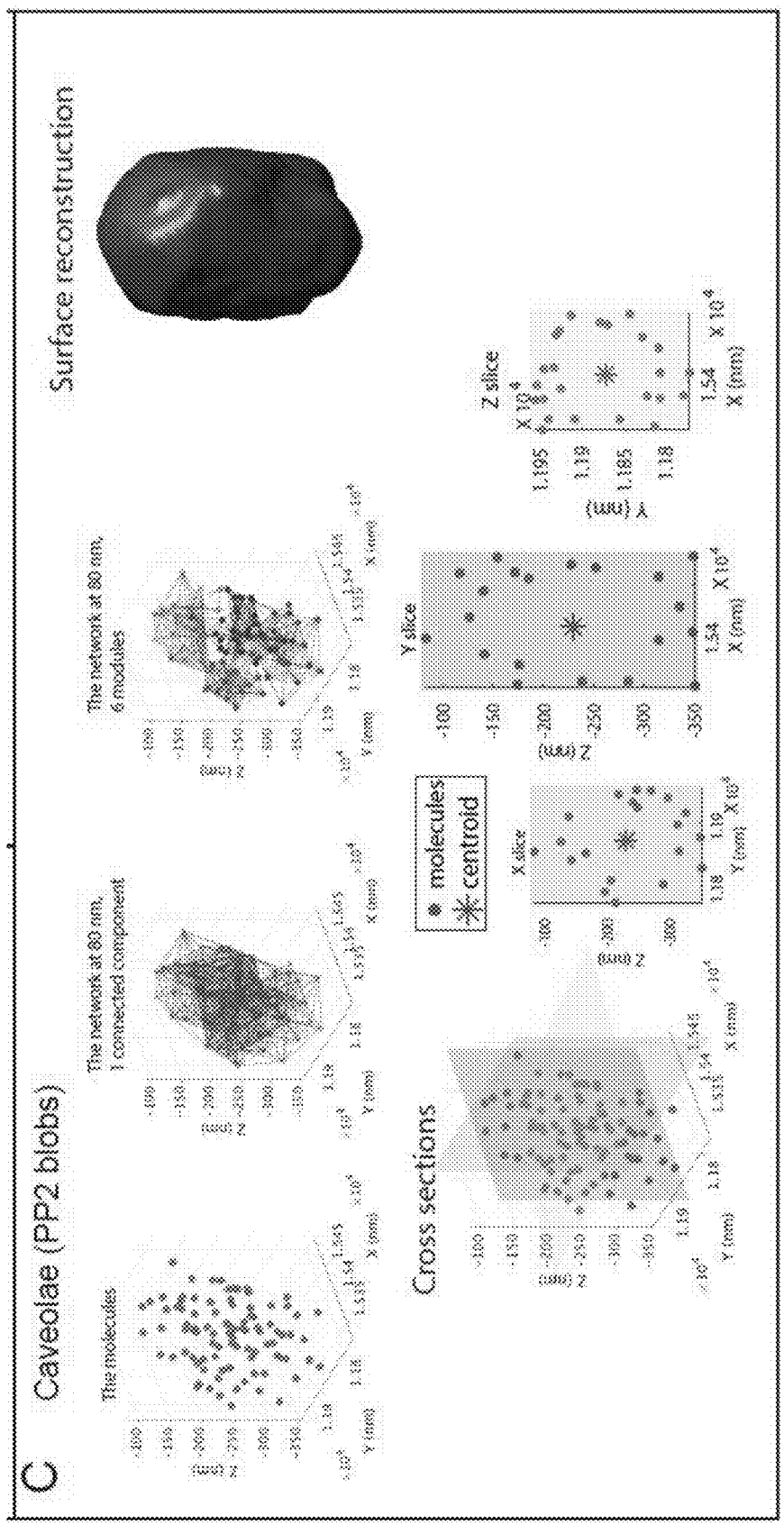

For selected S1, S2 scaffolds and caveolae, predicted 3D molecular distribution, network connections at the lowest threshold at which connected components equals one, and modular structure are shown in FIG. 8. S1A (P1/PP4) and S1B (PP3) scaffolds are composed of 10-15 molecules, equivalent to SDS resistant Cav1 oligomers (Monier et al., 1995) and differ primarily in that S1B scaffolds are more elongated and S1A more spherical. The presence of pentagonal sub-modules supports EM data of polygonal repeating units in the caveolar cage (Walser et al., 2012). PP1/P2 S2 scaffolds present a hemi-spherical shape and hollow core from XYZ cross-sections (FIG. 8B). PP2 caveolar blobs form highly interconnected hollow, spherical networks that contain, for the representative blob shown here, 6 modules (FIG. 8C).

Discussion

Application of computational network modelling and machine learning based 3D pattern analysis tools to SMLM data sets (3D SMLM Network Analysis) has identified plasma membrane associated Cav1 scaffolds that combine to form caveolae and larger scaffolds. S1A scaffolds are equivalent to the 200-600 kD SDS-resistant, 8S Cav1 oligomers of 14-15 Cav1 molecules (Monier et al., 1995; Sargiacomo et al., 1995; Scheiffele et al., 1998; Hayer et al., 2010). The presence of these structures in our analysis indicates that they can be delivered to the cell surface without assembling into larger structures in the Golgi (Hayer et al., 2010). S1A scaffolds dimerize to form S1B scaffolds and groupings of 3-4 S1A scaffolds form larger hemi-spherical S2 scaffolds. Biochemical fractionation using sucrose density gradients and mild lysis conditions reported, in addition to 8S complexes, larger 70S complexes, predicted to contain 160 Cav1 molecules and corresponding to Cav1 oligomers of assembled caveolae (Hayer et al., 2010). Both S1B and S2 scaffolds therefore represent intermediate Cav1 oligomers, that may be unstable upon detergent extraction. Regrouping of S1A scaffolds to form larger scaffolds and caveolae is associated with a more compact Cav1 organization (higher degree, reduced characteristic path) and increased curvature (sphericity). The presence of hemi-spherical S2 scaffolds in PC3 cells suggests that Cav1 oligomerization can induce membrane curvature independently of CAVIN1, as reported for Cav1 in bacteria (Walser et al., 2012).

Consistently, 10 Cav1 densities and a decagonal outline has been reported for Cav1-induced caveolae in bacteria (Walser et al., 2012). Further, EM tomography of caveolae labeled with MINISog, reports the presence of 12 regularly spaced Cav1 densities with a half-maximum width of 8-10 nm and spacing of 10 nm (Ludwig et al., 2013). A recent model of caveolae based on biochemical and cryoEM analysis proposed that caveolae are polygons (dodecahedrons) of Cav1 disks, equivalent to 8S oligomers (Stoeber et al., 2016). Our identification of 6-7 caveolae modules in the caveolar coat is consistent with this model and suggests that 8S oligomers, or S1A scaffolds, regroup to form larger scaffolds that combine to form a caveolae (FIG. 8C). The striated caveolar coat observed by deep-etching EM and platinum coating (Rothberg et al., 1992) has been suggested to reflect the presence of rod-like cavin oligomers (Ludwig et al., 2013; Gambin et al., 2014; Kovtun et al., 2014), that may form a net around the Cav1 disks (Stoeber et al., 2016).

Using blinks to define molecular architecture assumes first that each blink equals a fluorophore. However, the same fluorophore can blink twice in succeeding acquisition frames (Dempsey et al., 2012). Further, the same molecule can be labeled by different fluorophores, either on the same secondary antibody or on different secondary antibodies binding to the same protein. To address these possibilities, we developed an iterative merging algorithm, in which all blinks within a specified distance (the merging threshold) are combined into one average position. The algorithm iteratively combines all blinks within the merging threshold, in this study set at 20 nm, and converges when there is no pair of blinks within the merging threshold. As such, the merging algorithm allows the interrogation of molecule number and organization within the structure. As SMLM resolution approaches molecular distances between proteins, and particularly at high protein densities, the blinking cycles of individual fluorophores overlap in time such that undersampling and undercounting is a major concern (Fricke et al., 2015). Indeed, our approximation of 110 Cav1 molecules is less than the predicted 145 Cav1 proteins per caveolae or 160 Cav1's per 70S oligomer (Pelkmans and Zerial, 2005b; Hayer et al., 2010). We used a fixed merge threshold for this study that did not take into consideration the differential Z resolution of cylindrical lens-based SMLM. Future studies should consider modulation of the merge threshold to adapt to labeling conditions, microscope acquisition parameters and the different Z resolution of standard SMLM systems.

Figure 11B:
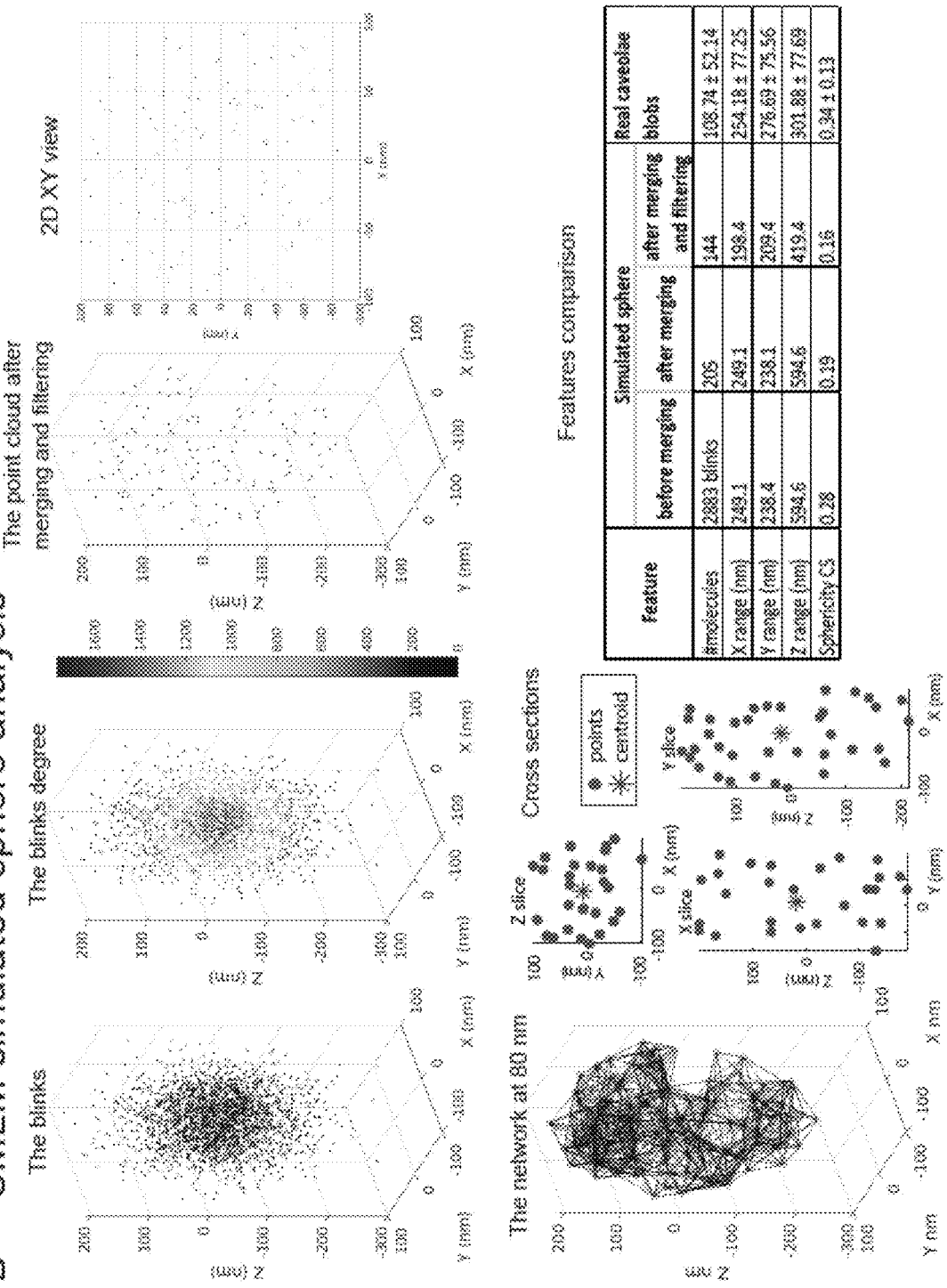

Further, the ~250 nm average diameter of caveolae blobs is substantially larger than the size of caveolae; although minimum values (X-range: 89.4 nm; Y: 86.8 nm; and Z: 78.2 nm) of the 80,000 blobs analyzed approach the 60-80 nm caveolae diameter by EM (Parton and Simons, 2007). Consistent with our findings, EM analysis of anti-caveolin labeling is cytoplasmic and at a distance from the membrane (Ludwig et al., 2013). We used SuReSim software (Venkataramani et al., 2016) to simulate SMLM imaging data for a caveolae-like structure. SuReSim software simulates imaging data of ground-truth structures with any 3D geometry using specific antibody labelling and acquisition parameters. Using labeling and acquisition parameters similar to those used to image Cav1-labeled PC3 and PC3-PTRF cells, we generated an SMLM point cloud for a 60 nm-sphere, mimicking a caveola (FIG. S5A). We applied our analysis pipeline to the simulated data and obtained results (number of predicted molecules, shape, and size features) very similar to what we obtained for real data of caveolae structures (FIG. 11B). The more elongated shape of the simulated point clouds, based on a Z resolution SuReSim input of 50 nm, suggests that Z resolution of the Leica SMLM microscope is better than 50 nm. Future analyses combining improved labeling approaches (such as smaller Fab antibody fragments), drift controlled acquisition and cluster analysis should lead to substantially improved resolution and better definition of molecular architecture.

Figure 2C:
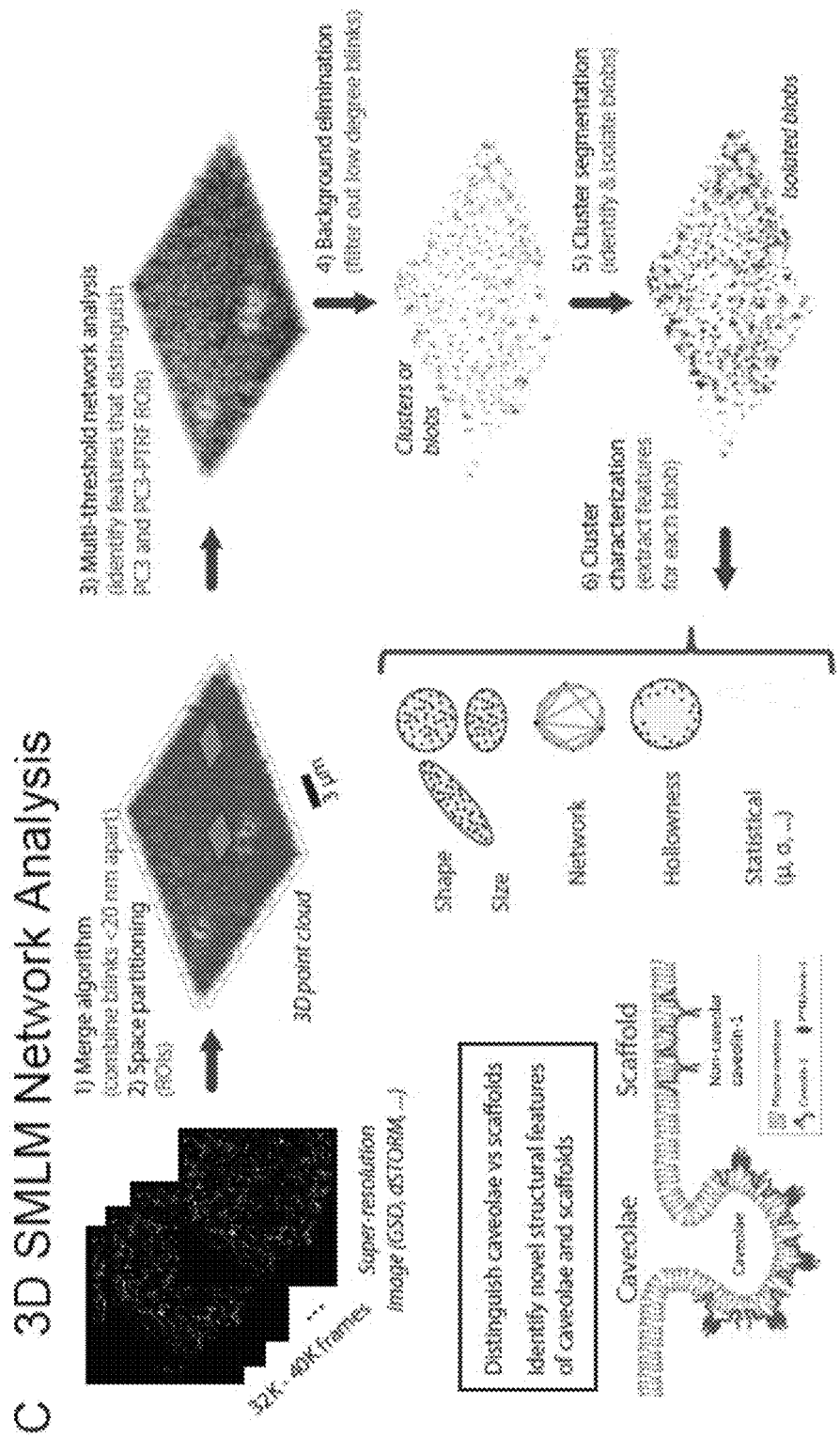

The 3D SMLM Network Analysis is designed to be scalable for big-data processing by exploiting parallel programming enabling application of the algorithms to whole cell SMLM data (FIG. 2C). Other methods are not able to process our SMLM datasets. Some methods crashed multiple times before identifying clusters while other methods took excessively long times (e.g. more than 3 hours) to process just one ROI from our data and without retrieving good clusters at the end.

Importantly, we are the first to use machine learning algorithms to quantify specific features of blobs and identify them automatically. We equipped 3D SMLM Network Analysis with a feature extraction module that can be used to extract features for individual clusters. The clusters features can be used for further analysis (e.g. retrieval, identification, grouping, molecular architecture analysis, etc. of the clusters) by machine learning. Network analysis, as described here, can therefore be used to reconstruct heterogeneous clusters of different shapes and sizes. Further development and refinement of this approach should allow the determination of the molecular architecture of multiple sub-diffraction limit cellular structures. As indicated, 3D SMLM Network Analysis is a fast, 3D, scalable, and multiscale method. Moreover, SMLM Network Analysis is enabled with single cluster visualization and can be integrated with different machine learning approaches to extract and automatically identify cluster features.

Network analysis has therefore provided us with invaluable insight into the structure of subdiffraction limited Cav1 domains. This analysis has defined three classes of non-caveolar scaffolds, including a heretofore undescribed hemispherical intermediate distinct from the biochemically defined 8S and 70S Cav1 complexes (Hayer et al., 2010) and enhanced our understanding of how Cav1 molecules organize to form a caveolae. Indeed, we argue that point cloud network analysis is particularly appropriate for the analysis of the blink distributions generated by SMLM and takes super-resolution fluorescence microscopy beyond the "pretty" picture to define underlying molecular architecture.

Example 2: Super-Resolution Modularity Analysis Shows that Polyhedral Caveolin-1 Oligomers Combine to Form Scaffolds and Caveolae Introduction Of the various super-resolution microscopy approaches, the best resolution is obtained using single-molecule localization microscopy (SMLM), based on the repeated activation (blinking) of small numbers of discrete fluorophores, usually through dSTORM. Precise localization of these blinks is determined from a Gaussian fit of the point-spread function (PSF) providing ~20 nm X-Y (lateral) resolution and ~25-50 nm Z (axial) resolution for astigmatic lens 3D SMLM (Huang et al., 2008; Shroff et al., 2008). SMLM generates point coordinates in 3D space that can then be used to reconstruct localizations with significantly improved resolutions. An alternate approach to study point distributions is to visualize them as a graph or network. Graphs are mathematical structures used to model interactions between entities for many systems, with the entities represented as graph nodes and the connections between them as edges (Newman, 2003). Real world graphs are frequently complex networks that have many different subgraphs or modules (Kim and Wilhelm, 2008). Networks with high modularity have dense connection (edges) between the nodes within modules (sub-networks) and sparse connections between nodes in different modules. The optimization problem of finding the different divisions of a network (i.e. modules) have been solved via various methods such as spectral algorithms and normalized-cut graph partitioning (Newman, 2006a; Newman, 2013). Network and subgraph (module) analysis are therefore ideally suited to define molecular organization and subgroup organization between the labeled molecules within the 3D SMLM point cloud of macromolecular complexes.

A major challenge to determining molecular structure by SMLM is determining molecular localizations from the millions of blinks generated by SMLM, many of which derive from the same labeled molecule, particularly when the labeling approach is based on antibody labelling (i.e. dSTORM). The same fluorophore can blink twice in succeeding acquisition frames dependent on the on-off duty cycle (Dempsey et al., 2011a) and the same molecule can be labeled by different fluorophores, either on the same secondary antibody or on different secondaries bound to the same target protein. Each of these blinks is subject to localization error due to drift and potential error in Gaussian localizations. Finally, the use of dual antibody labeling, in which each IgG has a size of 5-7 nm, can mislocalize antigen by as much as 10-15 nm (Ries et al., 2012). Multiple, distinct blinks therefore derive from the same molecule and generate a dense, high degree non-biological network (NBN) centred around the actual molecule (Khater et al., 2018). Network analysis of the biological network, composed of nodes corresponding to molecular localizations of the labeled proteins, requires reduction/consolidation of the NBNs. To do so, we developed a merge algorithm, in which blinks within a defined proximity threshold (PT) are iteratively combined into one average position. Blinks in closest proximity are combined first such that blink merging is initiated within the dense NBNs and progressively incorporates blinks until no blinks within the point cloud are closer than the PT.

Caveolae are smooth 50-80 nm plasma membrane invaginations whose formation requires the coat protein Cav1 and the adaptor protein CAVIN1 (also called PTRF)(Hill et al., 2008). Functional roles of caveolae include: mechanoprotective membrane buffers; mechanosensors; signaling hubs; and endocytic transporters (Parton and del Pozo, 2013). Cryo-electron microscopy (cryo-EM) analysis of caveolae has reported that the Cav1 coat is polygonal, formed of distinct edges and suggested to form a dodecahedral cage (Ludwig et al., 2016; Stoeber et al., 2016). CryoEM analysis of Cav1 protein distribution in the caveolae coat, in either mammalian cells or following heterologous Cav1 expression in bacteria, show that Cav1 exhibits a highly regular distribution of repeating polygons (Ludwig et al., 2013; Ludwig et al., 2016; Walser et al., 2012). CAVIN1 forms an outer filamentous coat layer whose filamentous structure likely corresponds to the striations observed on caveolae by deep-etch EM (Kovtun et al., 2014; Ludwig et al., 2013; Ludwig et al., 2016; Rothberg et al., 1992; Stoeber et al., 2016).

In the absence of CAVIN1, Cav1 is localized to non-caveolar membrane domains known as Cav1 scaffolds (Lajoie et al., 2009). Previously, application of machine learning and network analysis to SMLM data sets for Cav1 in PC3 prostate cancer cells, that express Cav1 but no CAVIN1 and therefore no caveolae (Hill et al., 2008), identified two classes of Cav1 scaffolds corresponding to small Cav1 homo-oligomers (S1 scaffolds) (Monier et al., 1995; Sargiacomo et al., 1995) as well as larger hemispherical S2 scaffolds (Khater et al., 2018). The formation of curved Cav1 structures in the absence of CAVIN1 supports a role for Cav1 in membrane curvature as suggested by studied of the heterologous expression of Cav1 in bacteria (Ariotti et al., 2015; Walser et al., 2012). Larger hollow caveolae were only detected upon transfection of PC3 cells with CAVIN1 (PC3-PTRF cells) (Khater et al., 2018) and their modular nature supported the polyhedral Cav1 coat structure observed by cryoEM (Ludwig et al., 2016; Stoeber et al., 2016).

SMLM network analysis was applied to endogenous caveolae and scaffolds in HeLa cells labeled using primary anti-Cav1 antibodies and Alexa647 conjugated secondary antibodies. To enhance localization precision, a SMLM microscope equipped with real-time nanometer-scale drift correction hardware (Tafteh et al., 2016a) was used, a time-domain filter was applied to remove blinks whose lifetimes have overlapped (Tafteh et al., 2016b) and only high photon yield blinks were included to improve localization accuracy (Foi et al., 2008; Thompson et al., 2002). Localization precision with this in-house built SMLM microscope approaches 10 nm (Liu et al., 2018). Improved resolution of the approach has identified sub-modules within S1 scaffolds that correspond to the polygons observed in the Cav1 coat by cryoEM (Ludwig et al., 2013; Ludwig et al., 2016; Walser et al., 2012). S1A scaffolds correspond to stable Cav1 homo-oligomers detected biochemically (Monier et al., 1995; Sargiacomo et al., 1995). Modularity analysis and group matching shows that S1A scaffolds can dimerize to form S1B scaffolds and oligomerize to form hemispherical S2 scaffolds. S1B scaffolds match the modules that make up the caveolae coat suggesting that the caveolae coat is built progressively by dimerization of S1A scaffolds, composed of the basic polygonal Cav1 units, that combine to form a polyhedral caveolae coat.

Materials and Methods

SMLM Imaging

Hela cells were cultured in Dulbecco's Modified Eagle's medium (Invitrogen) complemented with 10% fetal bovine serum (Invitrogen). All cells were tested for *mycoplasma* using PCR kit (Catalogue # G238; Applied Biomaterial, Vancouver, BC, Canada). Cells were plated on coverslips (NO. 1.5H; coated with fibronectin) for 24 h before fixation. Cells were fixed with 3% paraformaldehyde (PFA) for 15 min at room temperature, rinsed with PBS/CM (phosphate buffered saline complemented with 1 mM $MgCl_2$ and 0.1 mM $CaCl_2$), permeabilized with 0.2% Triton X-100 in PBS/CM, and blocked with PBS/CM containing 10% goat serum (Sigma-Aldrich Inc.) 1% bovine serum albumin (BSA; Sigma-Aldrich Inc.). Then the cells were incubated with the primary antibody (rabbit anti-caveolin-1; BD Transduction Inc.) for 12 h at 4° C. and with the secondary antibody (Alexa Fluor 647-conjugated goat anti-rabbit; Thermo-Fisher Scientific Inc.) for 1 h at room temperature. The primary and secondary antibodies were diluted in SSC (saline sodium citrate) buffer containing 1% BSA, 2% goat serum and 0.05% Triton X-100. Cells were washed extensively after each antibody incubation with SSC buffer containing 0.05% Triton X-100. Post-fixation was applied using 3% PFA for 15 min followed by extensive washing with PBS/CM. For the analysis of Hela cells, near-infrared fiducial markers (diameter 100 nm; Thermo Fisher Scientific) were added for the real-time drift correction.

Before imaging, the imaging buffer was freshly prepared with 10% glucose (Sigma-Aldrich Inc.), 0.5 mg/ml glucose oxidase (Sigma-Aldrich Inc.), 40 µg/mL catalase (Sigma-Aldrich Inc.), 50 mM Tris, 10 mM NaCl and 50 mM β-mercaptoethylamine (MEA; Sigma-Aldrich Inc.) in double-distilled water (Dempsey et al., 2011b; Huang et al., 2008). The cells were immersed in the imaging buffer and sealed on a glass depression slide.

Imaging of Hela cells was performed on a home-built SMLM system equipped with an apochromatic TIRF oil immersion objective lens (60×/1.49; Nikon Instruments) and a real-time drift correction system which limits the lateral drift to ~1 nm and the axial drift to ~2.5 nm. A 639 nm laser line (Genesis MX639, Coherent Inc., USA) was used for the excitation of the Alexa Fluor 647 fluorophores and near-infrared fiducial markers. A 405 nm laser line (Laserglow Technologies) was used for the activation of the Alexa Fluor 647 fluorophores. The detailed optical setup and the imaging acquisition procedure were described previously (Tafteh et al., 2016a; Tafteh et al., 2016b).

Multi-Proximity Threshold Network Modularity Analysis

For every blob of 3D localizations, more than one network can be constructed; one per each proximity thresholds in the set $\{PT_1, PT_2, \ldots, PT_T\}$. I.e. $blob_i$ has T networks $\{G_i^1, G_i^2, \ldots, G_i^T,\}$, where $G_i$ is composed of a set of nodes $V_i$ and edges $E_i^1$ to form $G_i^1$ ($V_i, E_i^1$). $V_i$, unaffected by $PT_t$, represents the molecules of $blob_i$ and $E_i$ is the set of edges connecting all pairs of molecules interacting within $PT_t$ nm.

Given a blob's network, the optimal number of modules (communities) using eigenvectors of the network adjacency matrix was found. The blob's network was one connected component to ensure the optimal modules are obtained. The spectral algorithm was leveraged to decompose the adjacency matrix into modules. Specifically, we utilized the Newman method (Newman, 2006a; Newman, 2006b), where the optimization problem of finding the modules of one blob is to maximize the intra-connectivity between the Cav1 molecules within a module and minimize the inter-connectivity between the Cav1 molecules across the modules.

Results and Discussion 3D point clouds from 10 HeLa cells were processed using the 3D SMLM Network Analysis computational pipeline (Example 1). FIG. 12A shows the 3D point cloud of one of the HeLa cells in the dataset at various stages of the pipeline: 1) Noise filtering comparing degree network measure with a random network to filter out noisy blinks and monomeric Cav1, retaining clustered Cav1; 2) Segmentation into separate blobs and extraction of a 28-feature vector for every blob; 3) Unsupervised machine learning to learn the various Cav1 domains from the extracted blobs and their descriptor features. Machine learning identified four groups of Cav1 domains (H1, H2, H3, and H4) in HeLa cells. The Euclidean distance in 28 dimensions was used to encode similarity of HeLa groups with groups previously identified in PC3 and PC3-PTRF cells (Khater et al., 2018), with similarity proportional to the inverse Euclidean distance. As seen in FIG. 12B, for the larger groups, H2 matches PP2, corresponding to caveolae, and H1 matches PP1, corresponding to the larger hemispherical S2 scaffolds. For the smaller S1 scaffolds, H4 matches PP3 and H3 matches PP4. Distribution of the different classes of blobs in the different cell types shows that HeLa and PC3-PTRF present a similar distribution of Cav1 blobs with slightly more caveolae detected in HeLa cells (FIG. 12C).

Tunable Iterative Merge Module

Figure 13A:
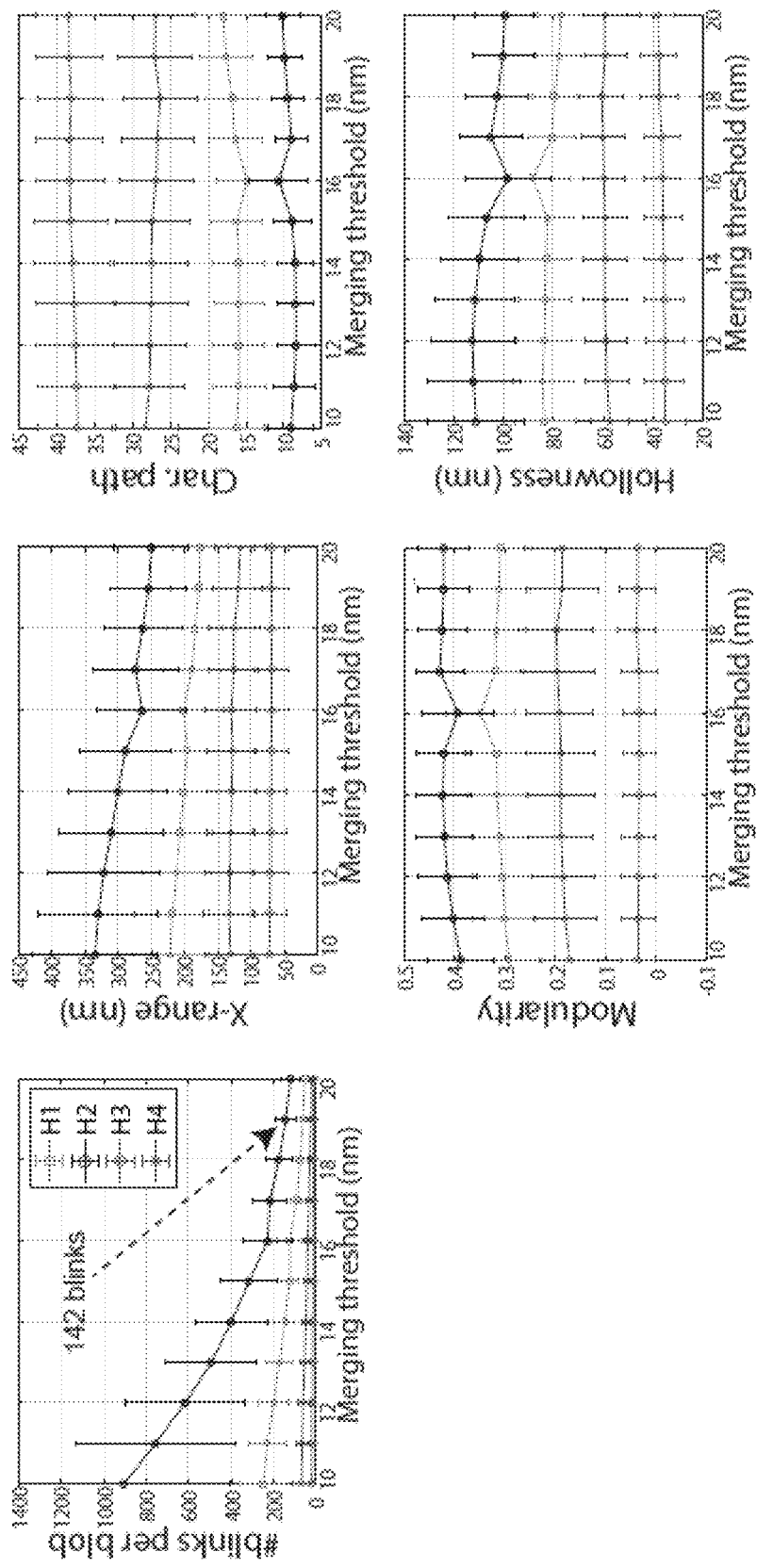
Figure 13B:
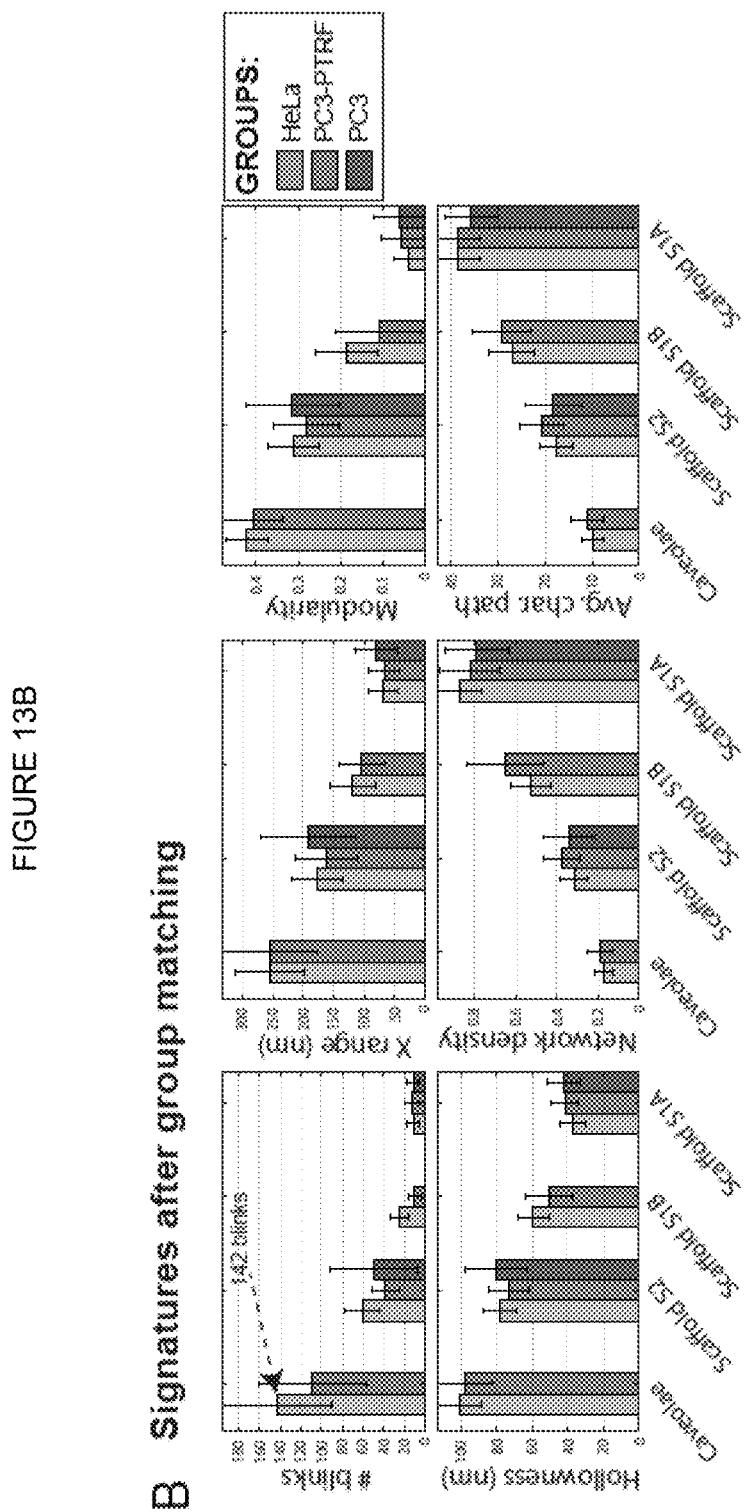

A fixed merge PT of 20 nm was previously applied and now applied PTs from 10-20 nm in steps of 1 nm. Importantly, tuning blink merge PT distance from 10-20 nm minimally impacted classification, size, modularity, characteristic path and hollowness of all 4 classes of blobs (FIG. 13A). Indeed, analysis of all 28 features showed minimal impact of the merge PT on any feature, except, not unexpectedly, molecular localization number per blob (FIG. 13B). Machine learning based blob classification is therefore independent of the merge module.

The merge PT was set based on the reported 145 Cav1 proteins per caveolae (Pelkmans and Zerial, 2005). A merge distance of 19 nm resulted in an average of 142 blinks for the H2 blobs, that match the PP2 caveolae blobs from PC3-PTRF cells (FIG. 12C). Feature analysis after group matching shows that the four HeLa groups match the four PC3-PTRF groups as well as the S2 and S1A scaffolds present in PC3 cells with high degree (FIG. 13B). A doubling in molecular localizations for S2B scaffolds relative to S1A scaffolds and increased modularity of S1B scaffolds in the HeLa data set was observed that may be attributed to the improved resolution obtained with the real-time drift control SMLM. Increased Cav1 localization number in S1B scaffolds parallels the increased size (X-range) and reduced density of these clusters relative to S1A scaffolds, reflecting differences between these structures that led to their classification as distinct cluster groups in this and our previous analysis. Indeed, a progressive increased number of localizations (Caveolae>S2 Scaffolds>S1B scaffolds>S1A scaffolds) associated with increased modularity and decreased density (FIG. 13B) was observed. Caveolae are the most modular structures (modularity>0.4), then S2, and S1B. S1A scaffolds have the least tendency to form modules (modularity<0.04).

Small Cav1 S1 Scaffolds Combine to Build Larger Scaffolds and Caveolae

Figure 14A:
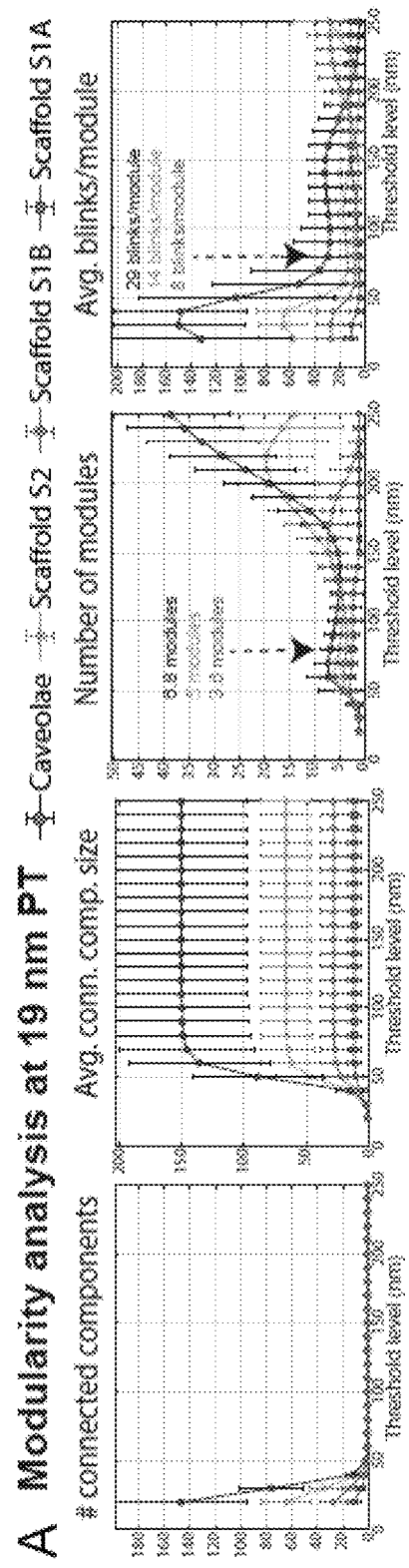
Figure 14B:
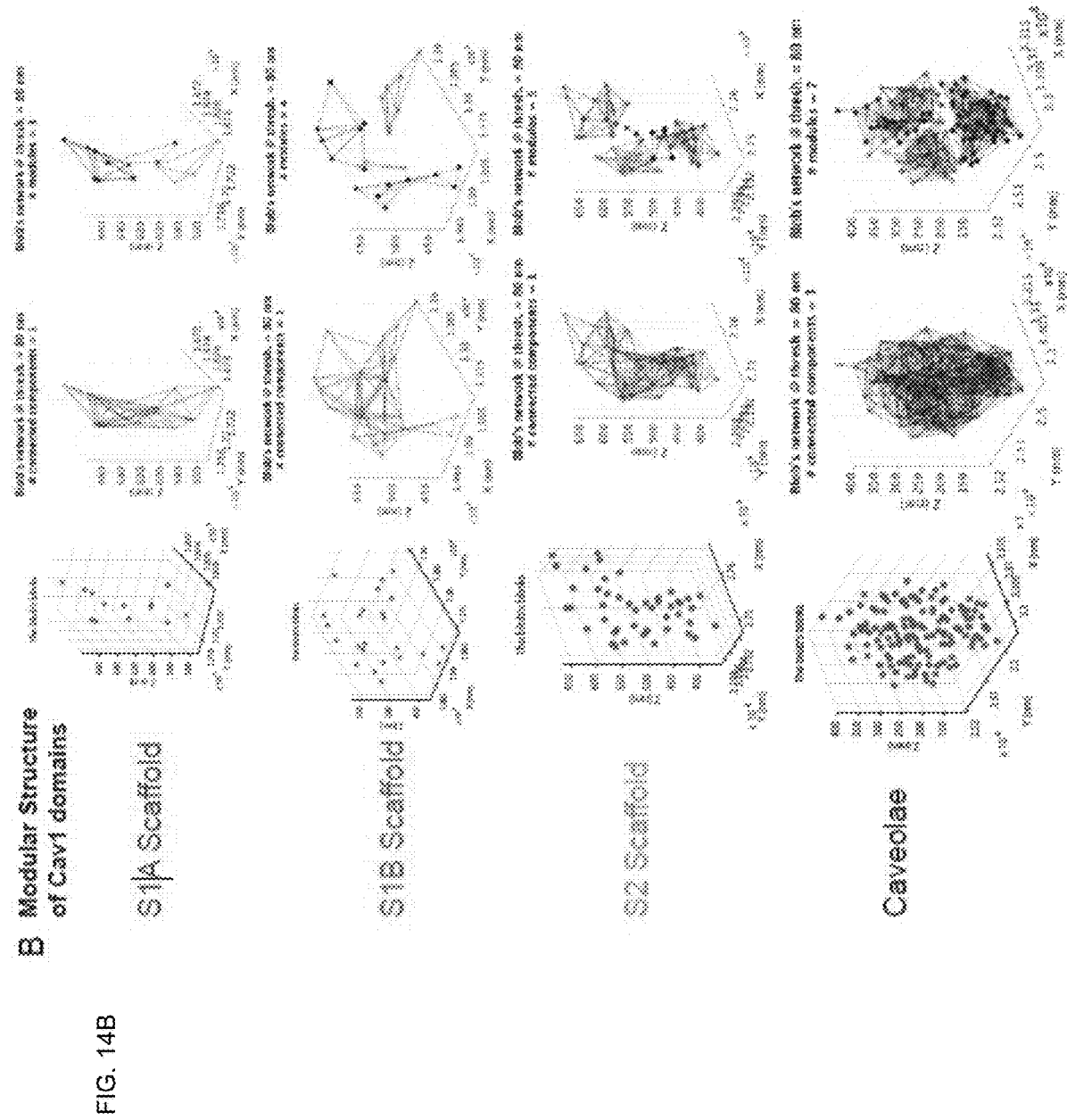

In view of the variable modularity of the different classes of Cav1 blobs, the blobs' modules were extracted and their features studied. A multi-proximity threshold (PT) network analysis (FIG. 14A) was used to decompose the blobs' networks into modules using spectral analysis. For all the groups, any PT greater than 60 nm renders every blob a single connected component; the average connected component size plateaus and equals the blob size for the different groups at PTs greater than 60 nm. This indicates that at PT>60 nm, all post-merge Cav1 localizations in a cluster are within 60 nm of each other. The number of modules and the number of Cav1 localizations per module are stable across the PT range from 60 to 170 nm. This range is therefore suitable to determine number of modules and number of Cav1 localizations per module. HeLa caveolae were found to be highly modular containing 6-7 modules of ~29 Cav1 localizations, S2 scaffolds 5 modules of ~14 localizations and S1B scaffolds ~4 modules of 8 localizations each (FIG. 14A). S1A scaffolds have the minimum average number of modules of ~2 modules per blobs of 7 localizations each.

Visualization of blobs from the identified groups (FIG. 14B) highlights the modular nature of the various Cav1 structures. At 80 nm, each blob forms one connected component network and extracted modules for every blob are shown in different colors. The presence of small modules (5-8 localizations) within both S1A and S1B scaffolds is indicative of an additional degree of suborganization within these small scaffold domains. 3D cryoEM tomography identified a network of 3-way junctions and polygonal arrangements of Cav1 protein densities within the caveolae coat (Ludwig et al., 2016). Similarly, cryoEM analysis of Cav1-induced vesicles in bacteria (h-caveolae) present distinct polygonal repeating units on the h-caveolae cage (Walser et al., 2012). The sub-modules that were detected in S1A and S1B scaffolds may correspond to these polygonal repeating units that comprise the caveolae coat. The fact that S1A scaffolds form one connected component unit and that the number of localizations of S1A scaffolds matches that of Cav1 homo-oligomers (~14-15 Cav1s) (Monier et al., 1995; Sargiacomo et al., 1995) suggests that interaction between these polygonal sub-modules forms more stable structural units.

Figures 15A, 15B:
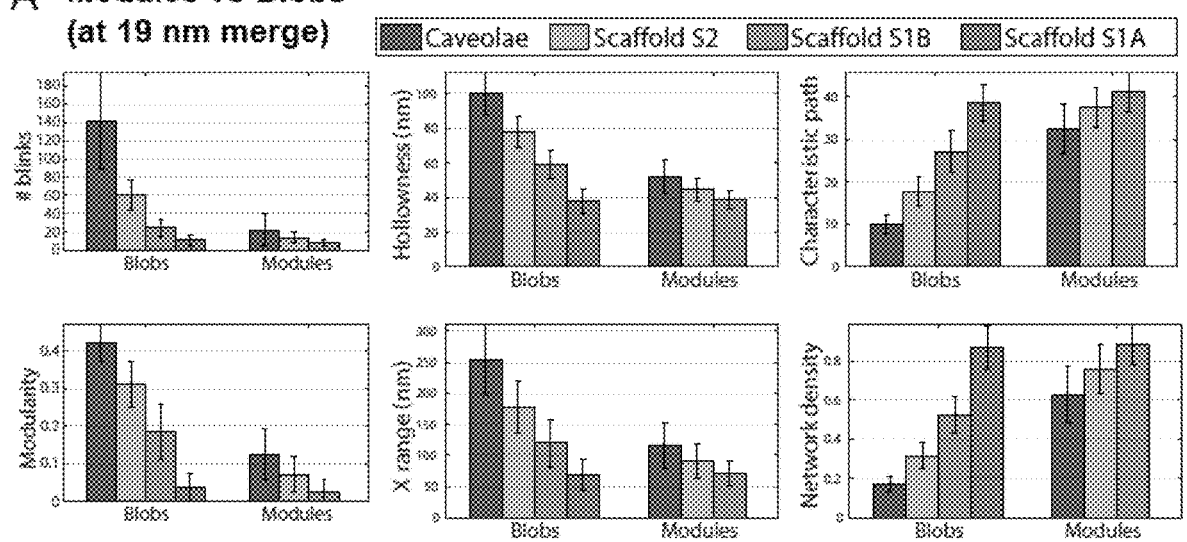

Most interestingly, the decomposed modules from the different Cav1 cluster groups show a much higher degree of similarity in terms of the shape, topology and network features than the clusters from which they originate (FIG. 15A). The similar network density of Cav1 modules but progressive reduction in network density from smaller to larger Cav1 domains argues that interaction between modules is responsible for the altered configuration of Cav1 in scaffolds and caveolae. This suggests that these modules may form fundamental building blocks of the larger Cav1 groups.

Indeed, many features of caveolae modules matched S1B scaffolds while S2 and S1B modules match S1A scaffolds. For instance, # localizations, hollowness, characteristic path, modularity, size, and network density of the caveolae modules (blue bars to right of graphs) are very similar to their corresponding features in the S1B blobs (magenta bars to left) (FIG. 15A). Module-blob similarity were accessed across all features using the matching matrix of the features for the various blobs and modules group center using Euclidean distance. The column-wise (i.e. the modules) similarity shows that: S2 scaffold modules match S1A blobs, caveolae modules match S1B blobs, and S1B modules match S1A blobs. The close matching of S1B modules with S1A blobs and doubling in number of modules and localizations of S1B modules relative to S1A blobs indicates that S1B scaffolds represent dimers of S1A scaffolds.

Overall, the data supports a model in which Cav1 is organized into smaller units of 5-8 Cav1 localizations that correspond to the polygonal base units observed by cryoEM analysis of the Cav1 caveolar coat (Ludwig et al., 2016; Walser et al., 2012). These base units combine to form larger stable structures of which the smallest is S1A scaffolds, that we propose correspond to the previously identified ~14-15 Cav1 homo-oligomers (Monier et al., 1995; Sargiacomo et al., 1995). We also identify S1B scaffolds, previously classified as distinct from S1A scaffolds, as larger structures that correspond to S1A dimers. Modularity analysis and group matching shows that S1A scaffolds combine to form both S1B dimers and the larger hemispherical S2 scaffold structures. Caveolae modules show better matching and correspond in size to S1B and not S1A modules suggesting that caveolae formation may be a two-step process in which S1A scaffolds first combine to form dimers that then interact to form the caveolae coat (FIG. 16). Consistent with a role for S1B in caveolae formation, PC3 cells that lack caveolae and CAVIN1 do not contain S1B scaffolds. The progressive reduction in density of Cav1 domains, but not of their constituent modules, as cluster size increases suggests that interaction between smaller S1 scaffolds to form larger structures, including caveolae, is associated with changes in how modules interact and are organized.

Importantly, the analysis based on TIRF microscopy argues that all 4 Cav1 domains, from S1A scaffolds to caveolae are present at the plasma membrane. Based on the reported kiss-and-run association of caveolae with the plasma membrane and their role as membrane buffers that flatten in response to mechanical stretching (Pelkmans and Zerial, 2005; Sinha et al., 2010), we suggest that these modular interactions are dynamic and reversible.

Example 3: Identification of Caveolin-1 Domain Signatures Via Graphlet Analysis of Single Molecule Super-Resolution Data Introduction Graphs are ubiquitous and powerful mathematical structures used for modeling objects and their interactions. Graph-based network analysis have been used in many fields of study and helped in understanding the behavior of many systems. The network is a set of items known as nodes, with connections between them, known as edges (Newman, 2003). There are many successful realworld examples of leveraging network in analyzing social, computer, brain, and biological networks (Newman, 2003, Bassett and Sporns, 2017, Krivitsky et al., 2009, Costa et al., 2008, Zitnik and Leskovec, 2017, Brown et al., 2014). Recently, a graph-based complex network analysis clustering method (Khater et al., 2018) was used to analyze the 3D point cloud of single molecule localization microscopy (SMLM) super resolution microscopy data. The method consists of an integrated pipeline that can be used to correct for multiple blinking artifact, filter the noise out, segment the clusters, analyze the clusters and identify them automatically using machine learning approaches. Application of unsupervised learning network analysis and machine learning to caveolin-1, the coat protein of cell surface caveolae invaginations, reported a modular structure for caveolae, similar to that determined by cryoEM (Stoeber et al., 2016, Ludwig et al., 2016), as well as three non-caveolar scaffolds, including a previously unreported hemispherical scaffold domain (Khater et al., 2018). Caveolae invagination requires the adaptor protein CAVIN-1 (also called PTRF) and here we apply supervised learning approach using a PTRF mask to identify PTRF-associated CAV1 domains and use graphlet analysis to classify and compare the Cav1-labeled domains.

Many methods have been deployed to extract features from point clouds, either via hand-crafted features or automatically derived features via deep learning, for different machine learning tasks such as segmentation and classification (Gumhold et al., 2001, Qi et al., 2017). Moreover, point cloud data has several popular representations (e.g. graph, mesh, image, and volumetric) for feature extraction and learning. Graph representation has been used to extract features for the machine learning tasks. Unsupervised learning was used (Zitnik and Leskovec, 2017, Grover and Leskovec, 2016) to extract the features of every node in graph-represented data. Graphlets and motifs are two related concepts used to describe small patterns or subnetworks that occur in complex networks. Graphlets were introduced by Pržulj et al (Pržulj et al., 2004) as measures of local network structures. Graphlets are small connected non-isomorphic induced subgraphs of a large network (Pržulj, 2007). Network motifs, on the other hand, are the interconnected patterns that are significantly and highly recurrent in real-world networks compared with random networks (Milo et al., 2002). Consequently, graphlets and motifs are regarded as the basic building blocks for large networks and graphs. Decomposing large networks into their base graphlets and calculating the frequencies of their occurrences can provide robust features to differentiate between different networks and discover their underlying signatures. The graphlet patterns can vary based on the number of the nodes k and their connectivity in each subgraph. The number of patterns increase exponentially with k and hence increase the complexity of enumerating them in big-graphs. Typically, the graphlet patterns are extracted for k=2, 3, 4, and 5 nodes.

Moreover, finding some of the patterns are NP-hard problems (e.g. finding the clique of maximum size) and require efficient algorithms for counting them (Ahmed et al., 2015, Ahmed et al., 2017). Many methods have been proposed to find the graphlet patterns from the networks (Marcus and Shavitt, 2012, Hočevar and Demšar, 2014, Ahmed et al., 2015, Shervashidze et al., 2009). In particular, the parallel graphlet decomposition method (Ahmed et al., 2015, Ahmed et al., 2017) is very fast, scalable and supports extracting macro and micro graphlets features and counting both connected and disconnected graphlets.

Graphlets have been widely used for a myriad of applications such as network similarity, network alignment, biological and protein networks, prediction and classification, image segmentation, etc. (Pržulj et al., 2004, Pržulj, 2007, Dutta and Sahbi, 2017, Kollias et al., 2012, Bressan et al., 2017, Zhang et al., 2013, Shin et al., 2016, Shervashidze et al., 2009). Recently, the graphlets/motifs are exploited as a high-order connectivity patterns information for network clustering (Benson et al., 2016), and fast local graph clustering and community detection tasks (Yin et al., 2017). Here we apply graphlet analysis to SMLM point clouds and show that graphlets are highly efficient classifiers that distinguish caveolae from scaffolds. Comparison of unsupervised and supervised learning, using a PTRF mask, suggest that PTRF is associated not only with caveolae but also scaffold domains.

Material and Methods

Cell Culture, Immunofluorescent Labeling and SMLM Image Acquisition

PC3-PTRF cells were cultured in RPMI-1640 medium (Thermo-Fisher Scientific Inc.) complemented with 10% fetal bovine serum (FBS, Thermo-Fisher Scientific Inc.) and 2 mM L Glutamine (Thermo-Fisher Scientific Inc.). Cells were fixed with 3% paraformaldehyde (PFA) permeabilized with 0.2% Triton X-100 in PBS/CM, and blocked with PBS/CM containing 10% goat serum (Sigma-Aldrich Inc.) 1% bovine serum albumin (BSA; Sigma-Aldrich Inc.) prior to labeling with the primary rabbit anti-caveolin-1 (BD Transduction Labs Inc.) and mouse anti-PTRF (BD Transduction Labs) antibodies for >12 h at 4° C. followed by secondary antibody (Alexa Fluor 647-conjugated goat anti-rabbit; Alexa488-conjugated goat anti-mouse (Thermo-Fisher Scientific Inc.) for 1 h at room temperature, and pot-fixed with 3% PFA, as described previously.

GSD super-resolution imaging of 10 PC3-PTRF and 10 PC3 cells was performed on a Leica SR GSD 3D system using a 160× objective lens (HC PL APO 160×/1.43, oil immersion), a 642 nm laser line and an EMCCD camera (iXon Ultra, Andor), as described previously. The GSD event list was exported and processed by merge analysis at 20 nm, filtering, network analysis to identify Cav1 clusters and machine learning to define Cav1 clusters (PP1, PP2, PP3, PP4). A wide-field TIRF image of Alexa488-labeled PTRF was acquired for each of 10 cells in parallel and used as a mask to identify Cav1 clusters. The PTRF mask was processed by applying the morphological closing operation to rub off the small holes in the mask and then superimposed on the segmented Cav1 blobs to identify Cav1 blobs touching the mask as "in mask" and the others as "out mask".

Data
- 10 SMLM PC3 cells (14,491 blobs)
- 10 SMLM PC3-PTRF cells (10,866 blobs)
- 10 widefield PTRF masks that correspond the cells from PC3-PTRF population.

|  | PTRF+ | PTRF− | Total |
|---|---|---|---|
| PC3 | — | 14.491 | 14.491 |
| PC3-PTRF | 2136 | 8.730 | 10.866 |
| PC3-PTRF (≥60) | 857 | 10.009 | 10.866 |
| PC3-PTRF (<60) | 1.279 | 9.587 | 10.866 |

Graphlet Feature Extraction

Given a cell with N blobs, let blob, be the i-th blob with 3D coordinates $(X_i, Y_i, Z_i)$ of molecule localizations. $|blob_i|=I_i \times 3$, where $I_i$ is the number of molecules in $blob_i$. The input to the network construction of $blob_i$ are $(X_i, Y_i, Z_i)$ and a set of proximity thresholds $\{PT_1, PT_2, \ldots, PT_T\}$ and the output are blob,'s networks $\{G_i^1, G_i^2, \ldots, G_i^T\}$ at the different thresholds, where $G_i^t$ is composed of a set of nodes V, and edges $E_i^t$, i.e. $G_i^t=(V_i, E_i^t)$. Vi represents the molecules of $blob_i$ and $E_i^t$ is the set of edges connecting all pairs of molecules interacting within $PT_t$ nm.

D graphlet features for each of the resulting N×T networks from all the blobs at all thresholds were extracted using Parallel Graphlet Decomposition (PGD) (Ahmed et al., 2015, Ahmed et al., 2017). Blob biosignatures were identified by extracting the most discriminative graphlet features and corresponding proximity thresholds that best discriminates between the blob classes. PGD extracts three kinds of features: The macro (global) motif counts for the motifs with k=2, 3, and 4 nodes; the micro motif counts (extracted per each edge in the network); and the Graphlet Frequency Distribution (GFD) features. Given that the micro and macro features are dependent on the number of nodes in the network and since the number of molecules per blob (Ii) varies across the blobs, to avoid biasing the classification model to rely on number of molecules, the analysis was based on the GFD features (with k=4 nodes), since GFDs capture relative values (FIG. 17B).

The 4-node graphlets have 11 patterns (FIG. 17B) that can be arranged into connected and disconnected graphlets to extract GFD features (Rossi et al., 2017). The connected graphlets have 6 features ($g4_1, g4_2, g4_3, g4_4, g4_5, g4_6$) and disconnected graphlets have 5 features ($g4_7, g4_8, g4_9, g4_{10}, g4_{11}$). The GFD features can be extracted for the connected graphlets alone, the disconnected graphlets alone, and for both the connected and disconnected graphlets. For example, the GFD for the connected graphlet $g4_1$ can be calculated by using the equation $$GFD_{g4_1} = \frac{\text{count}(g4_1)}{\sum_{i=1}^{b} \text{count}(g4_i)},$$

where count($g4_1$) is the total number of recurrences of the pattern $g4_1$ in the network. That is, the GFD finds the frequency of a given pattern in a network relative to the other patterns.

Machine Learning Classification of the Blobs

The supervised machine learning task (classification) requires the feature vector for every blob as well as its class (ground truth GT label). The blobs classes were obtained using two different methods. Let Y1 be the classes obtained using the first blob's labelling method and Y2 are the classes when using the second labelling method. $|Y1|=|Y2|=n$, $y_{i1} \in [PTRF+, PTRF-]$ and $y_{i2} \in [PP1, PP2, PP3, PP4]$. Where yi is the class label for $blob_i$. For the PC3 population, the blobs can take only one label, PTRF−.

The goals from using the classification model are: 1) to automatically identify the blobs, 2) to build a learning model that can be used to label the blobs of unknown samples, and 3) to show that the blobs have differences and use the extracted features to identify the different blobs (Cav1 domains) signatures.

In all the classification experiments, the 10-fold cross validation strategy was used. A balanced number of blobs for the classification task was obtained by sampling. For example, the total number of positive blobs is 857. The same number is sampled from the negative blobs to have a balanced dataset.

The binary classification was divided into the following based on the source of the extracted blobs (FIG. 19A,C):

1) Classifying the blobs from PC3-PTRF data (positive VS negative blobs taken from the same population).

2) Classifying the blobs from both populations. Positive blobs taken from PC3-PTRF and the negative blobs taken from PC3. Where the PC3 population have pure PTRF− blobs.

3) Classifying the blobs from both populations positive blobs taken from PC3-PTRF and the negative blobs taken from PC3 (FIG. 20B), where the minimum # molecule per blob chosen to be ≥60 (excluding all the small blobs). This experiment shows that the graphlets features are very good features to discriminate between the blobs classes even when the # molecules in the negative class is the same as the number of molecules in the positive class. Which means that there are intrinsic properties in the negative features that made the classifier discriminate them using the subtle graphlets features.

The random forest classifier was used to classify the blobs based on the GFD features. The classification accuracy, specificity, and the sensitivity are reported at each proximity threshold.

Multi-Class Classification

Sensitivity and specificity are generally used to measure the performance of the binary classifiers. The sensitivity and the specificity measures for the multi-class classification from the confusion matrix are $$\text{Sensitivity} = \frac{TP}{(TP + FN)}$$

and $$\text{Specificity} = \frac{TN}{(TN + FP)}$$

and calculate the values per class as seen in the confusion matrix, where it shows an example of finding the evaluation measures for PP3. Where, the TP is the true positive, FN is false negative, TN is true negative, and FP is the false positive. For PP3 class, $FP_{PP3}=E_{PP1PP3}+E_{P2PP3}+E_{PP4PP3}$, and $FN_{PP3}=E_{PP3PP1}+E_{PP3PP2}+E_{PP3PP4}$, $TN_{PP3}$=all excluding $TP_{PP3}$, $FP_{PP3}$, and FNPP3. The same idea applied to calculate the sensitivity and specificity for the other classes (i.e. PP1, PP2, and PP4). The accuracy measure for the multi-class classification is calculated using the correctly classified blobs divided by the total number of blobs. Formally, using the confusion matrix $$\text{Accuracy} = \frac{TP_{PP1} + TP_{PP2} + TP_{PP3} + TP_{PP4}}{\text{Total number of blobs}}$$

Results

Figure 17A:
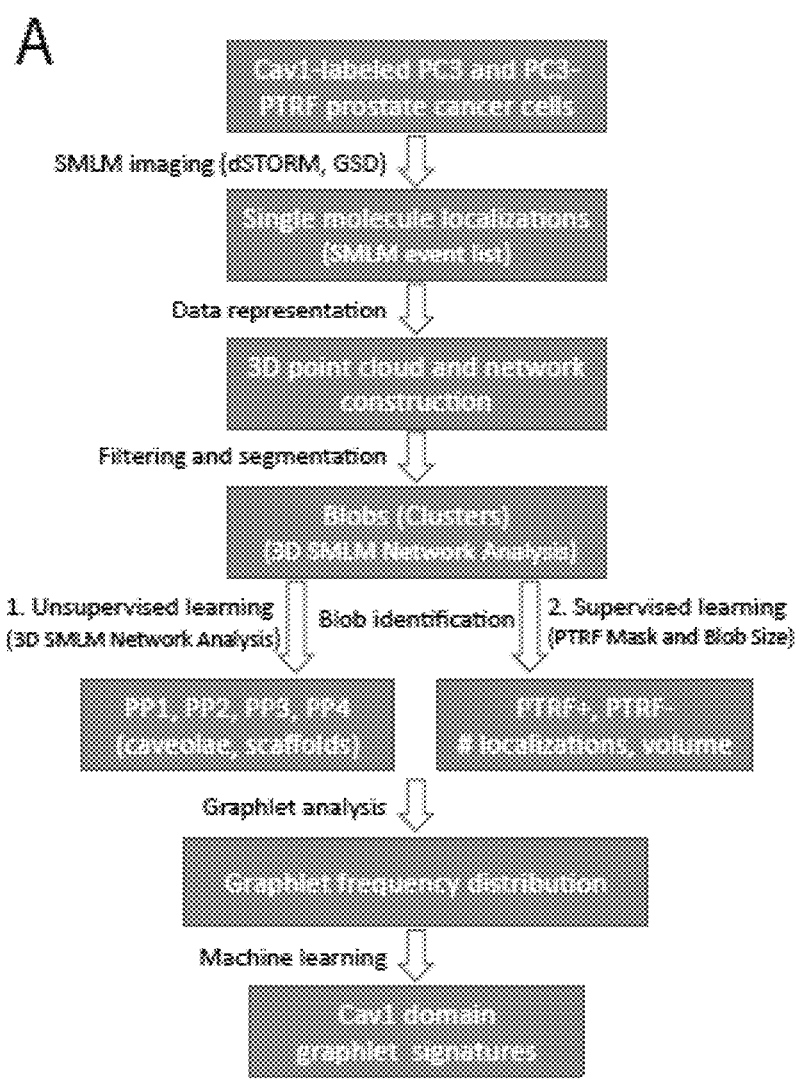
Figure 17B:
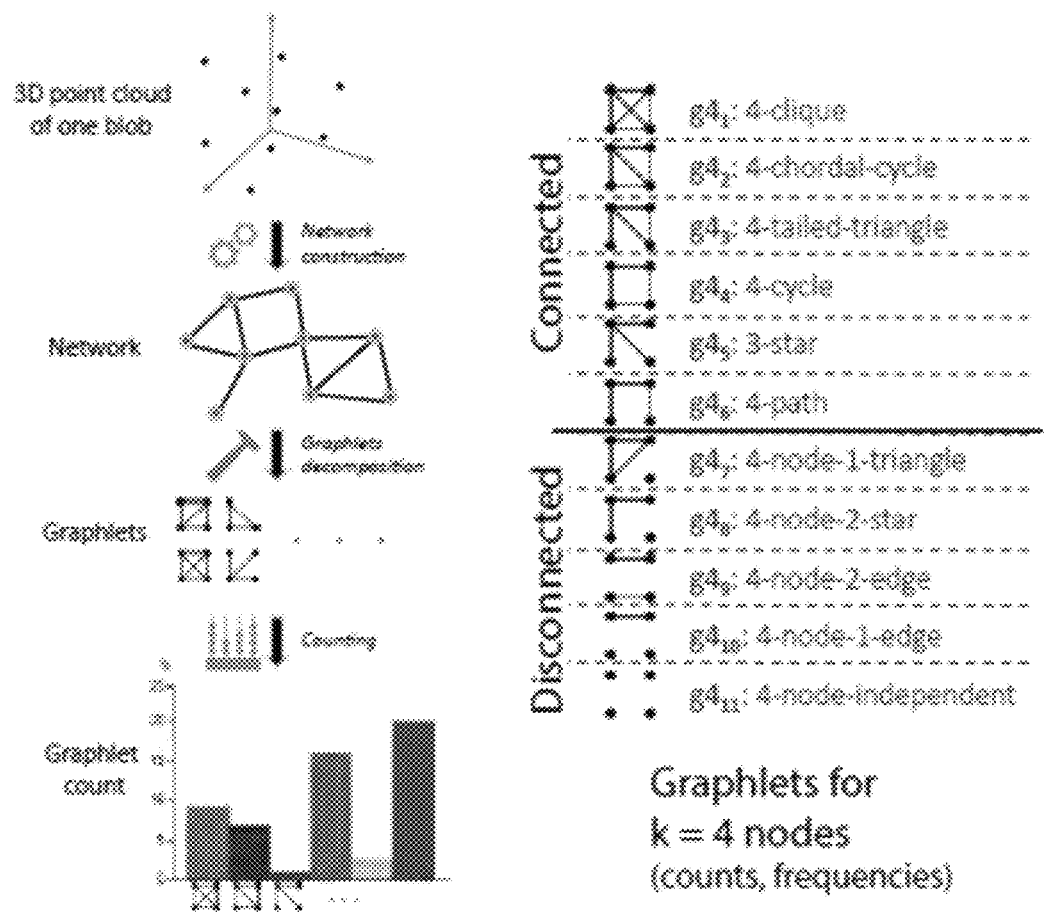
Figure 17C:
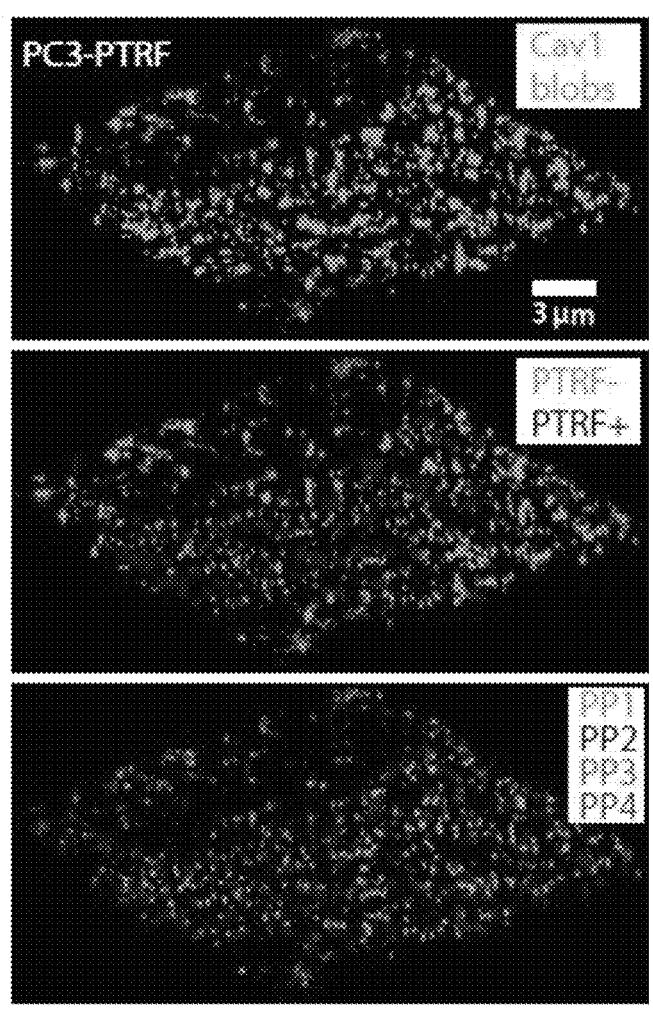
Figure 17D:
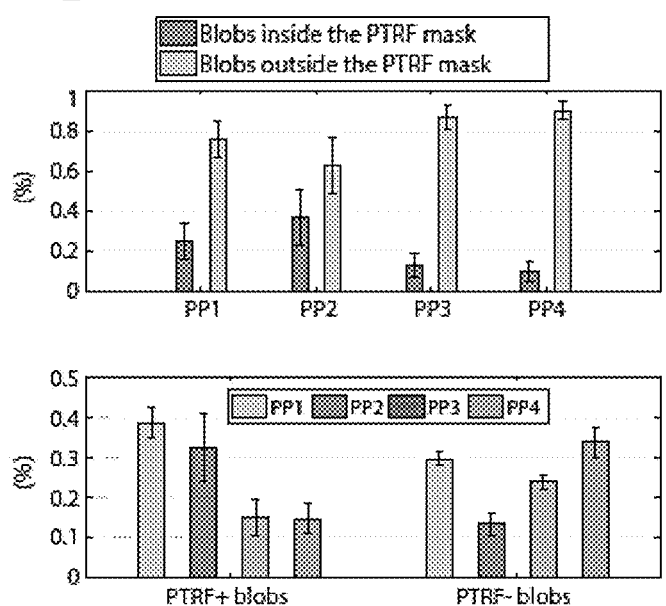

FIG. 17A shows an overview of the proposed framework for GFD classification of SMLM Cav1-labeled blobs. SMLM event lists of anti-Cav1 labeling of PTRF transfected PC3 prostate cancer cells are converted into 3D point cloud representation of blink locations in 3-dimensional space. Multiple blinking from single fluorophores and closely associated fluorophores is corrected, noise/background is filtered out and clusters identified as previously described (Khater et al., 2018). We then applied our established unsupervised learning approach based on topological, shape and network features to identify clusters as PP1 (S2 Scaffolds), PP2 (caveolae), PP3 (S1B scaffolds) or PP4 (S1A scaffolds) (Khater et al., 2018). Alternatively, a wide field PTRF mask for supervised learning in which blobs were classed as either "in mask" or "out mask" was used. Every blob is processed as shown in FIG. 1B, where a network is constructed for every blob and the different graphlet patterns are extracted for k=4 nodes. The graphlet patterns are then counted and used to find the graphlet frequency distributions for the connected and disconnected graphlet patterns of every blob. FIG. 17C shows representative images of all Cav1 clusters, Cav1 clusters in (PTRF+) and out (PTRF−) of the PTRF mask and unsupervised learning classification of blobs as PP1, PP2, PP3 or PP4. Quantification of blob distribution showed that all four classes of Cav1 blobs were present in and out of the PTRF mask, with PP2 caveolae more present in the PTRF+blobs, small PP3 and PP4 S1 scaffolds less present and hemispherical S2 scaffolds present amongst both PTRF+ and PTRF− blobs (FIG. 17D). In light of the heterogenous distribution of the various classes of Cav1 blobs in and out of the PTRF mask, the blobs were classified using random forest classification based on graphlet features.

Figure 18A:
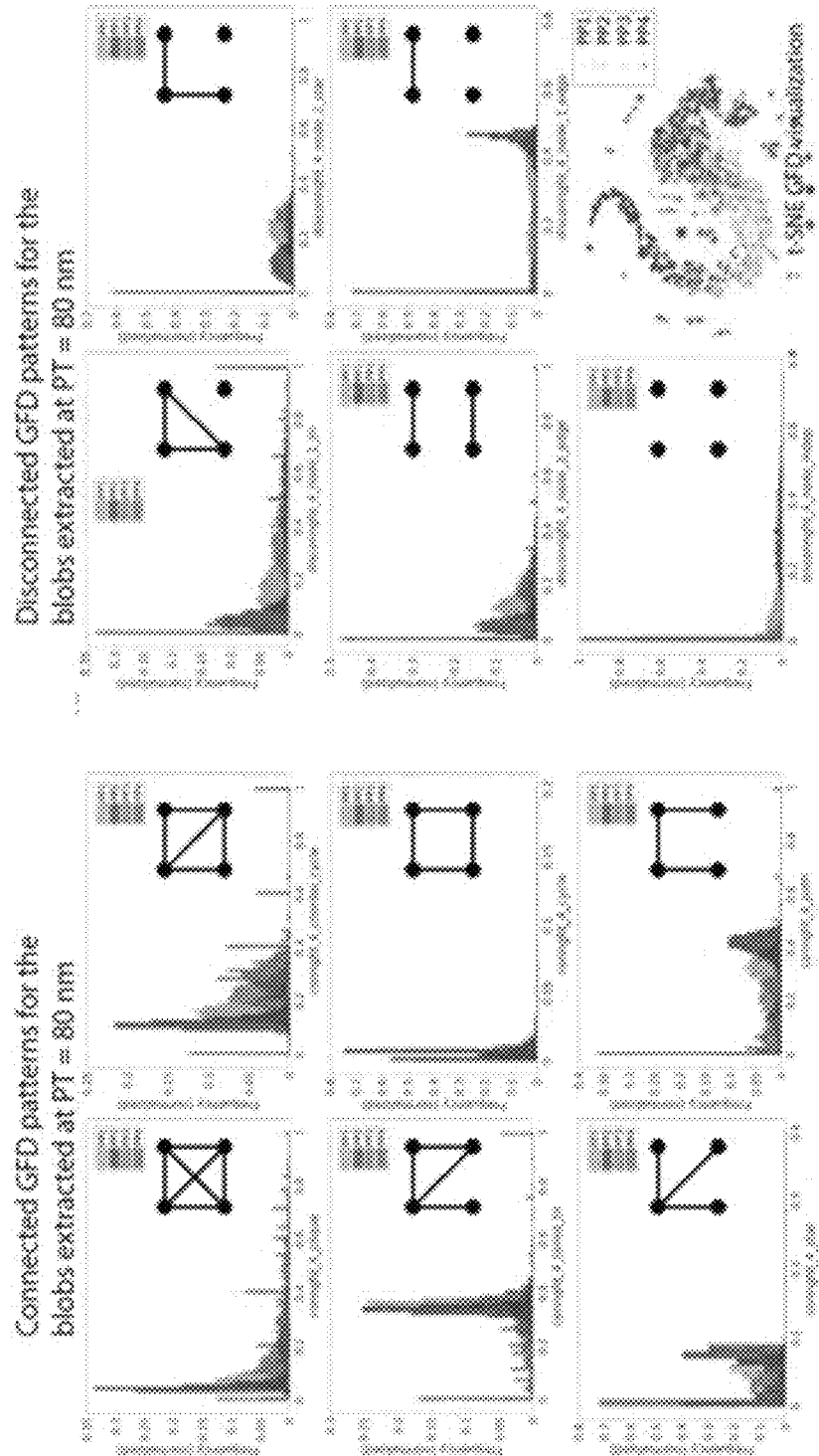
Figure 18B:
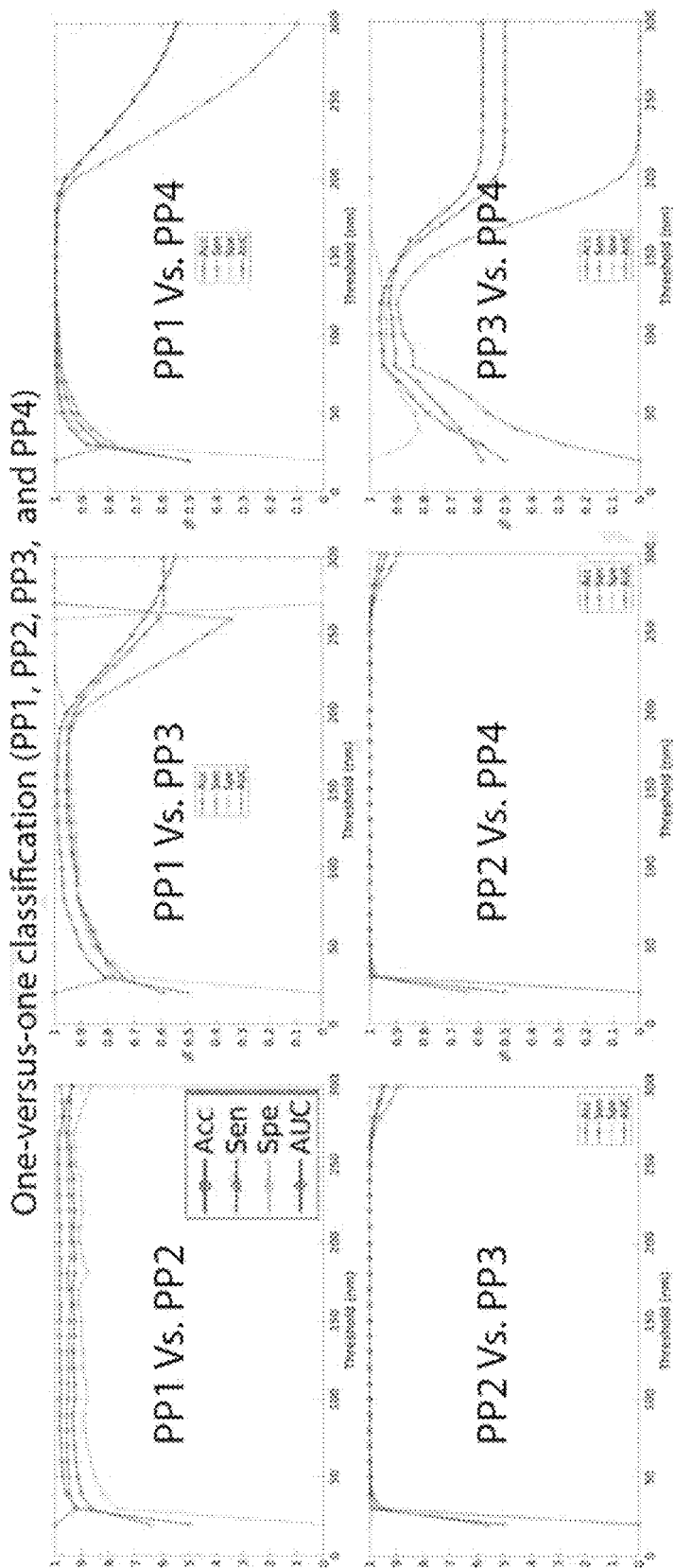
Figure 18C:
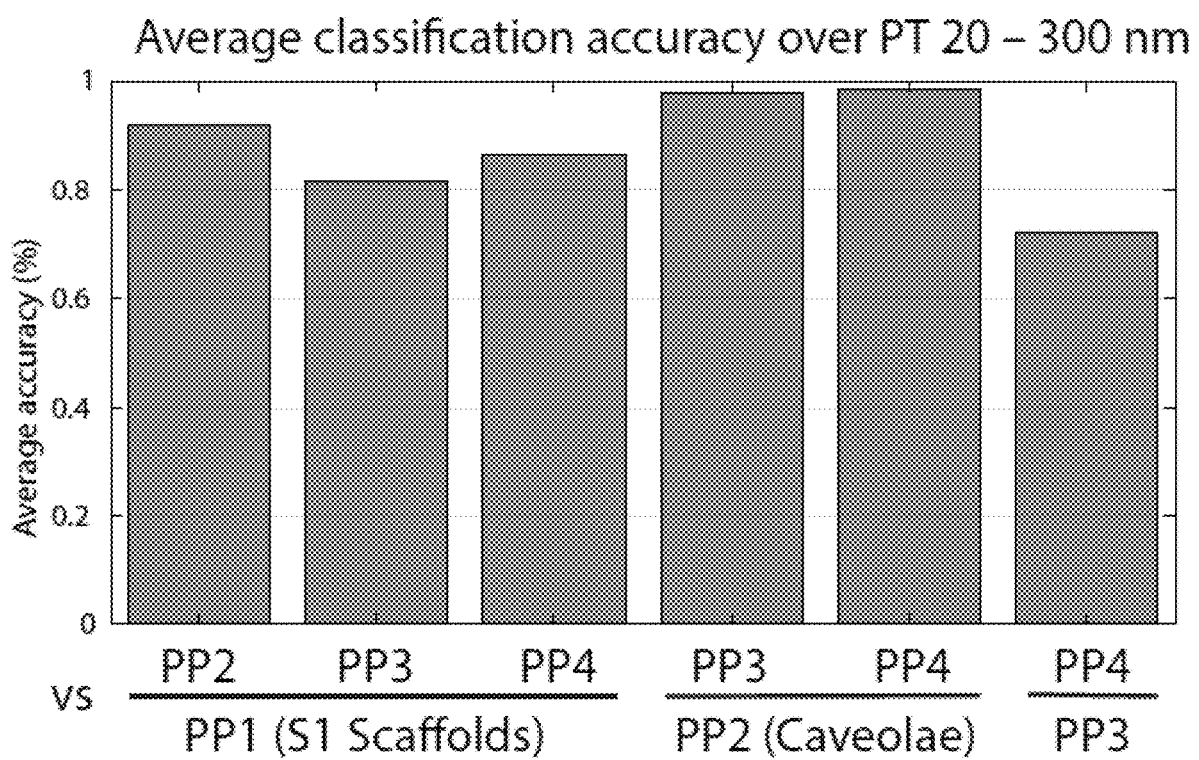

To extract the graphlet features, networks for every blob was constructed. The networks are constructed based on the proximity threshold between the pair of molecules within the blob. The nodes represent the molecules in the network, where the interaction between the neighboring molecules is represented as an edge (FIG. 17B). The Parallel Graphlet Decomposition (PGD) method (Ahmed et al., 2015, Ahmed et al., 2017) was leveraged to extract the graphlet features from the blobs' networks. The PGD method extracts macro (global) motif counts for the motifs with k=2, 3, and 4 nodes, micro motif counts, and the Graphlet Frequency Distribution (GFD) features. As the micro and macro features are highly dependent on the number of nodes in the network, we based our analysis on GFD features with k=4 nodes (FIG. 17B) so as not to bias our classification model between small and large blobs and analyzed GFD features regardless of the number of nodes in their corresponding networks. The extracted features are then used to classify the blobs. GFD analysis was applied to the 4 classes of Cav1 domains that had previously been identified in PC3-PTRF cells (PP1: S2 scaffolds; PP2: caveolae; PP3: S1A scaffolds; PP4: S1B scaffolds) based on topology, shape and network features (Example 1). As can be seen in FIG. 18A, frequency distributions for the 11 k=4 graphlets vary amongst the four classes of blobs, shown here at a proximity threshold of 80 nm. t-SNE is used to visualize the high-dimensional features by projecting them into a 3D or 2D space (low-dimensional space of features), where every point represents a blob after its features get projected into 2D space. t-SNE visualization for the GFD features clearly show distinct groups for PP2 caveolae, hemispherical S2 scaffolds and overlap between the similar and smaller PP3 and PP4 S1 scaffolds. One-versus-one (o-v-o) classification between the four groups (i.e. for M=4 groups, we will have:

$$N = \frac{M \times (M-1)}{2} = 6 \text{ classifiers}$$

was determined across proximity thresholds (PTs) from 20-300 nm, the minimal PT corresponds to the merge threshold applied and the maximum to the largest blob size. PP2 caveolae showed a high classification accuracy, sensitivity, specificity and AUC against all three scaffold groups (FIG. 18B). Classification accuracy was highest versus the S1 scaffolds (PP3, PP4) that were most poorly distinguished from each other (FIG. 18 B,C). Progressive increases between PP2 caveolae and S2 scaffolds and then S1 scaffolds is highlighted by the graph showing average classification accuracy over the 20-300 nm PT range (FIG. 18C). Use of graphlet feature based classification has therefore corroborated Cav1 cluster classification based on topology, size and shape features (Example 1). The one-versus-all classification was also used. The voting was used to combine the results of all the classifiers to get the multi-class classification accuracy. The results correspond to the o-v-o classification results. Moreover, the multi-class classification results show that the classification loss (which measures the predictive inaccuracy of classification) is <10% when the PT is between 50-160 nm. Which means that GFD features best discriminate and identify the Cav1 domains in 50-160 nm proximity. GFD classification was then applied to PTRF+ and PTRF− blobs. FIG. 19A shows the processing of the PTRF mask by applying the morphological closing operation to remove the small holes in the mask and superposition of the segmented Cav1 blobs on the PTRF mask for correspondence analysis. Using this method, Cav1 blobs touching the mask are "in" mask and the others "out" mask. Binary GFD pattern analysis shows a high degree of overlap between the PTRF+ and PTRF− classes for all graphlets. GFD similarity between the two classes is highlighted by the extensive overlap in the t-SNE visualization and the low (~65%) classification accuracy between the two groups (FIG. 19 B,C).

Figure 20A:
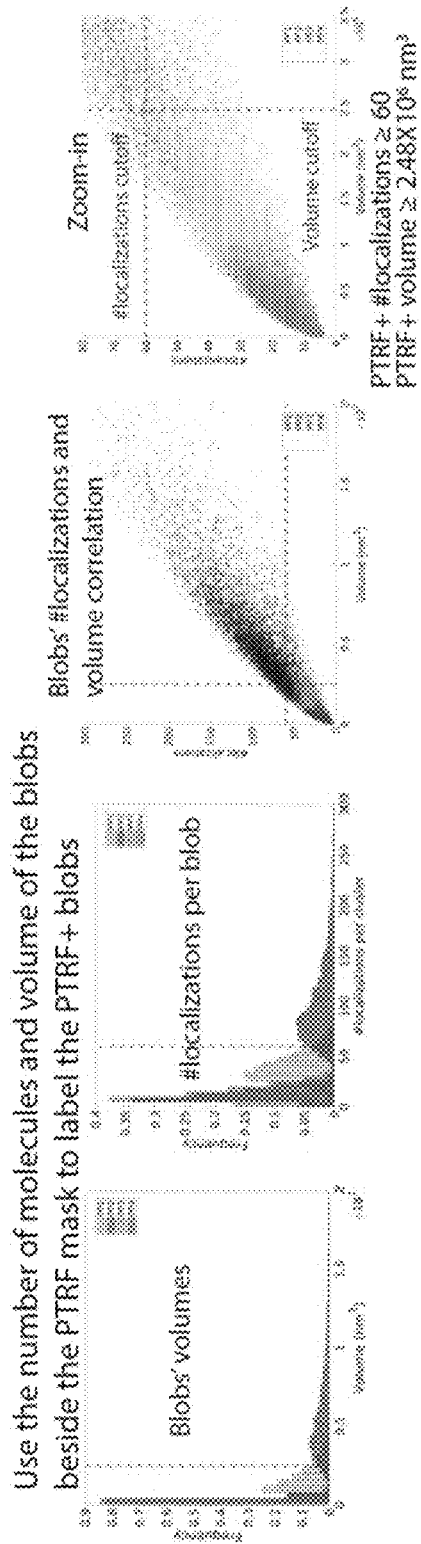
Figure 20B:
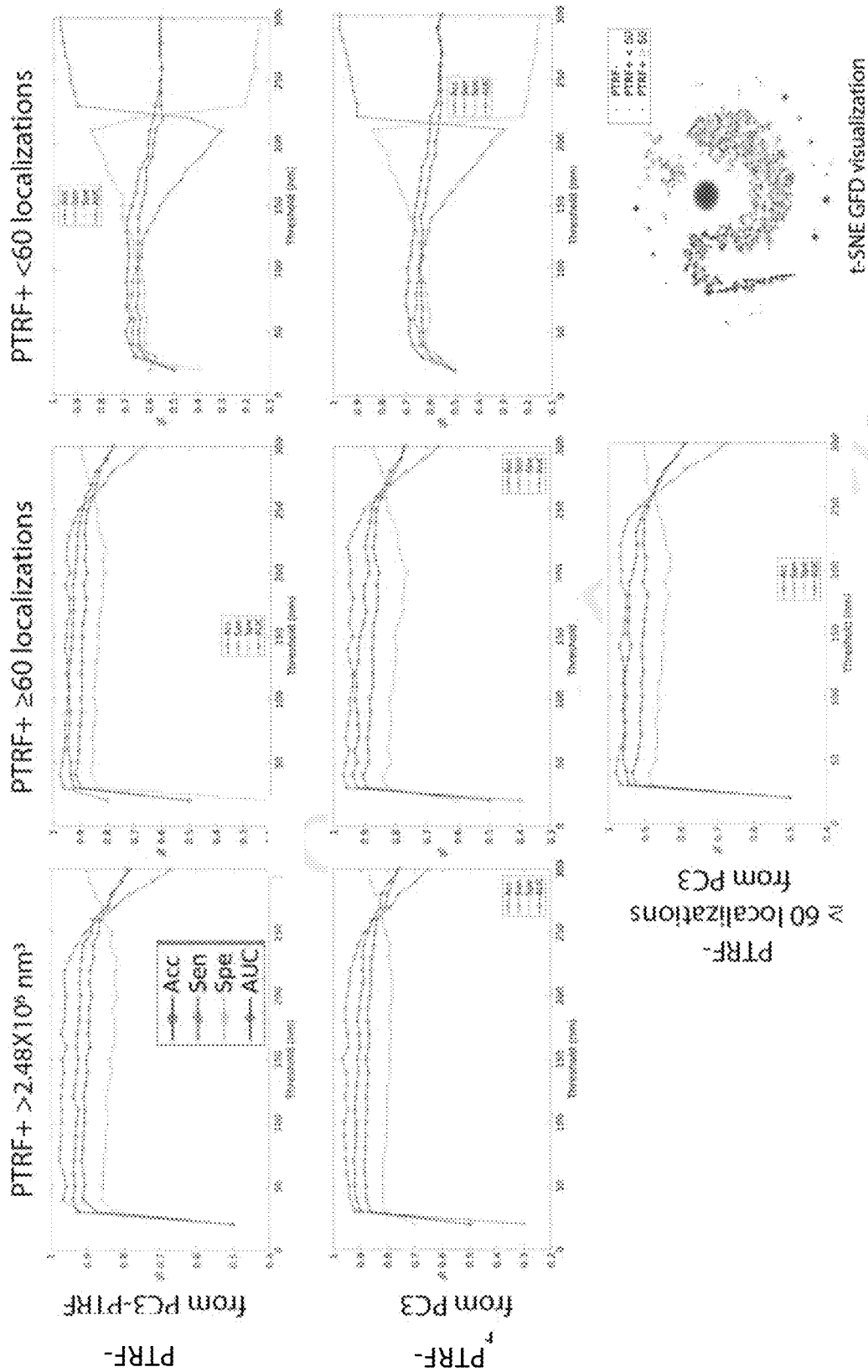

PTRF is required for caveolae formation and known to associated with caveolae (Hansen et al., 2013, Hill et al., 2008, Liu and Pilch, 2008). Caveolae are larger than scaffolds (Khater et al., 2018) and volume and # nodes analysis of the four classes of blobs defined by unsupervised learning identified a clear size demarcation between PP2 caveolae and the larger S2 scaffolds at $2.48 \times 10^6$ nm$^3$ and 60 nodes (FIG. 20A). This is consistent with Khater et al, 2018, where we reported that PP2 caveolae contained 109±52 predicted molecular localizations and had a minimum number of localization of =60. Correlation between # nodes and volume showed that ≥60 nodes clearly segregated PP2 caveolae (blue) domains from the three scaffold domains and that $2.48 \times 10^6$ nm$^3$ selected for the vast majority of PP2 caveolae but included some S2 scaffolds (green). Large PTRF-positive blobs (≥$2.48 \times 106$ nm$^3$) showed high classification accuracy with PTRF-negative blobs from PC3-PTRF as well with the complete set of Cav1 blobs from PC3 cells, that lack PTRF and caveolae (FIG. 20B). Similarly, PTRF-positive 60 node blobs showed high classification accuracy (i.e. >90%) with PTRF-negative blobs from PC3-PTRF cells and PC3 blobs; importantly, PTRF-positive 60 node blobs were accurately classified as distinct from ≥60 node blobs from PC3 cells highlighting that classification by GFD is not based on cluster size. PTRF-positive ≤60 node clusters showed poor classification accuracy (i.e. <65%) with PTRF-negative nodes. The improved classification accuracy due to volume and # node stratification is more clearly shown in the t-SNE plot (FIG. 20B) and the graph analysis of average classification accuracy over PT 20-300 nm (FIG. 20C). These results suggest that while association with the PTRF mask effectively identifies large caveolae, smaller Cav1 clusters (i.e. scaffolds) cannot be distinguished based on their association with the PTRF mask.

Classification similarity between the supervised and unsupervised learning approaches (FIG. 21) were compared. PP2 caveolae showed low classification accuracy (i.e. <45%) with the large PTRF-positive ≥60 nodes group and high classification with the small PTRF-positive and PTRF−PTRF-positive blobs (<60 nodes) closely match PTRF-negative blobs and show significant reduction in one connected and two disconnected graphlets. Similar analysis of the unsupervised learning groups shows that larger hemispherical S2 scaffolds (PP1) are most similar to caveolae (PP2) and that the smaller PP3 and PP4 scaffolds most closely match the PTRF-negative group (FIG. 21 C,D).

Figure 22A:
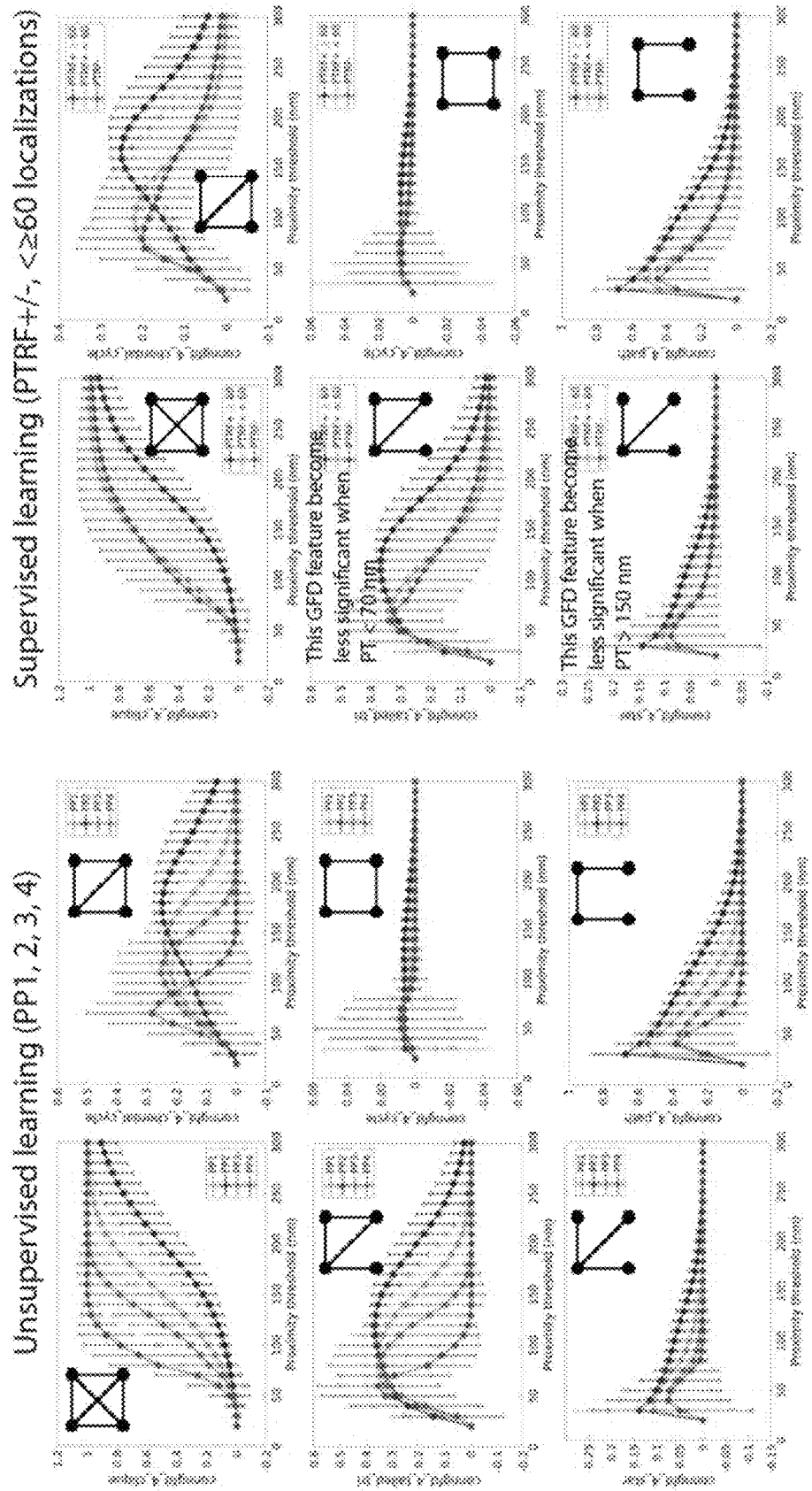
Figure 22B:
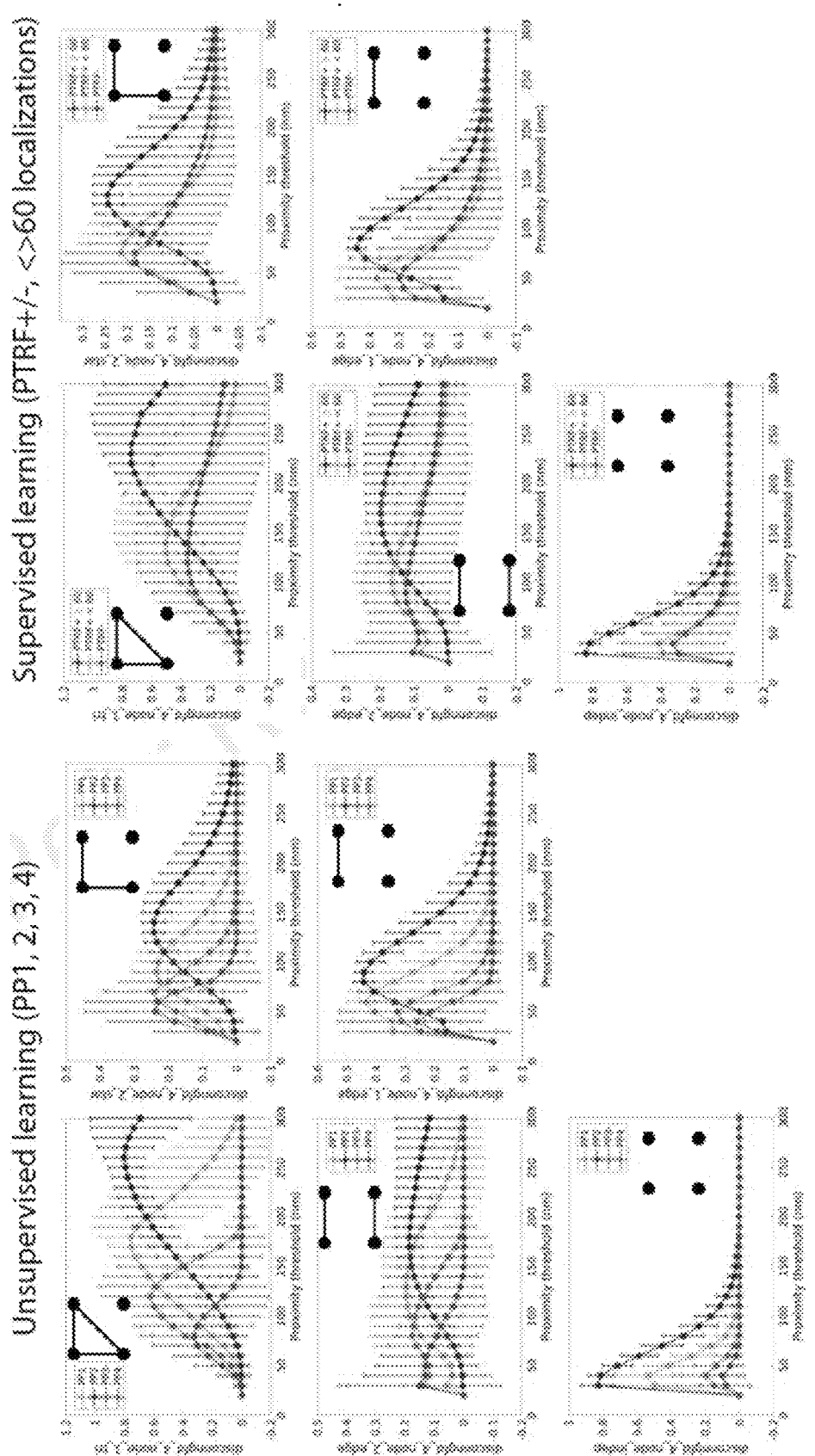

Caveolae show a high frequency of 4-path (g4$_6$) graphlets while small scaffolds show increased frequency of 4-clique (g4$_1$) and 4-chordal-cycle (g4$_2$) at low PTs that increase for all the domains with increasing PT in relation to blob size (FIG. 22A). Conversely, 4-node-independent are more frequent in large blobs at low PT and disappear from all blobs at high PT values. This highlights the high interconnectivity of nodes within Cav1 domains (FIG. 22B). Interestingly, all groups show a similar frequency of 4-tailed triangle (g4$_3$) at low PT whose decreasing frequency at higher PTs corresponds to blob size. Further, 4-cycle graphlets are absent from all Cav1 domains (FIG. 22A). In contrast, a high frequency (>60%) of 4-node-1-triangle (g4$_7$) disconnected and 4-tailed-triangle (g4$_3$) connected graphlet patterns in all Cav1 domains that vary in proportion to blob size was observed.

Discussion

Graphlet analysis of single molecule super-resolution data can be used to identify and discriminate Cav1 domains. The different Cav1 domains have distinct GFD patterns and features that is suggestive of altered molecular stoichiometry within these biological structures. Application of GFD analysis to SMLM data requires reduction of the millions of blinks obtained by SMLM to obtain representative molecular localizations. Each Cav1 molecule can be labeled by multiple primary and secondary antibodies, with the latter carrying multiple fluorophores. To do this, blinks were merged derived from individual Cav1 proteins by iteratively combining blinks within a defined 20 nm distance, generating a predicted Cav1 localization. (Example 1). Choice of merge threshold will necessarily impact the number of predicted localizations studied and use of a fixed 20 nm threshold will not necessarily take into consideration the reduced axial resolution of cylindrical lens-based 3D SMLM. Nevertheless, application of a 20 nm application to the SMLM data set obtained from PC3-PTRF cells effectively identified and distinguished caveolae from smaller scaffold structures (Example 1). Importantly, the caveolae identified showed structural similarities to those predicted by cryoEM (Stoeber et al., 2016, Ludwig et al., 2016).

The current study extended that work to include a wide-field mask for CAVIN1, a required adaptor for caveolae formation (Hill et al., 2008) and the demonstration here that GFD-based machine learning classifies PP2 caveolae Cav1 blobs with large (>60 nodes) CAVIN1-positive blobs confirms that the 3D SMLM Network Analysis pipeline, as applied here, can enable structural analysis of Cav1 domains. The low classification accuracy of CAVIN1+ and CAVIN1– blobs contrasts the high classification accuracy of PP1, PP2, PP3 and PP4 groups. Classification accuracy improved upon stratification of the CAVIN1+ blobs based on size, either number of nodes or volume. This suggests that smaller S1 and/or S2 scaffolds, also interact with the wide field CAVIN1 mask. While resolution of the wide-field CAVIN1 mask is significantly reduced relative to the SMLM-characterized CAV1 blobs, this data suggests that CAVIN1 is not exclusively associated with caveolae, but may also interact with Cav1 scaffolds.

The high classification sensitivity (or high true positive rate) (FIG. 18B, 20B) means that the classifier correctly identifies the PTRF+blobs, while at the same time the lower specificity (true negative rate) means that the PTRF– blobs are harder to identify and the majority of the mis-classified blobs are from the negative blobs. The specificity and sensitivity show that the positive blobs have less mis-predictions. The models with high sensitivity and low specificity are good for catching the actual positive cases.

The machine learning based classification of the various Cav1 domains with the graphlet analysis helped us to: 1) identify the Cav1 domains and draw their biosignatures and 2) find the best range of proximity thresholds to identify the significant molecular interaction (classification loss and mis-prediction is <10%) in each of the Cav1 domains. Classification accuracy is reduced at PTs below 50 and above 150 nm due to the less discriminatory GFD features at these ranges of PTs, which suggests that studying molecular interaction should not be performed at an arbitrary spatial scale since there is a critical range of spatial distances within which class-specific molecular interaction occurs.

Some of the molecular interaction patterns are more frequent than the other patterns in some of the structures which make them different (i.e. every biological structure type has unique patterns of its molecular interactions). For instance, the absence of 4-cycle graphlets and high frequency (>60%) of 4-node-1-triangle (g47) disconnected and 4-tailed-triangle (g4$_3$) connected graphlet patterns in all Cav1 domains is consistent with a polyhedral organization of Cav1 within caveolae and scaffolds, as indicated by cryoEM studies (Stoeber et al., 2016, Ludwig et al., 2016). Nevertheless, the high frequency of fully connected 4-clique graphlets in smaller CAVIN1-scaffolds at low PT is indicative of a high degree of interaction of Cav1 within the smaller scaffolds. Indeed, S1 scaffolds show significantly higher degree than S2 scaffolds or caveolae (Example 1). This suggests that Cav1 domains undergo progressive changes in interactions as they increase in size from S1 to S2 scaffolds and then to caveolae.

This study represents the novel application of graphlet analysis to point clouds generated from SMLM data sets. Graphlets represent features can be used to classify biological structures, define biosignatures associated with specific biological structures and identify molecular interaction motifs associated with specific biological structures. Extension of this approach to biological structures other than Cav1 domains is warranted.

Example 4: Drug Target Validation for Cystic Fibrosis

Cystic Fibrosis (CF) is the most frequent lethal genetic disease among Caucasians, afflicting ~3,600 Canadians. It is caused by mutations in CFTR (8-10), an ion channel that mediates chloride and bicarbonate transport by epithelia that line the airways, intestine, pancreatic ducts, sweat glands and other organs (11-14). Early studies revealed that F508del-CFTR is mislocalized and degraded at the ER (15,16) and that lowering temperature (28° C.) can partially restore F508del-CFTR trafficking to the plasma membrane (17). F508del-CFTR has altered surface distribution and domain association relative to wild-type CFTR. When rescued, F508del-CFTR channels are functional (18) although their open probability (19) and stability at the cell surface (20) are reduced compared to wild type CFTR. During the past 6 years there has been exciting progress in the development of therapeutics to target the basic ion channel defect in CF. Three CFTR modulators are currently in clinical use. Ivacaftor (VX-770 or Kalydeco®) is a potentiator that increases the open probability of CFTR. Lumacaftor (VX-809) and tezacaftor (VX-661) are pharmacological chaperones that correct the folding of F508del-CFTR and some other mutants (21,22). Kalydeco provides substantial improvement in lung function, increasing absolute mean forced expiratory volume in one second (FEV1) by ~11% within the first 30 days in patients with G551D. Nevertheless, lung function continues to decline despite Kalydeco treatment at about half the rate without the drug (23).

To treat individuals with the most common mutation F508del-CFTR and some other folding mutations, Kalydeco is combined with the corrector lumacaftor (VX-809) in a drug marketed as Orkambi® (24,25). Orkambi reduces exacerbations but provides only modest (~4.6%) improvement in FEV1. Moreover, some patients do not tolerate Orkambi and is ineffective or poorly effective on some mutants e.g. G85E and N1303K (26-29). Only 25% of cystic fibrosis (CF) patients carrying the F508del mutation in the cystic fibrosis transmembrane regulator (CFTR) respond to Orkambi, the only F508del-CFTR targeted drug in the clinic. Due to the prohibitive cost of Orkambi (>$250,000/year), CF treatments are not covered by provincial health insurance.

To identify CF patients responsive to Orkambi and other CF drugs, single molecule localization microscopy (SMLM) network analysis will be used to identify patient lung airway cells in which CF drug treatment specifically impacts CFTR structure. Identification of responsive CF patients at the protein level is important because patient-patient variation depends not only on genomic differences (e.g. modifier genes), but also on epigenomic and other factors that are not well understood. Studying responses directly at the level of the drug target will tailor and optimize therapies for individual patients, thereby increasing drug efficacy and substantially reducing the cost of treatment for all Canadian CF patients.

Methods:

Molecular architecture analyses of F508del-CFTR and native CFTR will be performed to define CFTR signatures for native CFTR conformation, partial misfolding and persistent misfolding. These signatures will be used to screen CF patient bronchial epithelial cells for responsiveness to CF modulator drugs.

Discriminating Normal and F508-delCFTR by SMLM Network Analysis (Y1)

Using SMLM network analysis and machine learning the structural changes in F508del-CFTR (90% of CF patients have at least one copy of F508del) and other class 2 mutants relative to wildtype receptor, with particular interest in those trafficking mutations that do not respond well to Orkambi (N1303K, A561E) will be determined. CFTR wild-type and mutant constructs will be expressed in primary bronchial epithelial cells using adenoviral vector whenever possible since they would have the most appropriate macromolecular complexes.

Identifying CFTR Antibodies for SMLM

The CFTR protein constructs are tagged with intracellular and extracellular epitopes, a biotinylation target sequence, and with fluorescent proteins (EGFP, mCherry). Analysis using various anti-tag antibodies will be performed including anti-GFP as well as anti-CFTR antibodies. Monoclonal and polyclonal antibodies against all cytoplasmic regions of CFTR are available, which constitute ~91% of the protein. Antibody specificity relative to CHBE cells will be first tested by confocal microscopy and then optimize dilutions for SMLM of the best anti-CFTR antibodies (3-5) using commercially available secondary Alexa-647 conjugated whole antibodies or Fab fragments (the latter having a reduced size and therefore improving resolution). The use of validated anti-tag antibodies will provide us with a reference framework that will allow us to assess the quality of the various anti-CFTR antibodies for SMLM analysis of CFTR. dSTORM acquisitions will be performed using fiducial markers on a SMLM microscope built that incorporates real-time nanometer-scale drift correction with significantly improved localization error (42). A time-domain filter will be incorporated to remove blinks whose lifetimes have overlapped (41) and perform analysis of data sets including cutoffs for different photon intensity levels. SMLM data will be acquired in both in 2D and 3D and will apply SMLM Network Analysis to both 2D and 3D event lists.

Identifying Network Features Specific to F508del-CFTR

CFTR has been reported to be monomeric (51) however Hanrahan and Wiseman found CFTR mobility is impacted by interaction with EBP50/NHERF1, reducing its mobility, as well as with the KCa3.1 potassium channel (52,53). Importantly, their recent data show that CFTR is recruited to sub-diffraction limit (i.e<250 nm) cholesterol dependent microdomains (i.e. lipid rafts) and reduced mobility (3,4), providing biophysical evidence for multiple CFTR populations. Recruitment of CFTR into these lipid raft domains is modulated by physiological secretagogues highlighting the physiological relevance of raft recruitment and clustering of CFTR. These CFTR populations should be readily detectable by SMLM (with a resolution of <20 nm) and classifiable using the 47-feature based machine learning analysis available to us. A single study applying SMLM to CFTR shows clearly the presence of CFTR clusters of several hundreds of nanometers in width and that removal of the C-terminal PDZ binding motif of CFTR alters CFTR cluster distribution (54), supporting the feasibility of the proposed approach.

The methods described in the previous examples will be applied to discover signatures for CFTR and mutants: to construct and describe CFTR networks; remove irrelevant blinks; capture remaining CFTR sub-networks (blobs); and then discover signatures of these blobs and the domains they belong to. An iterative blink merging algorithm merges blinks within 20 nm of each other, the resolution limit of the Leica SMLM, removing high degree (high interacting) points (i.e. from the same fluorophore or clusters of fluorophores). Virtual connections between the resulting 3D points transform the point cloud into a network modeled computationally as a graph with: nodes (representing a single CFTR protein); edges (interaction between pairs of proteins); and weights (encoding the distances between nodes, up to an upper threshold limit). Machine learning will then be used to identify network features, both network measures and graphlets, that distinguish normal and F508del-CFTR at various proximity thresholds, to identify the proximity threshold and measures or groups of measures that best discriminate between CFTR and F508del-CFTR clusters. We will the apply K2 and the mean square algorithm to determine whether multiple F508del-CFTR clusters are present and that may correspond to F508del-CFTR clusters differentially responsive to established CFTR correctors.

Testing for Effects of Targeted CFTR Drugs and Screening CF Patient Airway Epithelial Cells (Y2-3)

Three CFTR modulators are currently in clinical use. Ivacaftor (VX-770; Kalydeco) is a potentiator that increases the open probability of CFTR. Lumacaftor (VX-809) and tezacaftor (VX-661) are pharmacological chaperones that correct the folding of F508del-CFTR and some other mutants (21,22).

Orkambi is a combination of ivacaftor and lumacaftor and has been used to treat patients with F508del-CFTR. We will test whether these CFTR modulators, individually or in combination, correct the SMLM signature of F508del-CFTR and other trafficking mutants and extend these studies to CF patient airway epithelial cells to determine if CFTR SMLM signatures are present and correctable in clinical specimens.

Correction of F508del-CFTR SMLM Signatures by CFTR Modulators

Primary bronchial epithelial cells expressing CFTR wild-type and mutant constructs by adenoviral infection will be treated with Ivacaftor (VX-770), Lumacaftor (VX-809) and tezacaftor (VX-661) as well as combinations including Orkambi. Conditions for CFTR modulator treatments have been established and treatment will be 24-48 h at clinically relevant concentrations. Cells will be fixed and labeled and analyzed by the SMLM CFTR-specific Network analysis. Transduction and responses to correctors will be verified by functional studies of CFTR in Ussing chambers according to our standard methods (65). Triple combination therapies with one potentiator and two correctors are in clinical trials and show promise for F508del-CFTR patients and we recently showed that there is an additional corrector site that is biochemically and functionally distinct, raising the possibility of further improvement with a quadruple therapy (i.e. 1 potentiator and 3 correctors (30)). These studies will then be extended to CFTR potentiators, since they affect CFTR gating and therefore are expected to affect protein conformation. Cells expressing wild-type or G551D-CFTR will be treated with Kalydeco, Orkambi, and combination drugs currently in clinical trials and analyzed by SMLM. CFTR clustering and other dynamical changes in the presence of Kalydeco will be compared with those induced by Orkambi. In parallel, we will test for CFTR activity using standard Cl-transport assays and validate any results obtained using super-resolution STED microscopy method.

CF Patient Airway Cells

Analysis of CF patient airway cells will be completed and drug-induced structural changes in F508del-CFTR by SMLM network analysis with functional responsiveness to the drug will be assessed. CF patient lungs will be obtained after transplantation and normal donor lungs that are not suitable for transplantation. Each preparation is subjected to quality control procedures that includes differentiation and histology, assays of CFTR function and corrector responses, tests for viral and *mycoplasma* contamination etc. Thus, the responsiveness to CFTR modulators of cells from each patient will be determined.

REFERENCES

Aldoma, A., Marton, Z. C., Tombari, F., Wohlkinger, W., Potthast, C., Zeisl, B., Rusu, R. B., Gedikli, S., and Vincze, M. (2012). Tutorial Point Cloud Library Three- Dimensional Object Recognition and 6 DOF Pose Estimation. IEEE Robotics & Automation Magazine 19, 80-91.

AHMED, N. K., NEVILLE, J., ROSSI, R. A. & DUFFIELD, N. Efficient graphlet counting for large networks. 2015 2015. IEEE, 1-10.

AHMED, N. K., NEVILLE, J., ROSSI, R. A., DUFFIELD, N. G. & WILLKE, T. L. 2017. Graphlet decomposition: Framework, algorithms, and applications. *Knowledge and Information Systems*, 50, 689-722.

Andronov, L., Orlov, I., Lutz, Y., Vonesch, J. L., and Klaholz, B. P. (2016). ClusterViSu, a method for clustering of protein complexes by Voronoi tessellation in super-resolution microscopy. Sci Rep 6, 24084.

Annibale, P., Vanni, S., Scarselli, M., Rothlisberger, U., and Radenovic, A. (2011a). Identification of clustering artifacts in photoactivated localization microscopy. Nat Methods 8, 527-528.

Annibale, P., Vanni, S., Scarselli, M., Rothlisberger, U., and Radenovic, A. (2011b). Quantitative photo activated localization microscopy: unraveling the effects of photoblinking. PLoS One 6, e22678.

Ariotti, N., J. Rae, N. Leneva, C. Ferguson, D. Loo, S. Okano, M. M. Hill, P. Walser, B. M. Collins, and R. G. Parton. 2015. Molecular Characterization of Caveolin-induced Membrane Curvature. J. Biol. Chem. 290:24875-24890.

Barabasi, A. L., and Oltvai, Z. N. (2004). Network biology: understanding the cell's functional organization. Nat Rev Genet 5, 101-113.

Baronchelli, A., Ferrer-i-Cancho, R., Pastor-Satorras, R., Chater, N., and Christiansen, M. H. (2013). Networks in cognitive science. Trends Cogn Sci 17, 348-360.

BASSETT, D. S. & SPORNS, O. 2017. Network neuroscience. *Nature neuroscience*, 20, 353.

BENSON, A. R., GLEICH, D. F. & LESKOVEC, J. 2016. Higher-order organization of complex networks. *Science*, 353, 163-166.

Berger, M., Tagliasacchi, A., Seversky, L., Alliez, P., Levine, J., Sharf, A., and Silva, C. (2014). State of the Art in Surface Reconstruction from Point Clouds. Eurographics, Strasbourg, France, 1, 161-185.

Botsch, M., Kobbelt, L., Pauly, M., Alliez, P., and Levy, B. (2010). Polygon Mesh Processing. Taylor & Francis.

Breiman, L. (2001). Random forests. Machine Learning 45, 5-32.

BRESSAN, M., CHIERICHETTI, F., KUMAR, R., LEUCCI, S. & PANCONESI, A. Counting graphlets: Space vs time. 2017 2017. ACM, 557-566.

Brown, C. J., Miller, S. P., Booth, B. G., Andrews, S., Chau, V., Poskitt, K. J., and Hamarneh, G. (2014). Structural network analysis of brain development in young preterm neonates. Neuroimage 101, 667-680.

Caetano, F. A., Dirk, B. S., Tam, J. H., Cavanagh, P. C., Goiko, M., Ferguson, S. S., Pasternak, S. H., Dikeakos, J. D., de Bruyn, J. R., and Heit, B. (2015). MIiSR: Molecular Interactions in Super-Resolution Imaging Enables the Analysis of Protein Interactions, Dynamics and Formation of Multi-protein Structures. PLoS Comput Biol 11, e1004634.

Comaniciu, D., and Meer, P. (2002). Mean shift: A robust approach toward feature space analysis. IEEE Trans on Pattern Analysis and Machine Intelligence 24, 603-619.

COSTA, L. D. F., RODRIGUES, F. A. & CRISTINO, A. S. 2008. Complex networks: the key to systems biology. Genetics and Molecular Biology, 31, 591-601.

Dempsey, G. T., J. C. Vaughan, K. H. Chen, M. Bates, and X. Zhuang. 2011a. Evaluation of fluorophores for optimal performance in localization-based super-resolution imaging. Nature methods. 8:1027-1036.

Dempsey, G. T., J. C. Vaughan, K. H. Chen, M. Bates, and X. Zhuang. 2011b. Evaluation of fluorophores for optimal performance in localization-based super-resolution imaging. Nature methods. 8:1027.

Dempsey, G. T., Vaughan, J. C., Chen, K. H., and Zhuang, X. W. (2012). Evaluation of Fluorophores for Optimal Performance in Localization-Based Super-Resolution Imaging. Biophysical Journal 102, 725a-725a.

DUTTA, A. & SAHBI, H. 2017. High order stochastic graphlet embedding for graph-based pattern recognition. arXiv preprint arXiv:1702.00156.

El Beheiry, M., and Dahan, M. (2013). ViSP: representing single-particle localizations in three dimensions. Nat Methods 10, 689-690.

Fernandez-Leiro, R., and Scheres, S. H. W. (2016). Unravelling biological macromolecules with cryo-electron microscopy. Nature (Lond.) 537, 339-346.

Folling, J., Bossi, M., Bock, H., Medda, R., Wurm, C. A., Hein, B., Jakobs, S., Eggeling, C., and Hell, S. W. (2008). Fluorescence nanoscopy by ground-state depletion and single-molecule return. Nat Methods 5, 943-945.

Foi, M. Trimeche, V. Katkovnik, and K. Egiazarian. 2008. Practical Poissonian-Gaussian noise modeling and fitting for single-image raw-data. *IEEE Trans Image Process.* 17:1737-1754.

Fricke, F., Beaudouin, J., Eils, R., and Heilemann, M. (2015). One, two or three? Probing the stoichiometry of membrane proteins by single-molecule localization microscopy. Sci Rep 5, 14072.

Fukunaga, K., and Hostetler, L. (1975). The estimation of the gradient of a density function, with applications in pattern recognition. IEEE Trans on Information Theory 21, 32-40.

Gambin, Y., Ariotti, N., McMahon, K. A., Bastiani, M., Sierecki, E., Kovtun, O., Polinkovsky, M. E., Magenau, A., Jung, W., Okano, S., Zhou, Y., Leneva, N., Mureev, S., Johnston, W., Gaus, K., Hancock, J. F., Collins, B. M., Alexandrov, K., and Parton, R. G. (2014). Single-molecule analysis reveals self assembly and nanoscale segregation of two distinct cavin subcomplexes on caveolae. Elife 3, e01434.

Goreaud, F., and Pélissier, R. (1999). On explicit formulas of edge effect correction for Ripley's K-function. Journal of Vegetation Science 10, 433-438.

GROVER, A. & LESKOVEC, J. node2vec: Scalable feature learning for networks. 2016 2016. ACM, 855-864.

GUMHOLD, S., WANG, X. & MACLEOD, R. S. Feature Extraction From Point Clouds. 2001.

HANSEN, C. G., SHVETS, E., HOWARD, G., RIENTO, K. & NICHOLS, B. J. 2013. Deletion of cavin genes reveals tissue-specific mechanisms for morphogenesis of endothelial caveolae. *Nat Commun*, 4, 1831.

Hayer, A., Stoeber, M., Bissig, C., and Helenius, A. (2010). Biogenesis of caveolae: stepwise assembly of large caveolin and cavin complexes. Traffic 11, 361-382.

Hill, M. M., Bastiani, M., Luetterforst, R., Kirkham, M., Kirkham, A., Nixon, S. J., Walser, P., Abankwa, D., Oorschot, V. M., Martin, S., Hancock, J. F., and Parton, R. G. (2008). PTRF-Cavin, a conserved cytoplasmic protein required for caveola formation and function. Cell 132, 113-124.

HOČEVAR, T. & DEMŠAR, J. 2014. A combinatorial approach to graphlet counting. *Bioinformatics*, 30, 559-565.

Huang, B., Wang, W., Bates, M., and Zhuang, X. (2008). Three-dimensional super-resolution imaging by stochastic optical reconstruction microscopy. Science 319, 810-813.

Khater, I. M., F. Meng, T. H. Wong, I. R. Nabi, and G. Hamarneh. 2018. Super Resolution Network Analysis Defines the Molecular Architecture of Caveolae and Caveolin-1 Scaffolds. *Scientific Reports.* 8:9009.

Kim, J., and T. Wilhelm. 2008. What is a complex graph? *Physica A: Statistical Mechanics and its Applications.* 387:2637-2652.

KOLLIAS, G., MOHAMMADI, S. & GRAMA, A. 2012. Network similarity decomposition (nsd): A fast and scalable approach to network alignment. *IEEE Transactions on Knowledge and Data Engineering*, 24, 2232-2243.

Kovtun, O., Tillu, V. A., Jung, W., Leneva, N., Ariotti, N., Chaudhary, N., Mandyam, R. A., Ferguson, C., Morgan, G. P., Johnston, W. A., Harrop, S. J., Alexandrov, K., Parton, R. G., and Collins, B. M. (2014). Structural insights into the organization of the cavin membrane coat complex. Dev. Cell 31, 405-419.

KRIVITSKY, P. N., HANDCOCK, M. S., RAFTERY, A. E. & HOFF, P. D. 2009. Representing degree distributions, clustering, and homophily in social networks with latent cluster random effects models. *Social networks*, 31, 204-213.

Lagache, T., Sauvonnet, N., Danglot, L., and Olivo-Marin, J. C. (2015). Statistical analysis of molecule colocalization in bioimaging. Cytometry A 87, 568-579.

Lajoie, P., Goetz, J. G., Dennis, J. W., and Nabi, I. R. (2009). Lattices, rafts, and scaffolds: domain regulation of receptor signaling at the plasma membrane. J. Cell Biol. 185, 381-385.

Levet, F., Hosy, E., Kechkar, A., Butler, C., Beghin, A., Choquet, D., and Sibarita, J. B. (2015). SR-Tesseler: a method to segment and quantify localization-based super-resolution microscopy data. Nat Methods 12, 1065-1071.

Lillemeier, B. F., Mortelmaier, M. A., Forstner, M. B., Huppa, J. B., Groves, J. T., and Davis, M. M. (2010). TCR and Lat are expressed on separate protein islands on T cell membranes and concatenate during activation. Nat Immunol 11, 90-96.

Liu, Q., L. Chen, H. C. Aguilar, and K. C. Chou. 2018. A stochastic assembly model for Nipah virus revealed by super-resolution microscopy. *Nature communications.* 9:3050.

LIU, L. & PILCH, P. F. 2008. A critical role of cavin (polymerase I and transcript release factor) in caveolae formation and organization. *J Biol Chem*, 283, 4314-22.

Ludwig, A., Howard, G., Mendoza-Topaz, C., Deerinck, T., Mackey, M., Sandin, S., Ellisman, M. H., and Nichols, B. J. (2013). Molecular composition and ultrastructure of the caveolar coat complex. PLoS biology 11, e1001640.

Ludwig, A., B. J. Nichols, and S. Sandin. 2016. Architecture of the caveolar coat complex. *J. Cell Sci.* 129:3077-3083.

MARCUS, D. & SHAVITT, Y. 2012. Rage—a rapid graphlet enumerator for large networks. *Computer Networks*, 56, 810-819.

Mazouchi, A., and Milstein, J. N. (2016). Fast Optimized Cluster Algorithm for Localizations (FOCAL): a spatial cluster analysis for super-resolved microscopy. Bioinformatics 32, 747-754.

MILO, R., SHEN-ORR, S., ITZKOVITZ, S., KASHTAN, N., CHKLOVSKII, D. & ALON, U. 2002. Network motifs: simple building blocks of complex networks. Science, 298, 824-827.

Monier, S., Parton, R. G., Vogel, F., Behlke, J., Henske, A., and Kurzchalia, T. V. (1995). VIP21-caveolin, a membrane protein constituent of the caveolar coat, oligomerizes in vivo and in vitro. Mol. Biol. Cell 6, 911-927.

Newman, M. (2010). Networks: An Introduction. Oxford University Press, Inc.

Newman, M. E. J. 2006a. Finding community structure in networks using the eigenvectors of matrices. *Physical review E.* 74:036104.

Newman, M. E. (2006b). Modularity and community structure in networks. Proc Natl Acad Sci USA 103, 8577-8582.

Newman, M. E. J. (2003). The structure and function of complex networks. Siam Review 45, 167-256.

Newman, M. E. J. 2013. Spectral methods for community detection and graph partitioning. Physical Review E. 88:042822.

Owen, D. M., Rentero, C., Rossy, J., Magenau, A., Williamson, D., Rodriguez, M., and Gaus, K. (2010). PALM imaging and cluster analysis of protein heterogeneity at the cell surface. J Biophotonics 3, 446-454.

Pageon, S. V., Cordoba, S. P., Owen, D. M., Rothery, S. M., Oszmiana, A., and Davis, D. M. (2013). Superresolution microscopy reveals nanometer-scale reorganization of inhibitory natural killer cell receptors upon activation of NKG2D. Sci Signal 6, ra62.

Parton, R. G., and Simons, K. (2007). The multiple faces of caveolae. Nat. Rev. Mol. Cell Biol. 8, 185-194.

Partn, R. G., and M. A. del Pozo. 2013. Caveolae as plasma membrane sensors, protectors and organizers. *Nat. Rev. Mol. Cell Biol.* 14:98-112.

Pelkmans, L., and Zerial, M. (2005a). Kinase-regulated quantal assemblies and kiss-and-run recycling of caveolae. Nature 436, 128-133.

Pelkmans, L., and Zerial, M. (2005b). Kinase-regulated quantal assemblies and kiss-and-run recycling of caveolae 436, 128-133.

Pelleg, D., and Moore, A. W. (2000). X-means: Extending K-means with Efficient Estimation of the Number of Clusters. In: Proc of the 17th International Conference on Machine Learning: Morgan Kaufmann Publishers Inc., 727-734.

Pereira, C. F., Rossy, J., Owen, D. M., Mak, J., and Gaus, K. (2012). HIV taken by STORM: super-resolution fluorescence microscopy of a viral infection. Virol J 9, 84.

PRULJ, N. 2007. Biological network comparison using graphlet degree distribution. *Bioinformatics*, 23, e177-e183.

PRULJ, N., CORNEIL, D. G. & JURISICA, I. 2004. Modeling interactome: scale-free or geometric? *Bioinformatics*, 20, 3508-3515.

Q I, C. R., SU, H., M O, K. & GUIBAS, L. J. 2017. Pointnet: Deep learning on point sets for 3d classification and segmentation. *Proc. Computer Vision and Pattern Recognition (CVPR), IEEE*, 1, 4.

Quan, T., Zeng, S., and Huang, Z. L. (2010). Localization capability and limitation of electron multiplying charge-coupled, scientific complementary metal-oxide semiconductor, and charge coupled devices for super resolution imaging. J Biomed Opt 15, 066005.

Ries, J., C. Kaplan, E. Platonova, H. Eghlidi, and H. Ewers. 2012. A simple, versatile method for GFP-based super-resolution microscopy via nanobodies. *Nature methods*. 9:582-584.

ROSSI, R. A., ZHOU, R. & AHMED, N. K. 2017. Estimation of graphlet statistics. *ArXiv preprint arXiv:* 1701.01772.

Rossy, J., Cohen, E., Gaus, K., and Owen, D. M. (2014). Method for co-cluster analysis in multichannel single-molecule localisation data. Histochem Cell Biol 141, 605-612.

Rossy, J., Owen, D. M., Williamson, D. J., Yang, Z., and Gaus, K. (2013). Conformational states of the kinase Lck regulate clustering in early T cell signaling. Nat Immunol 14, 82-89.

Rothberg, K. G., Heuser, J. E., Donzell, W. C., Ying, Y. S., Glenney, J. R., and Anderson, R. G. (1992). Caveolin, a protein component of caveolae membrane coats. Cell 68, 673-682.

Rubin-Delanchy, P., Burn, G. L., Griffie, J., Williamson, D. J., Heard, N. A., Cope, A. P., and Owen, D. M. (2015). Bayesian cluster identification in single-molecule localization microscopy data. Nat Methods 12, 1072-1076.

Rubinov, M., and Sporns, O. (2010). Complex network measures of brain connectivity: uses and interpretations. Neuroimage 52, 1059-1069.

Sargiacomo, M., Scherer, P. E., Tang, Z., Kubler, E., Song, K. S., Sanders, M. C., and Lisanti, M. P. (1995). Oligomeric structure of caveolin: implications for caveolae membrane organization. Proc Natl Acad Sci U.S.A. 92, 9407-9411.

Scheiffele, P., Verkade, P., Fra, A. M., Virta, H., Simons, K., and Ikonen, E. (1998). Caveolin-1 and -2 in the exocytic pathway of MDCK cells. J Cell Biol 140, 795-806.

Shroff, H., C. G. Galbraith, J. A. Galbraith, and E. Betzig. 2008. Live-cell photoactivated localization microscopy of nanoscale adhesion dynamics. Nat Meth. 5:417-423.

SHERVASHIDZE, N., VISHWANATHAN, S. V. N., PETRI, T., MEHLHORN, K. & BORGWARDT, K. Efficient graphlet kernels for large graph comparison. 2009 2009. 488-495.

SHIN, K., ELIASSI-RAD, T. & FALOUTSOS, C. CoreScope: Graph Mining Using k-Core Analysis—Patterns, Anomalies and Algorithms. 2016 2016. IEEE, 469-478.

Sinha, B., D. Koster, R. Ruez, P. Gonnord, M. Bastiani, D. Abankwa, R. V. Stan, G. Butler-Browne, B. Vedie, L. Johannes, N. Morone, R. G. Parton, G. Raposo, P. Sens, C. Lamaze, and P. Nassoy. 2010. Cells respond to mechanical stress by rapid disassembly of caveolae. *Cell*. 144:402-413.

Sporns, O. (2013). Structure and function of complex brain networks. Dialogues Clin Neurosci 15, 247-262.

Stoeber, M., Schellenberger, P., Siebert, C. A., Leyrat, C., Helenius, A., and Grunewald, K. (2016). Model for the architecture of caveolae based on a flexible, net-like assembly of Cavin1 and Caveolin discs. Proc. Natl. Acad. Sci. USA 113, E8069-E8078.

Tafteh, R., L. Abraham, D. Seo, H. Y. Lu, M. R. Gold, and K. C. Chou. 2016a. Real-time 3D stabilization of a super-resolution microscope using an electrically tunable lens. *Opt. Express*. 24:22959-22970.

Tafteh, R., D. R. Scriven, E. D. Moore, and K. C. Chou. 2016b. Single molecule localization deep within thick cells; a novel super-resolution microscope. *J Biophotonics*. 9:155-160. Thompson, R. E., D. R. Larson, and W. W. Webb. 2002. Precise nanometer localization analysis for individual fluorescent probes. *Biophys. J*. 82:2775-2783.

Venkataramani, V., Herrmannsdorfer, F., Heilemann, M., and Kuner, T. (2016). SuReSim: simulating localization microscopy experiments from ground truth models. Nature methods 13, 319-321.

Walser, P. J., Ariotti, N., Howes, M., Ferguson, C., Webb, R., Schwudke, D., Leneva, N., Cho, K. J., Cooper, L., Rae, J., Floetenmeyer, M., Oorschot, V. M., Skoglund, U., Simons, K., Hancock, J. F., and Parton, R. G. (2012). Constitutive formation of caveolae in a bacterium. Cell 150, 752-763.

Westin, C.-F., Peled, S., Gudbjartsson, H., Kikinis, R., and Jolesz, F. A. (1997). Geometrical diffusion measures for MRI from tensor basis analysis. Proc of ISMRM, 97, 1742.

YIN, H., BENSON, A. R., LESKOVEC, J. & GLEICH, D. F. Local higher-order graph clustering. 2017 2017. ACM, 555-564.

ZHANG, L., HAN, Y., YANG, Y., SONG, M., YAN, S. & TIAN, Q. 2013. Discovering discriminative graphlets for aerial image categories recognition. *IEEE Transactions on Image Processing*, 22, 5071-5084.

ZITNIK, M. & LESKOVEC, J. 2017. Predicting multicellular function through multi-layer tissue networks. *Bioinformatics*, 33, i190-i198.

The disclosure of all patents, publications, including published patent applications, and database entries referenced in this specification are expressly incorporated by reference in their entirety to the same extent as if each such individual patent, publication, and database entry were expressly and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

We claim:

1. A method of defining molecular architecture of a fluorophore labelled structure in a biological sample, the method comprising:

capturing a series of single molecule localization microscopy (SMLM) optical images of said structure, wherein said structure comprises a protein labelled with a fluorophore;

mapping a three-dimensional (3D) location of each single emission event in a plurality of single emission events from the series of SMLM optical images to create a 3D point cloud;

refining the 3D point cloud by merging two or more single emission events;

removing one or more single emission events that correspond to randomly generated points;

completing a multi-threshold network analysis to identify clusters within the refined 3D point cloud;

identifying non-biological network nano-clusters resulting from multiple emissions from a single fluorophore in the refined 3D point cloud, wherein multiple emissions from the single fluorophore are two or more emission events within 20 nm;

removing the non-biological network nano-clusters from the refined 3D point cloud; and extracting features for each cluster at a threshold of 60 nm-140 nm to obtain size, shape and topology of each cluster and thereby define the molecular architecture of the fluorophore labelled structure;

wherein the extracting features for each cluster uses machine learning;

wherein non-biological networks are distinguished from biological networks in the 3D point cloud by performing a multi-scale network analysis of the 3D point cloud and determining a network degree distribution for each proximity threshold; and wherein the refining of the 3D point cloud optionally comprises iterative steps.

2. The method of claim 1, wherein the merging of two or more single emission events is based on proximity with crisp or fuzzy proximity threshold and optionally wherein single emission events within a specified distance or merge threshold are merged.

3. The method of claim 2, wherein the merge threshold is based on the resolution limit of the SMLM microscopy or merge threshold is determined based on an analysis of non-biological networks in the 3D point cloud.

4. The method of claim 2, wherein single emission events within a specified distance or merge threshold are merged and wherein the specified distance is assessed in two dimensions, three dimensions or is different in different dimensions.

5. The method of claim 1, wherein merging comprises replacing two or more single emission events with one single emission event at the average position of the two or more single emission events.

6. A method of defining molecular architecture of a fluorophore labelled structure in a biological sample, the method comprising:

capturing a series of single molecule localization microscopy (SMLM) optical images of said structure, wherein said structure comprises a protein labelled with a fluorophore;

mapping a three-dimensional (3D) location of each single emission event in a plurality of single emission events from a series of optical images of a sample to create a 3D point cloud;

refining the 3D point cloud by merging two or more single emission events into a node within a merge threshold to create a merged 3D point cloud, wherein the merge threshold is based on the resolution limit of the SMLM microscopy;

completing a multi-threshold network analysis to identify clusters within the refined 3D point cloud; and extracting features for each cluster at a threshold of 60 nm-140 nm to obtain size, shape and topology of each cluster and thereby define the molecular architecture of the fluorophore labelled structure;

wherein the extracting features for each cluster uses machine learning.

7. A method of defining molecular architecture of a fluorophore labelled structure in a biological sample, the method comprising:

capturing a series of single molecule localization microscopy (SMLM) optical images of said structure, wherein said structure comprises a protein labelled with a fluorophore;

mapping a three-dimensional (3D) location of each single emission event in a plurality of single emission events from a series of optical images of a sample to create a 3D point cloud;

refining the 3D point cloud by merging two or more single emission events into a node within a merge threshold to create a merged 3D point cloud, wherein the merge threshold is determined based on an analysis of non-biological networks resulting from multiple emissions from a single fluorophore in the 3D point;

cloud, wherein multiple emissions from the single fluorophore are two or more emission events within 20 nm;

completing a multi-threshold network analysis to identify clusters within the refined 3D point cloud; and extracting features for each cluster at a threshold of 60 nm-140 nm to obtain size, shape and topology of each cluster and thereby define the molecular architecture of the fluorophore labelled structure, wherein the extracting features for each cluster uses machine learning;

wherein a filtering step removes the non-biological network nano-clusters from the 3D point cloud; and wherein non-biological networks are distinguished from biological networks in the 3D point cloud by performing a multi-scale network analysis of the 3D point cloud and determining the network degree distribution for each proximity threshold.

8. The method of claim 6, comprising acquiring the series of optical images as a function of time.

9. The method of claim 6, comprising converting the 3D point cloud into a network or graph.

10. The method of claim 9, comprising comparing the network or graph or fragment thereof with one or more randomly generated networks or graphs or of fragment thereof.

11. The method of claim 6, wherein optical images are divided into one or more regions of interest.

12. The method of claim 6, wherein distance between nodes is measured.

13. The method of claim 6, wherein the method comprises comparing a merged 3D point cloud or networks with a merged 3D point cloud or network from a reference sample; wherein the reference sample is optionally a negative control.

14. The method of claim 13, wherein the comparison identifies differences in the merged 3D point cloud or network and the merged 3D point cloud or network from the reference sample.

15. The method of claim 13, wherein the comparison is at more than one threshold.

16. A non-transitory computer readable medium containing program instructions executable by a processor, the computer readable medium comprising program instructions to implement the method of claim 1.

17. A non-transitory computer readable medium containing program instructions executable by a processor, the computer readable medium comprising program instructions to implement the method of claim 6.

18. A non-transitory computer readable medium containing program instructions executable by a processor, the computer readable medium comprising program instructions to implement the method of claim 7.

19. The method of claim 1, wherein the protein labelled with a fluorophore is a protein labelled with a fluorophore conjugated antibody, is a fusion protein comprising a fluorescent protein or a photoactivatable fluorescent protein.

20. The method of claim 6, wherein the protein labelled with a fluorophore is a protein labelled with a fluorophore conjugated antibody, is a fusion protein comprising a fluorescent protein or a photoactivatable fluorescent protein.

21. The method of claim 7, wherein the protein labelled with a fluorophore is a protein labelled with a fluorophore conjugated antibody, is a fusion protein comprising a fluorescent protein or a photoactivatable fluorescent protein.

22. The method of claim 1, wherein the machine learning is based on 3D pattern analysis.

23. The method of claim 1, wherein the machine learning is based on the Newman method.

\* \* \* \* \*